(12) United States Patent
Chandran

(10) Patent No.: US 8,188,311 B2
(45) Date of Patent: May 29, 2012

(54) L-THREONINE DERIVATIVES OF HIGH THERAPEUTIC INDEX

(75) Inventor: V. Ravi Chandran, Allen, TX (US)

(73) Assignee: Signature R&D Holdings, LLC, Allen, TX (US)

( * ) Notice: Subject to any disclaimer, the term of this patent is extended or adjusted under 35 U.S.C. 154(b) by 230 days.

(21) Appl. No.: 12/557,030

(22) Filed: Sep. 10, 2009

(65) Prior Publication Data

US 2010/0069446 A1  Mar. 18, 2010

Related U.S. Application Data

(63) Continuation of application No. 11/442,027, filed on May 26, 2006, now Pat. No. 7,589,233, which is a continuation-in-part of application No. 11/343,557, filed on Jan. 30, 2006, which is a continuation-in-part of application No. PCT/US2004/024901, filed on Jul. 29, 2004.

(60) Provisional application No. 60/491,331, filed on Jul. 29, 2003.

(51) Int. Cl.
*C07C 229/00* (2006.01)

(52) U.S. Cl. ........................................ 562/570

(58) Field of Classification Search .................. 562/570; 514/21.91

See application file for complete search history.

(56) References Cited

U.S. PATENT DOCUMENTS

| | | |
|---|---|---|
| 3,934,027 A | 1/1976 | Hess et al. |
| 4,127,535 A | 11/1978 | Coy et al. |
| 4,146,611 A | 3/1979 | Ondetti et al. |
| 4,565,874 A | 1/1986 | Bergeron, Jr. |
| 4,601,979 A | 7/1986 | Andresen et al. |
| 5,036,052 A | 7/1991 | Ozeki et al. |
| 5,110,797 A | 5/1992 | Ienaga et al. |
| 5,800,804 A | 9/1998 | Laney |
| 7,420,002 B2 | 9/2008 | Gallop et al. |

OTHER PUBLICATIONS

The Merck index, 11th Edition, p. 69 (Merck & Co. Inc., 1989).

*Primary Examiner* — David Lukton
(74) *Attorney, Agent, or Firm* — Scully, Scott, Murphy & Presser, P.C.

(57) ABSTRACT

The present invention is directed to a derivative comprised of an L-Threonine bonded to a medicament or drug having a hydroxy, amino, carboxy or acylating derivative thereon. The derivative has the same utility as the drug from which it is made, but it has enhanced therapeutic properties. In fact, the derivatives of the present invention enhance at least one or more therapeutic qualities, as defined herein. The present invention is also directed to pharmaceutical compositions containing same.

6 Claims, 15 Drawing Sheets

L-THREONINE DERIVATIVES OF HIGH THERAPEUTIC INDEX

CROSS REFERENCE TO RELATED APPLICATIONS

This application is a continuation of U.S. patent application Ser. No. 11/442,027 filed May 26, 2006, now U.S. Pat. No. 7,589,233, which is a continuation-in-part of copending U.S. patent application Ser. No. 11/343,557 filed Jan. 30, 2006, which is a continuation-in-part of PCT Application No. PCT/US04/24901 filed Jul. 29, 2004, which claims benefit of Provisional Application No. 60/491,331, filed Jul. 29, 2003. This application incorporates by reference the subject matter disclosed in U.S. Ser. No. 11/442,027, U.S. Ser. No. 11/343,557 and PCT/US04/24901 in their entirety.

FIELD OF THE INVENTION

The invention relates to chiral separation of racemic and diastereomeric pharmaceutical compounds using L-Threonine, a naturally occurring amino acid and to methods of treating particular ailments, which are ameliorated by the administration of these enantiomerically and diastereomerically pure drugs and/or their corresponding L-Threonine ester/amide derivatives and to pharmaceutical compositions containing these substantially pure drugs and substantially pure L-Threonine derivatives.

The current invention involves improving many physicochemical, biopharmaceutical, and clinical efficacy of various drugs using L-Threonine as covalently bonded carriers for these drugs, with the additional advantage of separating various enantiomeric and diastereomeric drugs into their constitutent individual isomers.

BACKGROUND OF THE INVENTION

Chirality in organic and pharmaceutical chemistry plays a major role. While a vast majority of the new drugs introduced in the global pharmaceutical arena are chiral drugs and are resolved, there are a number of drugs in various therapeutic category that are still racemic and diastereromeric mixtures, such as Non-Steroidal Anti-Inflammatory drugs (NSAIDs) based on the structure of aryl propionic acid such as ibuprofen and other classes of drugs such as labatelol.

Drugs work in the mammalian body with so called pharmacological "receptors" that have specific shape whereby the drug molecules can only fit into these receptors like a "glove". Since it is not possible to superimpose a left handed glove on a right handed glove, the mirror images of the molecules are not superimposable.

The development of chemical compounds for the treatment of disorders, maladies and diseases has become increasingly difficult and costly. The probability of success for such development is often discouragingly low. Further, the time for development can approach or exceed ten years, leaving large numbers of patients without remedy for an extended period of time. In addition, the costs of developing a new drug for the treatment of any malady of significance might exceed a Billion dollars in a few years.

Even in cases in which effective pharmaceutical compounds have been developed, there are often disadvantages associated with their administration. These disadvantages can include aesthetic, biopharmaceutic, and pharmacokinetic bafflers affecting the effectiveness of some existing pharmaceutical compounds. For example, unpleasant taste or smell of a pharmaceutical compound or composition can be a significant barrier to patient compliance with respect to the administration regimen. The undesirable solubility characteristics of a pharmaceutical compound can also cause difficulty in the formulation of a homogeneous composition. Other disadvantages associated with known pharmaceutical compounds include: poor absorption of orally administered formulations; poor bioavailability of the pharmaceutical compounds in oral formulations; lack of dose proportionality; low stability of pharmaceutical compounds in vitro and in vivo; poor penetration of the blood/brain barrier; excessive first-pass metabolism of pharmaceutical compounds as they pass through the liver; excessive enterohepatic recirculation; low absorption rates; ineffective compound release at the site of action; excessive irritation, for example, gastro-intestinal irritability and/or ulceration; painful injection of parenterally administered pharmaceutical compounds and compositions; excessively high dosages required for some pharmaceutical compounds and compositions, and other undesirable characteristics. Some pharmaceutical compounds are processed by the body to produce toxic by-products with harmful effects.

The art is continually seeking new chemical compounds for the treatment of a wide variety of disorders, with improved properties to overcome the disadvantages of known pharmaceutical compounds mentioned above.

The present invention has overcome many problems associated with currently marketed drugs by making a derivative thereof. The concept of derivatives is well known, and there are a number of examples of such derivatives enumerated in the literature and there are a number of derivatives available in the market, including such diverse groups as statin drugs, ACE inhibitors, antiviral drugs such as Acyclovir and the like.

The present invention, however, uses specifically L-Threonine as the moiety to make the derivatives.

SUMMARY OF THE INVENTION

The present invention is directed to pharmaceutically active pure enantiomers of a derivative, having L-Threonine covalently bonded to a pharmaceutical compound (drugs) to form said acid derivative, which is administered in this form to the subject, such as a mammal. It is also directed to pharmaceutical compositions comprising a therapeutically effective amount of a L-Threonine covalently bounded to a drug and a pharmaceutical carrier therefor. It is also directed to the method of use of such drugs thus formed. The utility of the drug to which the L-Threonine moiety is attached is the same as that of the underlying drug from which the L-Threonine derivative is prepared.

BRIEF DESCRIPTION OF THE DRAWINGS

In FIG. 9, F1, F2 and F3 are respectively, ASA-Serine, ASA-Hydroxyproline and ASA-Threonine esters.

DETAILED DESCRIPTION OF THE PRESENT INVENTION

Figure 1:
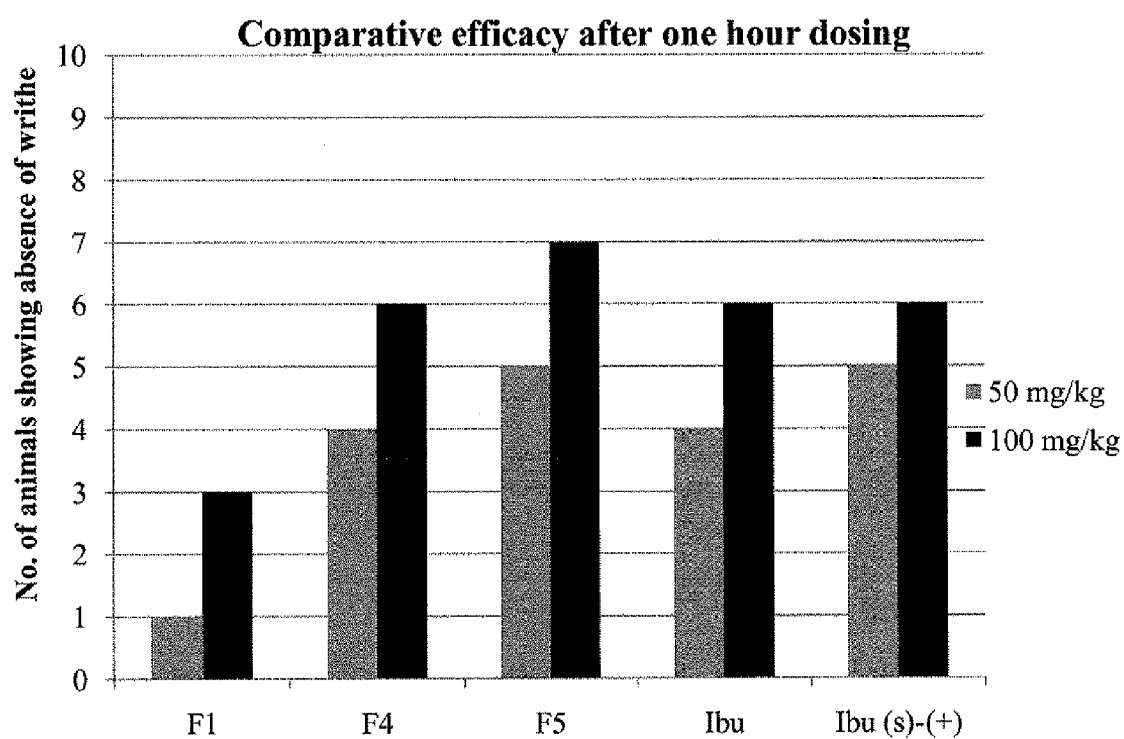
FIG. 1 graphically compares the efficacy of L-serine ester of (±) Ibuprofen (F1), L-threonine ester (±) Ibuprofen (F2) and L-hydroxyproline ester of (±) Ibuprofen (F3), (±) Ibuprofen (i.e., the racemic mixture) and Ibuprofen (S)(+), after one hour dosing, based on the antagonizing property of Acetylcholine induced writhe in Albino mice.

In one embodiment, the present invention is directed to L-threonine derivatives of drugs. L-Threonine is an ideal model to be used as a derivative, because it is capable of forming various types of linkages between itself and the drug. By definition, an L-Threonine has at least two functionalities thereon, an amino group ($NH_2$) and a carboxy group (COOH). For example, the α-L-Threonines have the well known structure

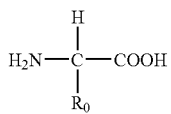

wherever $R_0$ is the side group or chain of the L-Threonine, i.e., $CH(OH)(CH_3)$. The

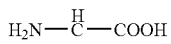

as defined herein, is the main chain of the L-Threonine. Thus, for example, besides the amino group and the carboxyl group on the main chain, the side chain has a functional group thereon, an OH group. It is the functional groups on the L-Threonine moiety that permits the covalent linkage to occur between the L-Threonine and the drug.

The drug or medicament useful in the present invention contains functional groups thereon that permit the drug to react with and form a covalent bond with the L-Threonine. Examples of functional groups present on the drugs include $NH_2$, OH, COOH or acid derivatives thereof, such as esters, amides and the like.

The mode of attachment between the pharmaceutical compound and the L-Threonine can be via:

1) An ester bond (—CO—O—) arising from condensation of a carboxylic acid and an alcohol or phenolic hydroxyl group, or through transesterification, for example:
   a) Where the pharmaceutical compound has an aliphatic or aromatic hydroxyl group an ester bond can be formed with the backbone carboxylic acid group of L-Threonine under esterification conditions; or
   b) Where the pharmaceutical compound has an aliphatic or aromatic hydroxyl group and the L-Threonine has the alcohol functionality on the side chain oxidized to an carboxylic acid, an ester bond can be formed therebetween under esterification conditions; or
   c) Where the pharmaceutical compound has a carboxylic acid group and the L-Threonine has a side chain aliphatic or aromatic hydroxyl group, an ester bond can be fowled therebetween under esterification condition; or
   d) Where the pharmaceutical compound has an ester group with a substituted or unsubstituted acyloxy (e.g., alkoxy- or arylalkoxy-, aryloxy carbonyl) substituent (compound-O—CO-substituent) and the L-Threonine has a backbone carboxylic acid group, an ester bond can be formed therebetween through transesterification; or
   e) Where the pharmaceutical compound has an ester group with a substituted or unsubstituted acyloxy (e.g., alkoxy- or arylalkoxy-, aryloxy carbonyl) substituent (compound-O—CO-substituent) and the L-Threonine side chain has been oxidized to a carboxylic acid group, an ester bond can be formed therebetween through transesterification; or
   f) Where the pharmaceutical compound has an ester group with a substituted or unsubstituted alkoxy- or arylalkoxy- or aryloxy carbonyl substituent (compound-CO—O-Substituent) and the L-Threonine has a side chain hydroxyl group, an ester bond can form therebetween though transesterification; or 2) An amide bond (—CO—NH—) arising from condensation of a carboxylic acid and an amine, for example:
   a) Where the pharmaceutical compound has an amino group and the L-Threonine has a backbone carboxylic acid group, an amide can be formed under amide forming conditions; or
   b) Where the pharmaceutical compound has an amino group and the L-Threonine side chain has been oxidized to a carboxylic acid group, an amide bond can form therebetween under amide forming conditions; or
   c) Where the pharmaceutical compound has a carboxylic acid group and the L-Threonine has a backbone amino group, an amide bond can form therebetween under amide forming conditions; or
   d) Where the pharmaceutical compound has a carboxylic acid group and the L-Threonine hyroxy group on the side chain has been converted to an amino group, for example, by nucleophilic substitution and, an amide bond can be formed therebetween under amide forming conditions.

Thus, the present invention is directed to the derivatives thus formed. A novel result of the present invention is that the naturally occurring L-Threonine was used to form the derivatives of a various classes of drugs containing —COON, —NH or —OH groups.

The derivatives of the present invention have a number of advantages. For example, when L-Threonine derivatives are administered by a number of routes such as oral, IV, rectal or other such methods, these derivatives are converted into active drug molecules. A significant advantage of the L-Threonine derivative is that it is non-toxic, and hence either assimilated into the body or safely excreted. This is quite unlike the characteristics exhibited by a number of derivatives available in the market, where the promoiety itself is toxic, as is the case with statin drugs, Enalapril, Benazapril and the like group of ace inhibitors, and a number of antibiotics such as pivoxil, Axetil, Cilexetil and the like groups, which are highly toxic, thereby reducing the therapeutic index of the active drug. Moreover, the L-Threonine derivatives of the present invention are significant in the fact that they can separate the racemic mixtures of a number of drugs. It can do this separation at minimal cost, and also it is very surprising to note that only L-Threonine is able to separate racemic mixtures of various drugs, and other hydroxyl group containing naturally occurring hydroxy containing amino acids, such as L-Serine or L-hydroxyproline do not have the same capability as described below. More specifically, it has been found that such threonine derivatives are easily separated as pure isomers from the required enantiomeric mixture. Furthermore, as shown hereinbelow the derivative thus formed has advantages not realized relative to the drug without the L-Threonine attached thereto. For example, it can improve bioavailability, efficacy, be less toxic, exhibit greater solubility in water and/or improve the ability of the drug to pass into the cell membrane or through blood brain barrier, exhibit less side effects, such as gastro-intestinal irritability, enhanced therapeutic index and the like.

Thus, the present invention is directed to a method of improving the therapeutic quality of a drug wherein the improvement in the therapeutic quality is selected from the group consisting of improved efficacy, enhanced therapeutic index, increased solubility in the mammal's internal fluid, improved passage through the cell membrane, improved passage through the blood brain barrier, decreased side effects, such as significantly decreased irritation and/or ulcerations, less toxicity, enhanced absorption ratio and the like relative to the corresponding drug administered to the patient in the non-derivative form, said method comprising reacting the drug with an L-Threonine to form a covalent bond therebetween and administering the product thereof (hereinafter "derivative") to a patient. The derivatives of the present invention have at least one of the aforementioned improved qualities. In fact, they exhibit preferably at least two of the improved qualities cited hereinabove. Other advantages of the L-Threonine derivatives of the drugs of the present invention include the wide availability of the L-Threonines and the ease in which the reactions take place. For example, when L-threonine is reacted with the drug to form an amide or other ester, the reaction to form the amide or ester is generally more efficient and yields are very high, presumably above about 70% and more preferably above about 80% and most preferably above about 90%.

Most importantly, the preparation of the compounds of the present invention readily separates the enantiomers from a racemic mixture. For instance, it is well known in the art, when a drug is presented as an enantiomeric mixture, only one optically active form is responsible for the drug's pharmacological activity. This phenomenon has been repeatedly demonstrated for the whole class of NSAIDs, and ACE inhibitors, statin drugs and other therapeutic categories. The present invention surprisingly is able to separate the enantiomers without much additional work using L-Threonine, the naturally occurring amino acid, and the resulting derivative also shows significant improvement in therapeutic efficacy.

Thus, L-Threonine is useful not only to separate the racemic mixtures of pharmacologically active drugs to their corresponding individual isomers, but it also produces useful derivatives that are pharmacologically and biopharmaceutically superior to the corresponding parent active drugs.

As used here, the terms "drug", "medicament", and "pharmaceutical" are being used interchangeably and refer to the active compound that is administered to the patient without attachment of the L-Threonine thereto. Moreover, as used herein, the drug contains a functional group thereon capable of reacting with the L-Threonine, such as $NH_2$, OH, COOH or acylating derivatives thereof (e.g., ester, anhydride, amide, and the like) and the like.

The drug may be a peptide or contain a peptide. In accordance with the present invention, the threonine does not replace one of the amino acids in the peptide. Nor does the L-threonine derivative refer to the drug comprised of a peptide containing a L-threonine moiety on the molecule. On the contrary, as described herein, just as with any other drug, the L-threonine moiety is added to the drug by covalently bonding it to the peptide, either on a side chain or preferably with the amino group or N-amino end or with the carboxy group on the carboxy end of the peptide. When the drug is linked to an L-Threonine, the term "L-Threonine derivative" or "derivative of the present invention", or "compound of the present invention" or synonym thereto is utilized.

Among the L-Threonines useful in reacting with the drugs, it has been found that naturally occurring L-Threonine is the most useful amino acid to separate enantiomeric mixtures of active drugs. One who is normally trained in the art of understanding the medicinal chemistry and pharmacological activity would think that if L-Threonine is able to separate enantiomeric mixtures of the active drugs, then other Hydroxyl group containing amino acids such as Serine, Hydroxyproline or Tyrosine, should also be able to separate the enantiomeric mixtures. However, surprisingly, it has been found that L-Threonine is the most effective separating the enantiomeric mixtures and that the other amino acids, including the hydroxy containing amino acids, do not so readily.

Thus, the inventor has found that Threonine is extremely effective when it comes to the separation of enantiomers and diastereoisomers. The absolute configuration of L-Threonine is shown below:

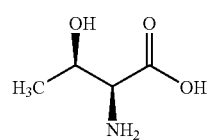

[R-R*,S*)]-2-amino-3-hydroxybutanoic acid

The following reaction schemes depict the reactions discussed hereinabove with respect to the reaction of hydroxyl, carboxyl and amine containing drugs with L-Threonine.

Reaction Scheme A: Where the hydroxyl group of the drug is reacted with the carboxyl group of L-Threonine to from the ester derivative

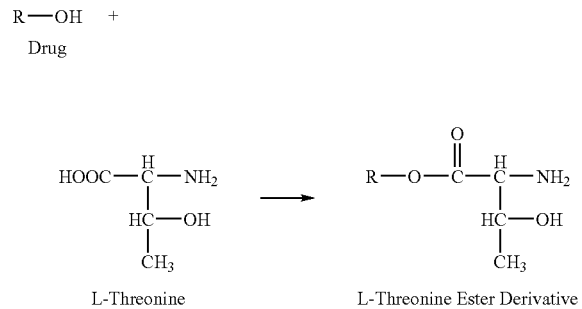

Reaction Scheme B: Where the carboxyl group of the drug is reacted with the hydroxyl group of L-Threonine wherein the hydroxy group is on the side chain to form the ester derivative.

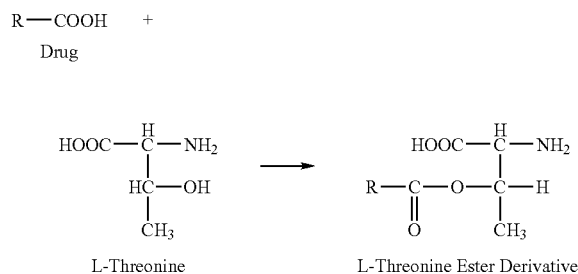

Reaction Scheme C: Where the amine group of the drug is reacted with the carboxyl group of L-Threonine to from the amide derivative

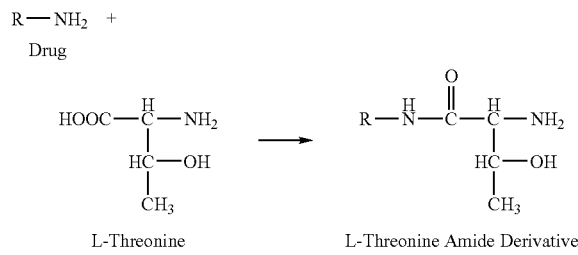

Reaction Scheme D: Where the carboxyl group of the drug is reacted with the carboxyl group of the L-Threonine to form the anhydride derivative.

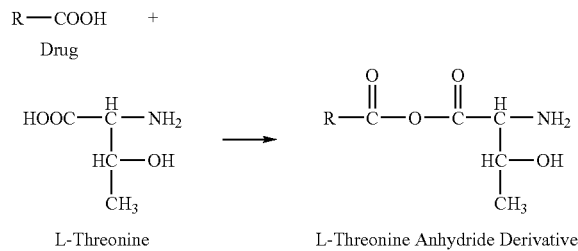

Reaction Scheme E: Where the amine group of the drug is reacted with the amine group of the L-Threonine to form the azo derivative derivative.

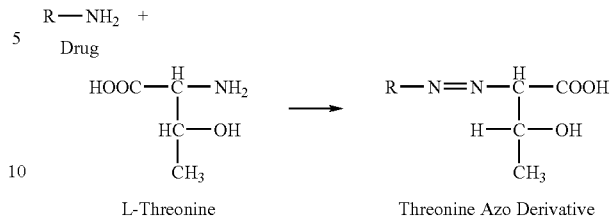

Reaction Scheme F: Where the carboxyl group of the drug is reacted with the amine group of the L-Threonine to form the amide derivative.

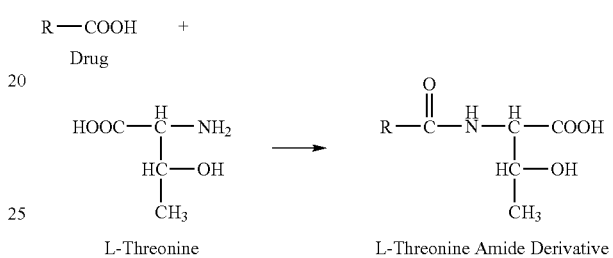

As used herein the term "L-Threonine" refers to an organic compound having therein a carboxyl group (COOH) and an amino group ($NH_2$) or salts thereof in the L-configuration. In solution, these two terminal groups ionize to form a double ionized, through overall neutral entity identified as zwitterions. The ionic ends are stabilized in aqueous solution by polar water molecules.

The term L-Threonine or "acylating derivative" thereof refers to the L-Threonine amino acid or an acylating derivative thereof, such as halide (e.g., Br, Cl, I or F), ester (e.g., lower alkylester, aryl ester, aryl lower alkyl ester, cycloalkyl ester, cycloalkylloweralkyl ester heterocyclic ester or lower alkylheterocyclic ester or an anhydride, e.g., N-carboxyanhydride of Threonine.

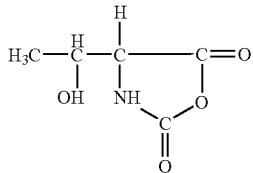

When the side group of the Threonine, the hydroxy group become involved in the acylating reaction described above, the bond thus formed may be depicted as $OAA_1$ wherein $AA_1$ is L-Threonine residue without the hydroxy group, i.e.,

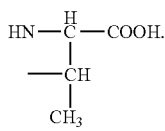

Thus, $AA_1$ by this definition, refers to the L-Threonine without the hydroxy side group since it took part in the reaction in forming the ester. Moreover, when an ester is formed between the hydroxy group of the L-Threonine and the OH group of the drug, the hydroxy group on the carboxy group forms a byproduct with the hydrogen of the hydroxy group, thus, the resulting product does not have the OH group on the carboxy group, but just the acyl moiety.

On the other hand, the amide bond may be depicted as C(=O)—NHAA wherein AA is

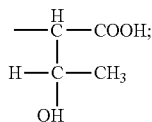

this means that the L-Threonine forms an amide bond between the carboxy group on the drug and the amino group of the L-Threonine. However, as written, since the NH from the amide bond comes from the L-Threonine, AA is the L-Threonine without the amino group. Finally, the bond may form between the carboxy group of the L-Threonine and the amino group or hydroxy group of the drug. In such a case, the molecule is depicted as

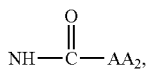

wherein $AA_2$ is

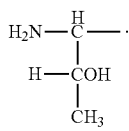

There appears to be only one preferred L-Threonine, the naturally occurring L-Threonine, whose structure is shown above. Only drugs that are tertiary amines can not participate in formation of amides. Secondary amines can be reacted to form amides. Primary amines can be reacted with L-Threonine to form either azo bond or an amide linkage.

The derivatives are prepared from a drug having a group thereon which can react with the L-Threonine.

The preferred drugs that are reacted with L-Threonines in accordance with various schemes are shown in the table below. This is only representative examples, and not inclusive of all the drugs.

| Drug | Reaction Schemes | | | | | |
|---|---|---|---|---|---|---|
| | A | B | C | D | E | F |
| Abacavir | YES | | YES | | YES | |
| Acarbose | YES | | | | | |
| Acebutolol | YES | | YES | | | |
| Adefovir | YES | | | | | |
| Albuterol | YES | | YES | | | |
| Amlodipine[1] | | | YES | | | |
| Amphotericin B | YES | YES | | YES | | YES |
| Amprenavir | YES | | YES | | YES | |
| Atenolol | YES | | YES | | YES | |
| Atorvastatin | YES | YES | | YES | | YES |
| Atropine | YES | | | | | |
| Baclofen | | YES | YES | YES | YES | YES |
| Benazeprilat | | YES | YES | YES | | YES |
| Betaxolol | YES | | YES | | | |
| Bicalutamide | YES | | YES | | | |
| Biotin | | YES | YES | YES | | YES |
| Biperiden | YES | | | | | |
| Bisoprolol | YES | | YES | | | |
| Bitolterol | YES | | YES | | | |
| Brinzolamide | | | YES | | YES | |
| Bupivacaine | | | YES | | | |
| Buprenorphine | YES | | | | | |
| Bupropion | | | YES | | | |
| Butorphanol | YES | | | | | |
| Capacitabine | | | YES | | | |
| Captopril | | YES | YES | YES | | YES |
| Carbidopa | YES | YES | YES | YES | YES | YES |
| Carnitine | YES | YES | | YES | | YES |
| Carteolol | YES | | YES | | | |
| Cefditoren | | YES | YES | YES | YES | YES |
| Cerivastatin | YES | YES | | YES | | YES |
| Chloramphenicol | YES | | | | | |
| Cisapride | | | YES | | YES | |
| Clopidogrel Acid | | YES | | YES | | YES |
| Clorazepic Acid | | YES | YES | YES | | YES |
| Cycloserine | | | YES | | YES | |
| Cytarabine | YES | | YES | | YES | |
| Danazol | YES | | | | | |
| Dextroamphetamine | | YES | | YES | | |
| Didanosine | YES | | YES | | | |
| Digoxin | YES | | | | | |
| Divalproex | | YES | | YES | | YES |
| Docetaxel | YES | | YES | | | |
| Dorzolamide | | | YES | | YES | |
| Dyphylline | YES | | | | | |
| Dysopyramide | | | YES | | YES | |
| Efavirenz | | | YES | | | |
| Enalaprilat | | YES | YES | YES | | YES |
| Ephedrine | YES | | YES | | | |
| Eplerenone | | YES | | YES | | YES |
| Eprosartan | | YES | | YES | | YES |
| Esmolol | YES | | YES | | | |
| Estramustine | YES | | | | | |
| Ethambutol | YES | | YES | | | |
| Ethchlorvynol | YES | | | | | |
| Ethosuximide | | | YES | | | |
| Ethotoin | | | YES | | | |
| Etidocaine | | | YES | | | |
| Etoposide | YES | | | | | |
| Ezetimibe | YES | | | | | |
| Fenofibrate | | YES | | YES | | YES |
| Fenoprofen | | YES | | YES | | YES |
| Fexofenadine | YES | YES | | YES | | YES |
| Finasteride | | | YES | | | |
| Fluoxetine | | | YES | | | |
| Fluticasone | YES | | | | | |
| Fluvastatin | YES | YES | | YES | | YES |
| Folic Acid | | YES | YES | YES | YES | YES |
| Fosinoprilat | | YES | | YES | | |
| Frovatriptan | | | YES | | YES | |
| Fulvestrant | YES | | | | | |
| Gabapentin | | YES | YES | YES | YES | YES |
| Ganciclovir | YES | | | | | |
| Glimepiride | | | YES | | | |
| Goserelin | YES | | | | | |
| Hydroxychloroquine | YES | | | | | |
| Hydroxyzine | YES | | | | | |
| Hyoscyamine | YES | | | | | |
| Ibuprofen | | YES | | YES | | YES |
| Ibutilide | YES | | YES | | | |
| Indapamide | | | YES | | YES | |
| Indinavir | YES | | YES | | | |
| Ipratropium | YES | | | | | |
| Irinotecan | YES | | | | | |
| Isosorbide | YES | | | | | |
| Isradipine[2] | | | YES | | | |

-continued

| Drug | A | B | C | D | E | F |
|---|---|---|---|---|---|---|
| Ketoprofen | | YES | | YES | | YES |
| Ketorolac | | YES | | YES | | YES |
| Labetalol | YES | | YES | | | |
| Lamivudine | YES | | YES | | YES | |
| Lamivudine | YES | | YES | | YES | |
| Lansoprazole | | | YES | | | |
| Latanoprost Acid | YES | YES | | YES | | YES |
| Leuprolide | YES | | | | | |
| Levobunolol | YES | | YES | | YES | |
| Levodopa | YES | YES | YES | YES | YES | YES |
| Levorphanol | YES | | | | | |
| Liothyronine | YES | YES | YES | YES | YES | YES |
| Lisinopril | | YES | YES | YES | YES | YES |
| Lopinavir | YES | | YES | | | |
| Lorazepam | | | YES | | | |
| Lovastatin | YES | YES | | YES | | YES |
| Medroxyprogesterone | YES | | | | | |
| Mefloquine | YES | | YES | | | |
| Megestrol | YES | | | | | |
| Mephobarbital | | | YES | | | |
| Mepivacaine | | | YES | | | |
| Metaproterenol | YES | | YES | | | |
| Metformin | | | YES | | YES | |
| Methamphetamine | | | YES | | | |
| Methohexital | YES | | | | | |
| Methotrexate | | YES | | YES | | YES |
| Methylphenidate | | YES | YES | YES | | YES |
| Methylphenidate³ | | | YES | | | |
| Methylprednisolone | YES | | | | | |
| Metolazone | | | YES | | YES | |
| Metoprolol | YES | | YES | | | |
| Mexiletine | | | YES | | YES | |
| Miglitol | YES | | | | | |
| Miglitol | YES | | | | | |
| Moexiprilat | | YES | YES | YES | | YES |
| Mometasone | YES | | | | | |
| Montelukast | YES | YES | | YES | | YES |
| Nadolol | YES | | YES | | | |
| Nalbuphine | YES | | | | | |
| Naproxen | | YES | | YES | | YES |
| Naratriptan | | | YES | | YES | |
| Nateglinide | | YES | YES | YES | | YES |
| Nelfinavir | YES | | YES | | | |
| Niacin | | YES | | YES | | YES |
| Nicardipine⁴ | | | YES | | | |
| Nimidipine⁵ | | | YES | | | |
| Nisoldipine⁶ | | | YES | | | |
| Norgestimate | YES | | | | | |
| Octreotide | YES | | YES | | | |
| Ofloxacin | | YES | | YES | | YES |
| Olmesartan | | YES | | YES | | YES |
| Omeprazole | | | YES | | YES | |
| Paclitaxel | YES | | YES | | | |
| Pantothenic Acid | YES | YES | YES | YES | | YES |
| Paroxetine | | | YES | | YES | |
| Paroxetine | | | YES | | | |
| Pemoline | | | YES | | YES | |
| Penbutolol | YES | | YES | | | |
| Penicillamine | | YES | YES | YES | YES | YES |
| Pentazocine | YES | | | | | |
| Pentobarbital | | | YES | | | |
| Perindoprilat | | YES | YES | YES | | YES |
| Phenylephrine | YES | | YES | | | |
| Phenylpropanolamine | YES | | YES | | YES | |
| Pindolol | YES | | YES | | | |
| Pioglitazone | | | YES | | | |
| Pirbuterol | YES | | | | | |
| Pramipexole | | | YES | | YES | |
| Pravastatin | YES | YES | | YES | | YES |
| Propafenone | YES | | YES | | | |
| Propranolol | YES | | YES | | | |
| Pseudoephedrine | YES | | YES | | | |
| Quinacrine | | | YES | | | |
| Quinaprilat | | YES | YES | YES | | YES |
| Quinethazone | | | YES | | YES | |
| Quinidine | YES | | | | | |
| Quinine | YES | | | | | |
| Ramiprilat | | YES | YES | YES | | YES |
| Reboxetine | | | YES | | | |
| Repaglinide | | YES | YES | YES | | YES |
| Repaglinide | | YES | YES | YES | YES | YES |
| Ribavirin | YES | | YES | | YES | |
| Ritonavir | YES | | YES | | | |
| Ropivacaine | | | YES | | | |
| Rosiglitazone | | | YES | | | |
| Rosuvastatin | YES | YES | | YES | | YES |
| Salmeterol | YES | | YES | | | |
| Sertraline | | | YES | | | |
| Simavastatin | YES | YES | | YES | | YES |
| Sirolimus | YES | | | | | |
| Sotalol | YES | | YES | | | |
| Sulfa Drugs | | | YES | | YES | |
| Sulfasalazine | | | | | YES | |
| Sumitriptan | | | YES | | YES | |
| Tacrolimus | YES | | | | | |
| Tazorotene | | YES | | YES | | YES |
| Telmesartan | | YES | | YES | | YES |
| Tenofovir | YES | | | | | |
| Terbutaline | YES | | YES | | | |
| Thyroxine | | YES | YES | YES | YES | YES |
| Tiagabine | | YES | | YES | | YES |
| Timolol | YES | | YES | | | |
| Tirofiban | | YES | YES | YES | | YES |
| Tocainide | | | YES | | YES | |
| Tramadol | YES | | | | | |
| Trandolaprilat | | YES | YES | YES | | YES |
| Tranylcypromine | | | YES | | YES | |
| Treprostinil | YES | YES | | YES | | YES |
| Triamcinolone | YES | | | | | |
| Troglitazone | YES | | YES | | | |
| Unoprostone | | YES | | YES | | YES |
| Valsartan | | YES | | YES | | YES |
| Venlafaxine | YES | | | | | |
| Vidarabine | YES | | YES | | YES | |
| Warfarin | YES | | | | | |
| Zalcitabine | YES | | YES | | YES | |
| Zidovudine | YES | | YES | | | |
| Zolmitriptan | | | YES | | YES | |

¹In case of Amlodipine, one can replace 5-methyl ester moiety with 3-L-Threonine with better therapeutic index. In case of intact Amlodipine molecule, biotransformation results in generation of methanol due to solvolysis of 5-methyl ester, which is highly toxic, and replacement of this with L-Threonine results in a product with much less toxicity. Same argument goes for rest of the products in this category stated below:
²For Isradipine, replace 5 methyl ester with 5-L-Threonine ester. The methyl ester is the active, and apparently the carboxylic acid derivative is not active.
³Replacing the methyl group with L-Threonine will still maintain activity, but none of the toxicity of methylphenidate.
⁴For Nicardipine, replace 5-methyl ester with 5-L-Threonine for better therapeutic index.
⁵For Nimodipine, one could replace 5 (1-methyl)ethyl ester with 5-L-Threonine for better therapeutic index.
⁶In case of Nisoldipine, replace 5-methyl ester with 5-L-Threonine for better therapeutic index, and no loss of activity.

It is to be understood that the base structure of each of the drugs enumerated herein is incorporated by reference. Moreover, the products thereof, although not drawn, are understood by one of ordinary skill in the art, based upon the reaction schemes described hereinabove and are considered as part of this disclosure.

The derivatives of the present invention may be L-Threonine esters/amides/anhydrides and azo derivatives. The L-Threonine derivatives are capable of forming a wide variety of pharmaceutically acceptable salts with various inorganic and organic acids. These acids that may be used to prepare pharmaceutically acceptable acid addition salts of such basic compounds are those that form non-toxic acid addition salts, i.e., salts containing pharmaceutically acceptable anions, such as the hydrochloride, hydrobromide, hydroiodide, nitride, sulfate, bisulfate, phosphate, formate, acetate, citrate, tartate, lactate, and the like.

As indicated herein, in one embodiment, the present invention is directed to a derivative wherein the derivative comprises a drug, e.g., Ibuprofen and the amino acid L-Threonine esterified to the —COOH group of Ibuprofen. This results in a derivative where L-Threonine is attached to the Ibuprofen, for example, by a covalent bond.

The compounds of the present invention are prepared by art recognized techniques. For examples, if the drug contains an OH group, said as hydroxychloroquine, then the carboxyl group of L-Threonine is reacted to form a covalent bond, resulting in an ester or the hydroxy group may be oxidized to an acid and the covalent bond may be formed between the carboxy group thus formed and the OH group of the hydroxychloroquine. The former, however, is preferred. Alternatively, as described hereinabove, if the drug has an amino group thereon, then the L-Threonine may be reacted through the carboxy group of the Threonine with the drug under amide forming conditions to form an amide as the covalent bond, or the hydroxy group of the side chain may be oxidized to a carboxy group and the amide bond is through the carboxy group of the oxidized hydroxy group of the side chain, although, the former is preferred. Alternatively, if the drug has a carboxy group or acylating derivative thereon, it may be reacted with the amino group of the L-Threonine to form an amide under amide forming conditions or the OH group of the side chain of Threonine may be converted to the $NH_2$ group and this amino group may form an amide bond with the carboxy group or acylating derivative of the drug, but again the former is preferred. Additionally if the drug has a carboxy group thereon, the hydroxy group of the side chain of the L-Threonine may be reacted with the carboxy group or acylating derivative, thereof under esterification conditions to form the ester linkage between the L-Threonine and the drug, as described hereinabove.

If any portion of the L-Threonine group or the drug is reactive under the reaction conditions, it is protected by a protecting group known in the art. After the completion of the reaction, the protecting group is removed. Examples of protecting groups that could be used are described in the book entitled, "Protective Group in Organic Synthesis" by Theodora W. Greene, John Wiley & Sons, 1981, the contents of which are incorporated by reference.

For example, if L-Threonine is to be reacted with a drug containing COOH group to form the ester, then the COOH group of L-Threonine requires protection using protecting groups known in the art. Examples of suitable protecting groups can be esters, such as cyclohexyl esters, t-butyl esters, benzyl esters, allyl esters, 9-fluorophenyl-methyl groups or adamantyl groups, such as 1- or 2-adamantyl which can be removed after the esterfication reaction is completed using techniques known to one of ordinary skill in the art.

If the L-Threonines hydroxyl group is to be protected in a reaction between L-Threonine and a drug containing OH group, then the OH group of L-Threonine is protected with protecting groups known in the art, e.g., ethers, such as benzyl ether or t-butyl ether. Removal of the benzyl ether can be effected by liquid hydrogen fluoride, while the t-butyl ether can be removed by treatment with trifluoroacetic acid. Suitable protecting groups for phenolic side chain groups can be ethers, as above, including benzyl or t-butyl ether or 2,6-dichlorobenzyl, 2-bromobenzyloxycarbonyl, 2,4-dintrophenyl and the like.

Moreover, the products prepared by the present invention can be purified to be made substantially pure by techniques known to one of ordinary skill in the art, such as by chromatography, e.g., HPLC, crystallization and the like. By substantially "pure" it is meant that the product contains no more than about 10% impurity therein (w/w). Further, the products can be prepared to be made substantially sterochemically pure using techniques known to one of ordinary skill in the art. By "stereochemically pure" it is meant that the product contains no more than 10% by weight of the enantiomer, disasteromer or other stereoisomer.

The drugs to which the L-Threonine moiety is covalently bonded (hereinafter "derivatives of the present invention"), or pharmaceutical acceptable salts, pharmaceutical acceptable solvates, esters, enantiomers, diastereomers, N-Oxides, polymorphs, and the like, as described herein, can be made into pharmaceutical compositions along with a pharmaceutical acceptable carrier, and optionally but desirably pharmaceutically acceptable excipients using techniques known to one of ordinary skill in the art.

The pharmaceutical compositions of the present invention are used in therapeutically effective amounts.

The physician will determine the dosage of the derivatives of the present invention which will be most suitable and it will vary with the form of administration and the particular compound chosen, and furthermore, it will vary depending upon various factors, including but not limited to, the patient under treatment and the age of the patient, the severity of the condition being treated and the like and the identity of the derivative of the present invention administered. He will generally wish to initiate treatment with small dosages substantially less than the optimum dose of the derivative of the present invention and increase the dosage by small increments until the optimum effect under the circumstances is reached. It will generally be found that when the composition is administered orally, larger quantities of the active agent will be required to produce the same effect as a smaller quantity given parenterally. The compounds of the present invention are useful in the same manner as the corresponding drug from which they are prepared, and the dosage level is preferably of the same order of magnitude as is generally employed with these other therapeutic agents. When given parenterally, the compounds are administered generally in dosages of, for example, about 0.00001 to about 10,000 mg/kg/day, also depending upon the host and the severity of the condition being treated and the compound of the present invention utilized.

In a preferred embodiment, the compounds of the present invention utilized are orally administered in amounts ranging from about 0.0001 mg to about 1000 mg per kilogram of body weight per day, depending upon the particular mammalian host or the disease to be treated, more preferably from about 0.01 to about 500 mg/kg body weight per day. This dosage regimen may be adjusted by the physician to provide the optimum therapeutic response. For example, several divided doses may be administered daily or the dose may be proportionally reduced as indicated by the exigencies of the therapeutic situation.

The derivative of the present invention may be administered in any convenient manner, such as by oral, intravenous, intramuscular or subcutaneous, transdermal, rectal, vaginal, buccal, nasal routes and the like.

The derivative of the present invention may be orally administered, for example, with an inert diluent or with an assimilable edible carrier, or it may be enclosed in hard or soft shell gelatin capsules, or it may be compressed into tablets, or it may be incorporated directly into the food of the diet. For oral therapeutic administration, the derivative of the present invention may be incorporated with excipients and used in the form of ingestible tablets, buccal tablets, troches, capsules, elixirs, suspensions, syrups, wafers, and the like. Such compositions and preparations should contain at least 0.0001% of the derivative of the present invention. The percentage of the compositions and preparations may, of course, be varied and may conveniently be between about 0.001 to about 99.9999% of the weight of the unit. The amount of the derivative of the present invention used in such therapeutic compositions is such that a suitable dosage will be obtained. Preferred compositions or preparations according to the present invention contain between about 0.0001 mg and about 4000 gm of derivative. The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier.

Various other materials may be present as coatings or otherwise modify the physical form of the dosage unit. For instance, tablets, pills, or capsules may be coated with shellac, sugar or both. A syrup or elixir may contain the compound of the present invention, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the compound of the present invention may be incorporated into sustained-release preparations and formulations. For example, sustained release dosage forms are contemplated wherein the compound of the present invention is bound to an ion exchange resin which, optionally, can be coated with a diffusion barrier coating to modify the release properties of the resin or wherein the compound of the present invention is associated with a sustained release polymer known in the art, such as hydroxypropylmethylcellulose and the like.

The compound of the present invention may also be administered parenterally or intraperitoneally. It is especially advantageous to formulate parenteral compositions in dosage unit form for ease of administration and uniformity of dosage. Dispersions can also be prepared in glycerol, liquid polyethylene glycols, e.g., PEG 100, PEG 200, PEG 300, PEG 400, and the like, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersions. In all cases the form is usually sterile and must be fluid to the extent that syringability exists. It must be stable under the conditions of manufacture and storage and usually must be preserved against the contaminating action of microorganisms such as bacteria and fungi. The carrier can be a solvent or dispersion medium containing, for example, water, ethanol, polyol (for example, glycerol, propylene glycol, and one or more liquid polyethylene glycol, e.g. as disclosed herein and the like), suitable mixtures thereof, and vegetable oils. The proper fluidity can be maintained, for example, by the use of a coating such as lecithin, by the maintenance of the required particle size in the case of dispersions and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the compound of the present invention in the required amount in the appropriate solvent with various of the other ingredients enumerated above, as required, followed by filtered sterilization. Generally, dispersions are prepared by incorporating the sterilized compound of the present invention into a sterile vehicle which contains the basic dispersion medium and the required other ingredients from those enumerated above. In the case of sterile powders, the above solutions are vacuum dried or freeze-dried, as necessary.

The compound of the present invention can also be applied topically, as e.g., through a patch using techniques known to one of ordinary skill in the art. It can be administered buccally by preparing a suitable formulation thereof and utilizing procedures well known to those skilled in the art. These formulations are prepared with suitable non-toxic pharmaceutically acceptable ingredients. These ingredients are known to those skilled in the preparation of buccal dosage forms. Some of these ingredients can be found in Remington's Pharmaceutical Sciences, $17^{th}$ edition, 1985, a standard reference in the field. The choice of suitable carriers is highly dependent upon the exact nature of the buccal dosage form desired, e.g., tablets, lozenges, gels, patches and the like. All of these buccal dosage forms are contemplated to be within the scope of the present invention and they are formulated in a conventional manner.

The formulation of the pharmaceutical compositions of the present invention may be prepared using conventional methods using one or more physiologically and/or pharmaceutically acceptable carriers or excipients. Thus, the compounds of the present invention and their pharmaceutically acceptable salts and solvates may be formulated for administration by inhalation or insufflation (either through the mouth or the nose) or oral, buccal, parenteral, or rectal administration. For oral administration, the pharmaceutical compositions may take the form of, for example, tablets or capsules prepared by conventional means with pharmaceutically acceptable excipients such as binding agents (for example, pregelatinized maize starch, polyvinylpyrrolidone, or hydroxypropylmethyl cellulose); fillers (for example, lactose, microcrystalline cellulose or calcium hydrogen phosphate); lubricants (for example, magnesium stearate, talc, or silica); disintegrants (for example, potato starch, or sodium starch glycolate); or wetting agents (for example, sodium lauryl sulfate). The tablets may be coated by methods well known in the art.

Liquid preparations for oral administration may take the form of, for example, solutions, syrups, or suspensions, or they may be presented as a dry product for constitution with water or other suitable vehicles before use. Such liquid preparations may be prepared by conventional means with pharmaceutically acceptable additives, such as suspending agents (for example, sorbitol syrup, corn syrup, cellulose derivatives or hydrogenated edible oils and fats); emulsifying agents (for example, lecithin or acacia); non-aqueous vehicles (for example, almond oil, oily esters, ethyl alcohol or fractionated vegetable oils); and preservatives (for example, methyl or propyl p-hydroxybenzoates or sorbic acid). The preparations may also contain buffer salts, flavoring, coloring and sweetening agents as appropriate. Preparations for oral administration may be suitably formulated to give controlled release of the active derivative.

The derivative of the present invention may be formulated for parenteral administration by injection, for example, by bolus injection or continuous infusion. Formulations for injection may be presented in unit dosage form, for example, in ampoules, or in multi-dose containers, with an added preservative. The compositions of the present invention may take such forms as suspension, solutions or emulsions in oily or aqueous vehicles, and may contain formulatory agents such as suspending, stabilizing and/or dispersing agents. Alternatively, the derivative of the present invention may be in the powder form for constitution with a suitable vehicle, for example, sterile pyrogen-free water, before use.

The derivatives of the present invention may also be formulated in rectal compositions such as suppositories or retention enemas, for example, containing conventional suppository bases such as cocoa butter or other glycerides.

In addition to the formulations described previously, the derivative of the present invention may also be formulated as a depot preparation. Such long acting formulations may be administered by implantation (for example, subcutaneously or intramuscularly) or by intramuscular injection. Thus, for example, the derivatives of the present invention may be formulated with suitable polymeric or hydrophobic materials (for example, as an emulsion in an acceptable oil) or ion exchange resins, or as sparingly soluble derivatives, for example, as a sparingly soluble salt.

The pharmaceutical compositions containing the derivatives of the present invention may, if desired, be presented in a pack or dispenser device which may contain one or more unit dosage forms containing the active ingredients. The pack may for example comprise metal or plastic foil, such as blister pack. The pack or dispenser device may be accompanied by instructions for administration.

In tablet form, it is desirable to include a lubricant which facilitates the process of manufacturing the dosage units; lubricants may also optimize erosion rate and drug flux. If a lubricant is present, it will be present on the order of 0.01 wt. % to about 2 wt. %, preferably about 0.01 wt. % to 0.5 wt, %, of the dosage unit. Suitable lubricants include, but are not limited to, magnesium stearate, calcium stearate, stearic acid, sodium stearylfumarate, talc, hydrogenated vegetable oils and polyethylene glycol. As will be appreciated by those skilled in the art, however, modulating the particle size of the components in the dosage unit and/or the density of the unit can provide a similar effect—i.e., improved manufacturability and optimization of erosion rate and drug flux—without addition of a lubricant.

Other components may also optionally be incorporated into the dosage unit. Such additional optional components include, for example, one or more disintegrants, diluents, binders, enhancers, or the like. Examples of disintegrants that may be used include, but are not limited to, crosslinked polyvinylpyrrolidones, such as crospovidone (e.g., Polyplasdone® XL, which may be obtained from GAF), cross-linked carboxylic methylcelluloses, such as croscanmelose (e.g., Ac-Di-Sol®, which may be obtained from FMC), alginic acid, and sodium carboxymethyl starches (e.g., Explotab®, which may be obtained from Edward Medell Co., Inc.), agar bentonite and alginic acid. Suitable diluents are those which are generally useful in pharmaceutical formulations prepared using compression techniques, e.g., dicalcium phosphate dihydrate (e.g., Di-Tab®, which may be obtained from Stauffer), sugars that have been processed by crystallization with dextrin (e.g., co-crystallized sucrose and dextrin such as Di-Pak®, which may be obtained from Amstar), calcium phosphate, cellulose, kaolin, mannitol, sodium chloride, dry starch, powdered sugar and the like. Binders, if used, are those that enhance adhesion. Examples of such binders include, but are not limited to, starch, gelatin and sugars such as sucrose, dextrose, molasses, and lactose. Permeation enhancers may also be present in the novel dosage units in order to increase the rate at which the active agents pass through the buccal mucosa. Examples of permeation enhancers include, but are not limited to, dimethylsulfoxide ("DMSO"), dimethyl formamide ("DMF"), N,N-dimethylacetamide ("DMA"), decylmethylsulfoxide ("$C_{10}$MSO"), polyethylene glycol monolaurate ("PEGML"), glycerol monolaurate, lecithin, the 1-substituted azacycloheptan-2-ones, particularly 1-n-dodecylcyclazacycloheptan-2-one (available under the trademark Azone® from Nelson Research & Development Co., Irvine, Calif.), lower alkanols (e.g., ethanol), SEPA® (available from Macrochem Co., Lexington, Mass.), cholic acid, taurocholic acid, bile salt type enhancers, and surfactants such as Tergitol®, Nonoxynol-9® and TWEEN-80®.

Flavorings may be optionally included in the various pharmaceutical formulations. Any suitable flavoring may be used, e.g., mannitol, lactose or artificial sweeteners such as aspartame. Coloring agents may be added, although again, such agents are not required. Examples of coloring agents include any of the water soluble FD&C dyes, mixtures of the same, or their corresponding lakes.

In addition, if desired, the present dosage units may be formulated with one or more preservatives or bacteriostatic agents, e.g., methyl hydroxybenzoate, propyl hydroxybenzoate, chlorocresol, benzalkonium chloride, or the like.

As used herein, "pharmaceutically acceptable carrier" includes any and all solvents, dispersion media, coatings, antibacterial and antifungal agents, isotonic and absorption delaying agents for pharmaceutical active substances well known in the art. Except insofar as any conventional media or agent is incompatible with the derivative, their use in the therapeutic compositions is contemplated. Supplementary active ingredients can also be incorporated into the compositions.

Dosage unit form as used herein refers to physically discrete units suited as unitary dosages for the subjects to be treated; each unit containing a predetermined quantity of derivative calculated to produce the desired therapeutic effect in association with the required pharmaceutical carrier.

The derivative of the present invention is compounded for convenient and effective administration in effective amounts with a suitable pharmaceutically acceptable carrier in dosage unit form as hereinbefore described. A unit dosage, for example, contains the compound of the present invention in effective amounts. For example, in a preferred embodiment, the amounts range from about 10 mg, e.g. in humans, or as low as 1 mg (for small animals) to about 2000 mg. If placed in solution, the concentration of the derivative of the present invention preferably ranges from about 10 mg/mL to about 250 mg/mL. In the case of compositions containing supplementary active ingredients, the dosages are determined by reference to the usual dose and manner of administration of the said ingredients. In the case of buccal administration, the derivatives of the present invention are preferably in the buccal unit dosage form present in an amount ranging from about 10 to about 50 mg.

The derivatives of the present invention are effective in treating disease or conditions in which the corresponding drug (without the L-Threonine derivative of the present invention) normally are used.

As used herein the term "treating" refers to reversing, alleviating or inhibiting the progress of a disease, disorder or condition, or one or more symptoms of such disease, disorder or condition, to which such term applies. As used herein, "treating" may also refer to decreasing the probability or incidence of the occurrence of a disease, disorder or condition in a mammal as compared to an untreated control population, or as compared to the same mammal prior to treatment. For example, as used herein, "treating" may refer to preventing a disease, disorder or condition, and may include delaying or preventing the onset of a disease, disorder or condition, or delaying or preventing the symptoms associated with a disease, disorder or condition. As used herein, "treating" may also refer to reducing the severity of a disease, disorder or condition or symptoms associated with such disease, disorder or condition prior to a mammal's affliction with the disease, disorder or condition. Such prevention or reduction of the severity of a disease, disorder or condition prior to affliction relates to the administration of the composition of the present invention, as described herein, to a subject that is not at the time of administration afflicted with the disease, disorder or condition. As used herein "treating" may also refer to preventing the recurrence of a disease, disorder or condition or of one or more symptoms associated with such disease, disorder or condition. The terms "treatment" and "therapeutically," as used herein, refer to the act of treating, as "treating" is defined above.

Prophylaxis or preventing or any like term, refers to decreasing the probability or incidence of the occurrence of a disease, disorder or condition in a mammal. It also includes delaying or preventing the onset of a disease, disorder or condition or delaying the symptoms associated with a disease, disorder or condition. In addition, it also refers to retarding the occurrence of a disease, disorder or condition in a mammal.

As used herein the term "patient" or "subject" refers to a warm blooded animal, and preferably mammals, such as, for example, cats, dogs, horses, cows, pigs, mice, rats and primates, including humans. The preferred patient is humans.

The derivatives of the present invention exhibit the same utility as the corresponding drug without the L-Threonine linkage. The derivative exhibits an enhanced therapeutic quality. That is, they exhibit at least one and more preferably at least two enhanced therapeutic qualities relative to the drug which has not been transformed to the derivative of the present invention prior to administration. These include, but are not limited to a. Improved taste, smell
b. Desired octanol/water partition coefficient (i.e., solubility in water/fat) The L-Threonine when covalently bound to a drug may enhance solubility in water or it may enhance absorption by the mammal to which it is administered.
c. Improved stability in-vitro and in-vivo
d. Enhanced penetration of blood-brain barrier
e. Elimination of first-pass effect in liver, i.e., the drug is not metabolized in the liver and therefore more drug in system circulation
f. Reduction of entero-hepatic recirculation (this improves bio-availability)
g. Painless injections with parenteral formulations
h. Improved bio-availability
i. Improved changes in the rate of absorption (increase vs lack thereof)
j. Reduced side effects
k. Dose proportionality
l. Selective hydrolysis of the derivative at site of action
m. Controlled release properties
n. Targeted drug delivery
o. Reduction in toxicity, hence, improved therapeutic ratio
p. Reduced dose
q. Alteration of metabolic pathway to deliver more drug at the site of action
r. Increased solubility in aqueous solution
s. Enhanced efficacy
t. Separation of enantiomers and diasteroisomers A dose proportionality claim requires that when the drug is administered in escalating doses, proportionally escalating amounts of active drug is delivered into the blood stream. This is measured by determining the area under the plasma concentration vs. time curve obtained after administering a drug via any route other than IV route and measuring the same in plasma/blood. A simple mathematical procedure is as follows: For example, a drug is administered at e.g., 3 different doses, 10, 100 and 1000 mg, orally to a patient, the area under the plasma concentration time curve (AUC) is measured. Then each total AUC is divided by the dose, and the result should be the same for all three doses. If it is the case, then there is dose proportionality. Lack of dose proportionality indicates any one or more of the pharmacokinetic/pharmacological mechanisms are saturable, including absorption, metabolism or the number of receptor sites available for pharmacological response.

For example in the above study, assume the AUC values of 100, 1000 and 10,000 are obtained, in this case the dose proportionality is inappropriate. When there is lack of dose proportionality, there is either more or less amount of drug in the plasma, depending upon which mechanism is saturable. The following are the possibilities:

Saturable Absorption. If this is the case, as the dose is increased, proportionally less and less of the drug is absorbed, hence overall AUC will decrease as the dose is increased.

Saturable metabolism of elimination. If this is the case, then more and more of the drug will be circulating in the blood, and the AUC will increase with increasing dose.

Saturable pharmacological receptor sites: In this case, since all the receptor sites will eventually be occupied by the drug, any additional drug will not increase the response, but most likely increase the toxicity of the drug/derivative. Thus, increasing dose will not result in increasing response and in fact may reduce the therapeutic index.

Dose proportionality is an excellent response profile, since one can predict accurately the pharmacological response and curative power at all doses. Thus dose proportionality is a desirable quality for any drug. Furthermore, achievement of dose proportionality is also dependent upon the formulation, and fed/fasted differences.

Thus, various dosage forms are available of drugs for which the L-Threonine is bound and they are prepared by conventional methods. These various dosage forms include:

i. Oral liquid dosage (Controlled release and immediate release liquids containing sugar and sugar free, dye and dye free, alcohol and alcohol free formulations, including chewable tablets)
ii. Oral solid dosage (Controlled release and immediate release tablets, capsules and caplets
iii. Intravenous (Injections, both ready to use and lyophilized powders)
iv. Intramuscular (Injections, both ready to use and lyophilized powders)
v. Subcutaneous (Injections, both ready to use and lyophilized powders)
vi. Transdermal (Mainly patches)
vii. Nasal (Sprays, formulations for nebulizer treatments)
viii. Topical (Creams, ointments)
ix. Rectal (Creams, ointments and suppositories)
x. Vaginal (Creams, ointments and pessaries)
xi. Ocular (Drops and ointments)
xii. Buccal (Chewable and now chewable tables)

Many drugs discussed herein, especially in the table hereinbelow are characteristically highly hydrophobic and readily precipitate in the presence of even very minor amounts of water, e.g., on contact with the body (e.g., stomach fluids). It is accordingly extremely difficult to provide e.g., oral formulations which are acceptable to the patient in terms of form and taste, which are stable on storage and which can be administered on a regular basis to provide suitable and controlling patient dosing.

Proposed liquid formulations, e.g., for oral administration of a number of drugs shown herein in the table have heretofore been based primarily on the use of ethanol and oils or similar excipient as carrier media. Thus, the commercially available drink-solutions of a number of drugs employ ethanol and olive oil or corn oil as carrier medium in conjunction with solvent systems comprising e.g., ethanol and LABRIFIL and equivalent excipient as carrier media. Use of the drink solution and similar composition as proposed in the art is, however, accompanied by a variety of difficulties.

Further, the palatability of the known oil based system has proved problematic. The taste of the known drink-solution of several drugs is, in particular, unpleasant. Admixture with an appropriate flavored drink, for example, chocolate drink preparation, at high dilution immediately prior to ingestion has generally been practiced in order to make regular therapy at all acceptable. Adoption of oil-based systems has also required the use of high ethanol concentrations which is itself inherently undesirable, in particular where administration to children is foreseen. In addition, evaporation of the ethanol, e.g., from capsules (adopted in large part, to meet problems of palatability, as discussed or other forms (e.g., when opened)) results in the development of drug precipitates. Where such compositions are presented in, for example, soft gelatin encapsulated form, the encapsulated product is packaged in an air-tight component, for example, an air-tight blister or aluminum-foil blister package. This in turn renders the product both bulky and more expensive to produce. The storage characteristics of the aforesaid formulations are, in addition, far from ideal.

Bioavailability levels achieved using existing oral dosage system for a number of drugs are also low and exhibit wide variation between individuals, individual patient types and even for single individuals at different times during the course of therapy. Reports in the literature indicate that currently available therapy employing the commercially available drug drink solution provides an average absolute bioavailability of approximately 10-30% only, with the marked variation between individual groups, e.g., between liver (relatively low bioavailability) and bone-marrow (relatively high bioavailability) transplant recipients. Reported variation in bioavailability between subjects has varied from one or a few percent for some patients, to as much as 90% or more for others. And as already noted, marked change in bioavailability for individuals with time is frequently observed. Thus, there is a need for a more uniform and high bioavailability of a number drugs shown herein in patients.

Use of such dosage forms is also characterized by extreme variation in required patient dosing. To achieve effective therapy, drug blood or blood serum levels have to be maintained within a specified range. This required range can, in turn, vary, depending on the particular condition being treated, e.g., whether therapy is to prevent one or more pharmacological actions of a specific drug and when alternative therapy is employed concomitantly with principal therapy. Because of the wide variations in bioavailability levels achieved with conventional dosage forms, daily dosages needed to achieve required blood serum levels will also vary considerably from individual to individual and even for a single individual. For this reason it may be necessary to monitor blood/blood-serum levels of patients receiving drug therapy at regular and frequent intervals. This is inevitably time consuming and inconvenient and adds substantially to the overall cost of therapy.

It is also the case that blood/blood serum levels of a number of drugs using available dosage systems exhibit extreme variation between peak and trough levels. That is, for each patient, effective drug levels in the blood vary widely between administrations of individual dosages.

Beyond all these very evident practical difficulties lies the occurrence of undesirable side reactions already alluded to, observed employing available oral dosage forms.

Several proposals to meet these various problems have been suggested in the art, including both solid and liquid oral dosage forms. An overriding difficulty which has however remained is the inherent insolubility of the several of the drugs without the Threonine attached thereto in aqueous media, hence preventing the use of a dosage form which can contain the drugs in sufficiently high concentration to permit convenient use and yet meet the required criteria in terms of bioavailability, e.g. enabling effective absorption from the stomach or gut lumen and achievement of consistent and appropriately high blood/blood-serum levels.

However, the compounds of the present inventions overcome the problems enumerated hereinabove.

For example, the derivative of the present invention significantly enhances the solubility of the drug from which it is synthesized in aqueous solutions relative to the non-derivative feint of the pharmaceutical, thereby avoiding the need to utilize a carrier, such as ethanol or castor oil when administered as a solution. Moreover, the derivatives of the present invention do not exhibit the side effects of the prior art formulations. Further, it has been found that when many of the drugs are administered covalently bound to threonine, in accordance with the present invention, there is enhanced oral absorption, thereby enhancing significantly its bioavailability and its efficacy.

The utility of the derivative is the same as the corresponding drug (without the L-Threonine moiety attached). The utility is described in the literature such as the Physicians Desk Reference, 2004 edition, the contents of which are incorporated by reference.

Enantiomeric or Stereoisomeric Separation Using L-Threonine

In a separate embodiment, it has been surprisingly found that L-Threonine can separate racemic mixtures of drug molecules into their pure enantiomers. Normally such separations are effected with heroic methods of synthesis, chromatography, fermentation with microbes, or using special bioenzymes. However, the present inventor has found that when the racemate drug was reacted with L-Threonine to form an ester, the two enantiomeric esters had different physicochemical characteristics. For example, one enantiomeric ester was more soluble in water and vice versa, hence the inventor could readily separate the two enantiomeric L-threonine drug esters.

Even more surprisingly, the inventor noted that only L-Threonine can separate the racemic mixtures of the drugs, and similar OH containing other amino acids such as L-Serine, L-hydroxyproline or other hydroxylamino acids did not have the same effectiveness as L-Threonine. Other than L-Threonine, none of the other hydroxyl amino acids were capable of readily separating the drug enantiomers to the same degree with minimal effort.

It was even more surprising, that when an ester of L-Threonine was made with a drug containing either OH or COOH group, the resulting ester not only resolved the chiral centers, but also the resulting drug ester was more effective in almost all cases than the intact drug. This was evident with racemic drugs such as ibuprofen and Ketorolac, and non-racemic drugs such as Aspirin, enalapril and Fenofibric acid.

Furthermore, it was highly surprising, that the resulting L-Threonine ester of the drugs did not act as a prodrug. One who is reasonably trained in the art for forming prodrugs and prodrug esters would have thought that an ester would be a prodrug and will release the active drug during its transport through the body, either at the site of oral absorption, GI wall, blood, liver or other organs of the body. But to the inventor's surprise, in many cases, there was no active drug in the blood stream after oral administration of the L-Threonine ester of the drug. In other words, the derivative of the present invention in which the L-Threonine is covalently bound to the drug, in many cases, are not prodrugs.

For example, the inventor noted that in case of Ibuprofen and Aspirin Threonine Esters, there was practically no Ibuprofen or Aspirin found in the blood stream of human subjects after oral administration of the respective ester. Surprisingly, the inventor noted that, not only was the parent drug not being released in the blood stream, but also the Threonine ester of the active drug exhibited better efficacy than the parent drug in all animal models and human trials.

It was also quite surprising that improved efficacy and enantiomeric separation with Threonine was non-specific to the drugs to which L-Threonine was attached. For example, drugs with quite widely varying chemical structures with differing polarities, molecular weights, therapeutic categories, molecular formula, active groups, active site and active moiety, and drugs with highly dissimilar drug-receptor topography were able to react with L-Threonine and resulted in improved therapeutic index.

Moreover, the inventor has also found that the drug to which the Threonine was bound is less toxic. For example, Ibuprofen racemic mixture was more toxic to rats under chronic administration. 40% of the rats receiving Ibuprofen racemic mixture died during the 28-day chronic toxicity study. However, all the animals receiving L-Threonine ester of Ibuprofen survived and appeared healthy in the same parallel trial, but had somewhat reduced body weight.

Similar results in toxicity were seen with Aspirin. When the L-Threonine ester of Aspirin was administered orally to rats, no GI side effects were seen, however, with intact aspirin, severe GI anatomical changes, bleeding, ulcers and other side effects were noted in the same group of rats.

While the L-Threonine ester had better pharmacological profile than the parent drug, and it was able to separate the racemic mixtures into their pure enantiomers, the inventor surprisingly found that such effects were repeated again and again with various other drugs.

For example, the inventor found that L-Threonine also separated Ketoprofen, while none of the other OH containing amino acids such as Hydroxyproline or Serine were unable to separate the enantiomers as readily as Threonine did. Without employing any heroic methods, the separation of the enantiomers of the L-Threonine ester of Ketoprofen was easily achieved. Furthermore, the inventor also noted that L-Threonine separated the racemic mixture of Ketorolac into its enantiomerically and stereochemically pure isomers as well.

Thus, L-threonine is an important agent in the separation of enantiomers and diasetereoisomers. It was possible to simply hydrolyze the L-threonine ester of Ibuprofen into either S(+) or R(−) ibuprofen, rather readily with usual organic reaction methods. Similarly the inventor was able to hydrolyze the L-Threonine esters of Ketoprofen and Ketorolac to release the pure enantiomers.

Moreover, the inventor has found that the resulting L-Threonine esters of the individual enantiomers are more active, and less toxic, resulting in improved therapeutic efficacy.

Such improved therapeutic efficacy is not only related to isolating the right isomer, but the inventor has also found that this is true in case of other drugs that are not racemates or stereoisomers. For example, the inventor noted that non-racemates such as Aspirin, Fenofibric Acid, enalaprilat and other drugs were also of high therapeutic index or greater effiacy, when L-Threonine esters were formed with these drugs. The use of L-threonine was able to separate molecules of widely varying and dissimilar organic chemical structures. In those cases where issue of separation of enantiomers does not arise, derivatives of the present invention e.g., L-Threonine esters of achiral drugs showed better therapeutic qualities compared to their parent drugs.

Therefore the derivatives of the present invention for a number of drugs are not prodrugs, have intact activity, better efficacy and less toxicity, resulting in improved therapeutic index.

With respect to hydroxychloroquine, one enantiomer is active against *plasmodium vivax* parasite and the other isomer is active for its disease modifying effect for rheumatoid arthritis. However, it is postulated that only one of these isomer is responsible for optical retinopathy. Hence by administering the less toxic variety, by covalently bonding the L-Threonine moiety thereto by an ester linkage between the OH group of the hydroxychloroquine and the carboxy group of the Threonine the optical toxicity of hydroxychlorqouine is significantly reduced.

As an additional specific example of usefulness of L-threonine based separation of racemic mixture can be applied to carvedilol, with the following structure:

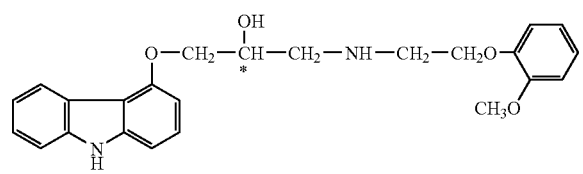

which is (±)-1-(Carbazol-4-yloxy)-3-[[2-(o-methoxyphenoxy)ethyl]amino]-2-propanol. Carvedilol is a racemic mixture in which nonselective β-adrenoreceptor blocking activity is present in the S(−) enantiomer and α-adrenergic blocking activity is present in both R(+) and S(−) enantiomers at equal potency. Carvedilol has no intrinsic sympathomimetic activity. However, this drug can be readily separated into its pure isomers, using L-threonine, by reacting the OH group with COOH of L-Threonine. This achieves the following results:
 a) When specific beta-adrenergic blocking action is required to reduce the blood pressure, one could administer S(−)Carvedilol-L-threonine ester.
 b) When specific alpha-1 adrenergic blocking activity is needed, it is preferable to administer R(+)Carvedilol-L-threonine ester. This is due to the fact that 3 times higher levels of R(+) is available in human plasma after oral administration compared to the S(−) variety due to first pass metabolism.

The following non-limiting examples further illustrate the invention:

Pure Enantiomeric L-Threonine Esters of Non-Steroidal Anti-Inflammatory Drugs (NSAIDs)

The NSAIDs comprise a class of structurally distinctive, carboxylic acid moiety attached to a planar aromatic functionality, Examples include: acetyl salicyclic acid, salicyclic acid, diflunisal, ibuprofen, fenoprofen, carprofen, flurbiprofen, ketoprofen, naproxen, sulindac, indomethacin, etodolac, tolmetin, ketorolac, diclofenac, and meclofenamate, and the like. The NSADIs posses anti-inflammatory, analgesic, antipyretic and anti-clotting activity.

Examples of the chemical structures of this unique class of compounds showing wide variety of pharmacological activities are shown below.

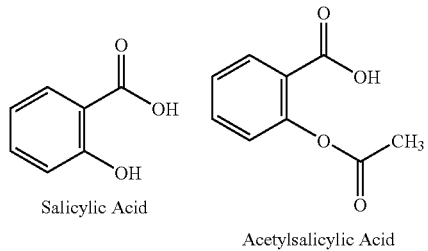

Salicylic Acid

Acetylsalicylic Acid

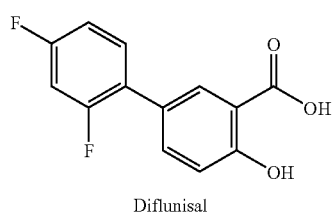

Diflunisal

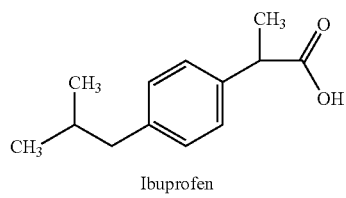

Ibuprofen

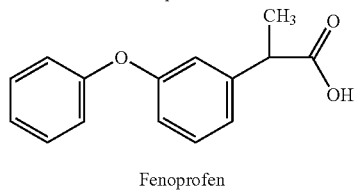

Fenoprofen

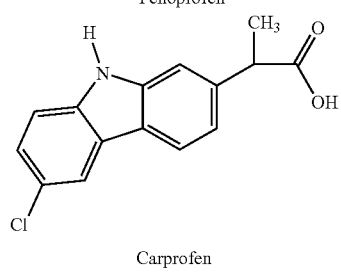

Carprofen

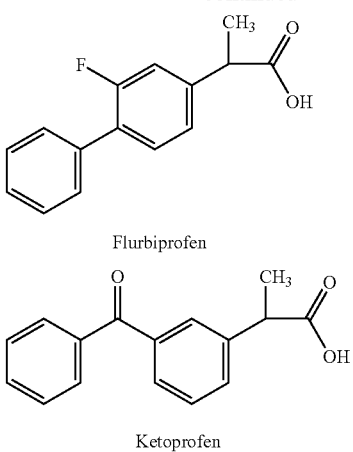

Flurbiprofen

Ketoprofen

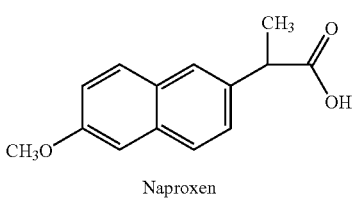

Naproxen

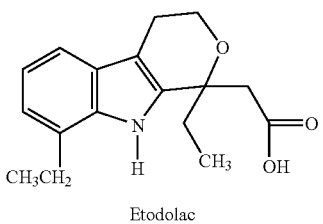

Etodolac

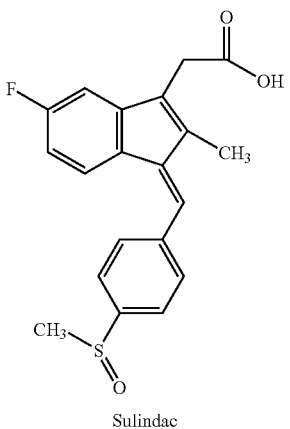

Sulindac

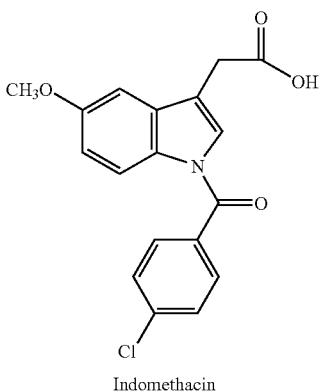

Indomethacin

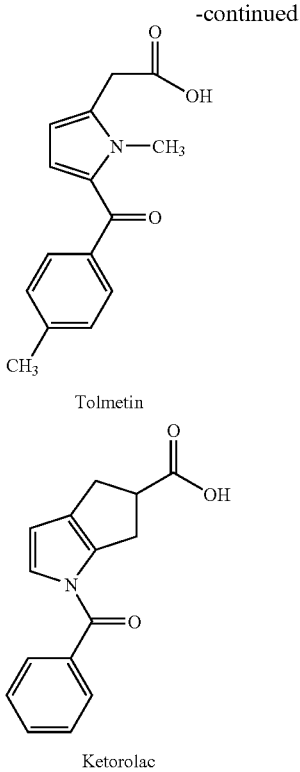

Tolmetin

Ketorolac

NSAIDs are widely used for the treatment of acute and chronic pain, management of edema, tissue damage resulting from inflammatory joint diseases and also, effective anti-clotting agents in the treatment of myocardial infraction. A number of the agents also possess antipyretic activity in addition to analgesic and anti-inflammatory action, thus useful in reducing fever.

Some drugs in the above group have also been prescribed for Rheumatoid Arthritis, Osteoarthritis, acute gout, ankolysing spondylitis, and dysmenorrhea.

Mechanism of Action:

The major mechanism by which the NSAIDs produce their therapeutic effect is via inhibition of prostaglandin synthesis. Specifically NSAIDs inhibit cyclooxygenases, such as COX-1 and COX-2 enzymes, where these two enzymes are responsible for synthesis of prostaglandins. While COX-1 enzyme is important for the regulation of platelet aggregation, regulation of blood flow in kidney and stomach, and regulation of gastric acid secretion, COX-2 enzyme plays an important role in the pain and inflammatory processes. NSAIDs significantly increase clotting time and can be used for the prophylaxis of thromboembolism and myocardial infarction.

All NSAIDs are relatively medium to strong organic acids with pKa's in the 3-6 range. Most of them are carboxylic acid derivatives. An acidic group is essential for COX inhibitory activity and in physiological pH, all the NSAIDs are ionized. All of them have quite varying hydrophilic lipophilic balance, and these are functions of their aryl, aromatic and aliphatic side chains and other heterocyclic variations in their structures. Most of the NSAIDs are highly bound to plasma proteins and often competitively replace other drugs which have similar affinity for plasma proteins. Hence concomitant administration of NSAIDs with another drug, e.g. another therapeutic class, must be carefully evaluated to prevent drug interactions. Most of the drugs, due to acidic carboxyl group are metabolized by the mammals via conjugation. The major pathway of metabolic clearance of a number of NSAIDs is glucuronidation followed by renal elimination.

Use of acetylsalicylic acid (aspirin) in the prophylaxis of coronary heart diseases is now well known, and this drug has proved to be a lifesaver for a number of patients with myocardial infarction. Several additional uses have already been documented for aspirin, for example, it was recently reported in the medical journal Lancet (Vol 349, p 1641) that aspirin reduces the risk of stroke in patients with early warning signs of transient ischemic heart attacks. Pre-eclampsia and fetal growth retardation, both caused by blockages of the blood vessels of the placenta, are two of the commonest complications of pregnancy—there are millions of cases of pre-eclampsia in the world each year. In a trial involving more than 9000 women in 16 countries, a daily dose of 60 mg aspirin reduced the risk of pre-eclampsia by 13 percent. (Aspirin Foundation website). Aspirin has also been shown to be effective in some studies to prevent colon cancer, lung cancer and pancreatic cancer in post-menopausal women. Since aspirin can improve blood flow, its usefulness in the treatment of diabetes and certain forms of dementia such as Alzheimer's disease are becoming increasingly clear.

Because of their unique pharmaceutical potential, the NSAIDs have attracted considerable attention in the press. The primary area of clinical investigation for these drugs has been as non-steroidal anti-inflammatory agents, in particular in relation to their application to patients suffering from pain, arthritis (Rheumatoid and Osteo), other inflammatory reactions, and fever and for the prophylaxis of coronary heart diseases. These drugs are also used in the treatment of migraine headache, menstrual syndromes, back pain and gout.

Even more troubling health care issues recently become known for the COX-2 inhibitors such as celecoxib, rofecoxib and valdecoxib which were removed from the world market for causing poor cardiovascular health, leading to heart attack and other problems. In light of these new developments, the reversible inhibition of platelet aggregation by the L-threonine ester of NSAIDs of the present invention offers better therapy for patients who suffer from the aforementioned maladres, e.g., rheumatoid and osetoarthritis.

Despite the very major contribution which NSAIDs have made, difficulties have been encountered in providing more effective and convenient means of administration galenic formulations, for example, oral dosage form, which are both convenient and for the patient as well as providing appropriate bioavailability and allowing dosaging at an appropriate and controlled dosage rate) as well as the reported occurrence of undesirable side reactions; in particular severe gastric and duodenal ulcers, mucosal erythema, and edema, erosions, perforations, blood in stool, and ulcerative colitis have are obvious serious impediments to their wider use or application. The dual injury theory involves NSAID-mediated direct damage, followed by a systemic effect in which prostaglandin synthesis is inhibited. Topical injury may also occur as a result of the biliary excretion of active hepatic metabolites and subsequent duodenogastric reflux. (Arthritis and Rheumatism 1995; 38(1):5-18) The effects are additive; either topical or systemic mechanisms alone are sufficient to produce gastro duodenal mucosal damage.

Moreover, the above mentioned NSAIDs, (without being bond to L-Threonine) are characteristically highly hydrophobic and readily precipitate in the presence of even very minor amounts of water, e.g., on contact with the body (e.g., stomach fluids). It is accordingly extremely difficult to provide e.g., oral formulations which are acceptable to the patient in terms of form and taste, which are stable on storage and which can be administered on a regular basis to provide suitable and controlling patient dosaging.

Proposed liquid formulations, e.g., for oral administration of NSAIDs, have heretofore been based primarily on the use of natural gums, like Xanthan, cellulose, citric acid, and lime flavor etc. See e.g., U.S. Pat. No. 5,780,046. Commercially available NSAIDs drink-solution employs incompatible orange color and berry flavor, citric acid, Xanthan Gum, polysorbate 80, pregelatinized starch, glycerin, sodium benzoate, and additional artificial colors and flavors. Use of the drink solution and similar composition as proposed in the art is however accompanied by a variety of difficulties.

Further, the palatability of the known oil based system has proved problematic. The taste of the known drink-solution is, in particular, unpleasant. Admixture with an appropriate flavored drink, for example, chocolate drink preparation, at high dilution immediately prior to ingestion has generally been practiced in order to make regular therapy at all acceptable. Adoption of oil based systems has also required the use of high ethanol concentrations which, in and of itself is inherently undesirable, in particular where administration to children is foreseen. In addition, evaporation of the ethanol, e.g., from capsules (adopted in large part, to meet problems of palatability, as discussed or other forms (e.g., when opened)) results in the development of a NSAID precipitate. Where such compositions are presented in, for example, soft gelatin encapsulated form, this necessitates packaging of the encapsulated product in an air-tight component, for example, an air-tight blister or aluminum-foil blister package. This in turn renders the product both bulky and more expensive to produce. The storage characteristics of the aforesaid formulations are, in addition, far from ideal.

Gastric irritability of the NSAIDs has been a topic of great concern to the practicing physicians and as well as patients. Acute uses of aspirin, fenoprofen, flurbiprofen, indomethacin, ketorolac, meclofenamate, mefanamic acid, and piroxicam produce serious GI side effects. Even Ibuprofen is shown to cause severe gastric lesions upon long term use. Gastrointestinal toxicity is the most frequently encountered side effect associated with NSAIDs and presents considerable concern. Approximately one half of all hospital admissions for a bleeding ulcer are attributed to the use of NSAIDs, aspirin, or the two taken in combination during the week prior to admission. (Faulkner G, Prichard P, Somerville K, et al. Aspirin and bleeding peptic ulcers in the elderly. Br Med J. 1988; 297:1311-4313). A survey of Tennessee Medicaid patients who were hospitalized with GI complications showed that patients who used NSAIDs had approximately a fourfold greater risk for developing GI hemorrhage or peptic ulcer disease than patients not taking NSAIDs. (Griffin M R, Piper J M, Daugherty J R, et al. Nonsteroidal anti-inflammatory drug use and increased risk for peptic ulcer disease in elderly persons. Ann Intern Med. 1991; 114:257-263). Serious GI events, according to the FDA, occur in as many as 2% to 4% of patients per year who are taking continuous NSAID therapy for rheumatoid arthritis. The relative risk of gastric ulcer (4.725), duodenal ulcer (1.1 to 1.6), bleeding (3.8), perforation, and death are all increased by NSAID use when such patients are compared to those who do not take these products. In 1989, patients with rheumatoid arthritis had approximately 20,000 hospitalizations per year with an estimated cost of $10,000 per stay. (Fries J F, Miller S R, Spitz P W, et al. Toward an epidemiology of gastropathy associated with nonsteroidal anti-inflammatory drug use. J. Gastroenterology. 1989; 96:647-655).

There is also a need for providing some of the NSAIDs in a water soluble form for injection. It is well known that high concentrations of alcohol and tromethamine used to form a salt in the current formulations of Ketorolac are toxic. At present there is no formulation that would allow the NSAIDs to be in aqueous solution at the concentrations needed due to poor water solubility of the drug.

Beyond all these very evident practical difficulties lies the occurrence of undesirable side effects already alluded to and observed, employing available oral dosage forms.

Several proposals to meet these various problems have been suggested in the art, including both solid and liquid oral dosage forms. An overriding difficulty which has, however, remained is the inherent insolubility of the NSAIDs in aqueous media, hence preventing the use of a dosage form which can contain NSAIDs in sufficiently high concentration to permit convenient use and yet meet the required criteria in terms of bioavailability, e.g. enabling effective resorption from the stomach or gut lumen and achievement of consistent and appropriately high blood/blood-serum levels.

The derivatives of the present invention with respect to NSAIDs overcome the problems described hereinabove. More specifically, an embodiment of the present invention is directed to a derivative of the present invention of a NSAID which significantly enhances its solubility in aqueous solutions, thereby avoiding the need to utilize a carrier, such as ethanol or castor oil when administered as a solution. Moreover, the derivatives of the present invention with respect to an NSAID do not exhibit the side effects of the prior art formulations. Further, these derivatives of the present invention are almost completely devoid of gastric irritability upon oral administration, thereby enhancing significantly the therapeutic index of the derivatives tested and their efficacy.

Accordingly, in one aspect, the present invention is directed to a derivative of the present invention of NSAIDs, i.e., a L-Threonine covalently bounded to the NSAID.

The preferred derivatives of the NSAIDs have the formula

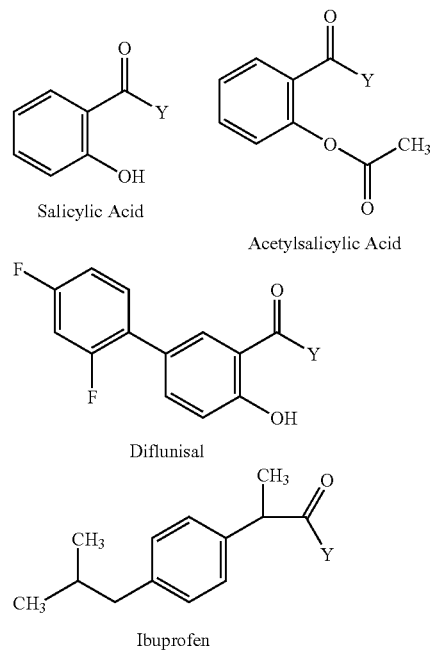

-continued

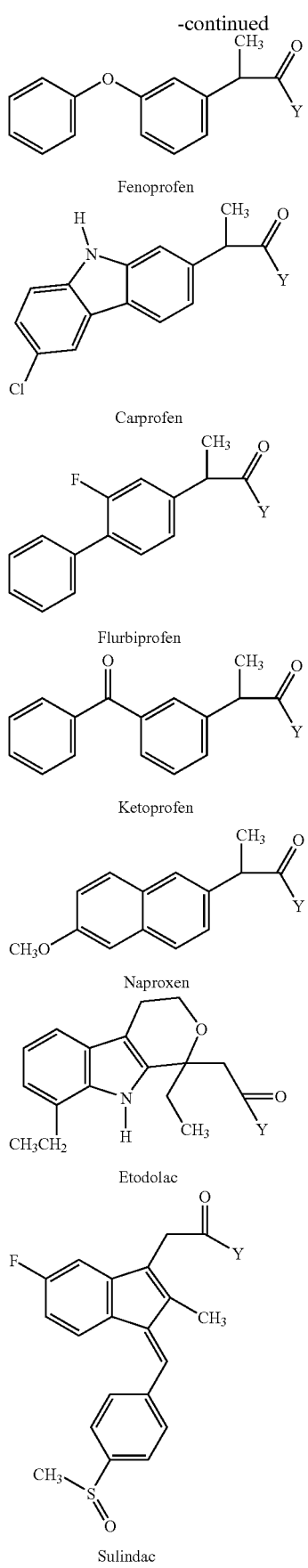

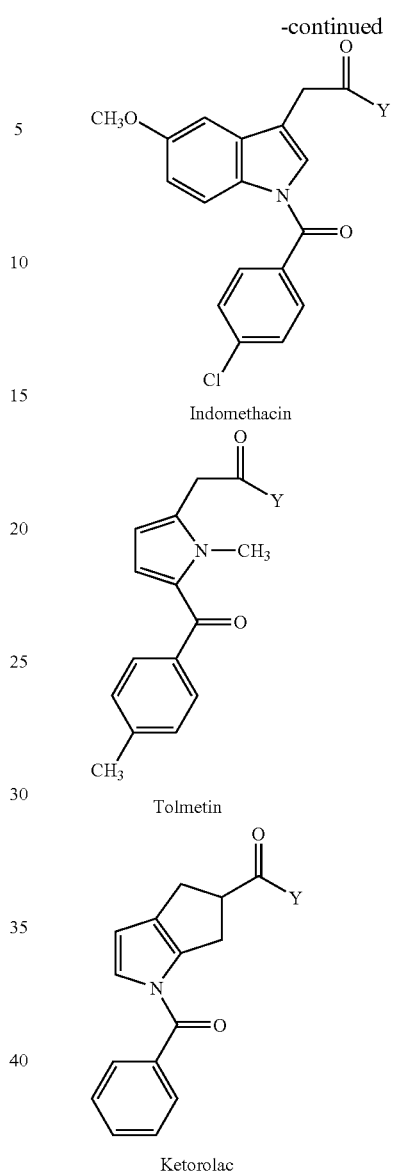

or pharmaceutically acceptable salts thereof; wherein Y is either

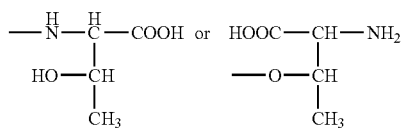

in which either an amine group or the hydroxyl group of Threonine is reacted with the carboxylic acid group of the NSAIDs.

PCT application WO 2000/23419 of which Tom Jarvinen is an inventor, describes amino acid esters of NSAIDs, wherein the NSAIDs are attached covalently to amino acids via spacer groups, according to the formula:

R—COO—$R_1$—O—$R_2$ where $R_1$ as defined therein is the spacer group, which may be a saturated, unsaturated, straight chain, branched, or cyclic alkylene or alkylidene group of 1-8 carbon atoms, which can be optionally substituted with 1-3 groups selected from halogen, hydroxyl, thiol, amino, mono- or dialkylamino, acylamino, carboxyl, alkylcarboxyl, acyl, aryl, aroyl, aralkyl, cyano, nitrol, alkoxy, alkenyloxy, alkylcarbonyloxy and arylcarbonyloxy derivatives, and $R_2$ as defined therein is an aminoacyl residue of a synthetic or natural amino acid of the formula

—C(=O)—$R_3$—$NH_2$ and the preferred amino acids are naturally occurring ones such as lysine, proline, glycine and the like.

According to Jarvinen, these amino acid linked NSAIDs are suitable for transdermal application only, and he gives examples of such derivatives made with Naproxen.

There are several problems with these derivatives. For example, it is not evident if these derivatives can be administered via oral route. Upon administration of any of these derivatives by any route, the body fluids will cause hydrolysis of the double esters leading to the formation of the NSAIDs, amino acid and finally the spacer group which will be a diol. All such diols produced in the body are highly toxic and hence the usefulness of this approach is limited.

However the present invention is directed towards L-Threonine esters of NSAIDs, where the amino acids are attached to the NSAIDs directly via ester bond, thus avoiding toxicity of any spacer groups.

Contrary to the approach of Jarvinen and others, the current invention only releases the NSAIDs or the NSAID linked amino acid and once broken down in the body, it releases, the amino acid, threonine, which is not toxic. Hence the derivatives of the present invention are far superior to their unesterified counterparts (i.e, intact NSAIDs) in terms of toxicity, efficacy and therapeutic index.

The present invention is also directed to a pharmaceutical composition comprising a therapeutically effective amount of the various derivatives of the present invention of NSAIDs above and a pharmaceutical carrier therefor.

In another embodiment, the present invention is directed to a method of treating a patient in need of NSAID therapy, which method comprises administering to said patient an effective amount of the derivative of the present invention of NSAIDs.

In a further embodiment, the present invention is directed to a method of enhancing the solubility of NSAID in an aqueous solution comprising reacting the carboxyl functionality of each of the NSAIDs with L-Threonine and isolating the products thereof.

In a still further embodiment, the present invention is directed to a method of substantially and in a therapeutically efficacious manner, reducing or eliminating the gastric mucosal damage of NSAIDs when administered to a patient which comprises reacting the carboxyl functionality of each of the NSAID molecule with either amine or hydroxyl function of L-Threonines to form either an amide or ester covalent bond respectively and isolating the product thereof and administering said product to the patient.

A. Synthesis of Ibuprofen L-Threonine Derivatives

Overview:

The procedure for the synthesis of L-Threonine esters of Ibuprofen is outlined in Synthetic Sequence section. The complete procedure and analytical data is given in the Experimental Section. Again, these synthetic schemes are exemplary. In general, (±)-Ibuprofen (4-10 g, in batches) was coupled with the N-benzyloxy/benzyl ester protected L-Threonines (1 equivalent) with 1-(3-dimethylaminopropyl)-3-ethylcarbodiimide, hydrochloride (EDC, 1 equivalent) in the presence of a catalytic amount of 4-(N,N-dimethyamino)-pyridine (DMAP). Once the reactions were complete, any excess EDC was removed by extraction with water, DMAP was removed by extraction with dilute acid, and Ibuprofen was removed by extraction with sodium bicarbonate. After drying over sodium sulfate, filtration, and concentration the crude protected L-Threonine esters of (±)-Ibuprofen were either used directly or purified by flash chromatography on silica gel to generate the protected esters in good yield (85-95%). The column chromatography was generally not necessary if a slight excess of Ibuprofen and coupling agent were used, and a thorough extraction procedure was conducted. The protecting groups were removed by hydrogenation (25-35 psi $H_2$) in the presence of 10% palladium on carbon and hydrochloric acid. Yields for the deprotection step ranged from 70-90%. The Threonine derivative was isolated as a solid.

After filtration and drying the hydrochloride salts of the serine and threonine esters of (±)-Ibuprofen were purified by crystallization. The hydrochloride salt of the L-hydroxyproline-Ibuprofen ester was a gel that would not solidify/crystallize. In this case the hydrogenation was repeated without the use of acid and the neutral compound was purified.

Because the Ibuprofen started as a mixture of enantiomers, the final products were delivered as a mixture of diastereomers. In the case of the threonine ester of Ibuprofen, washing with water, acetone or acetonitrile could readily separate the final diastereomeric salts. The insoluble isomer (SPI0016A) was determined to be the active isomer by comparison with an authentic standard prepared from S-(+)-Ibuprofen. This synthesis repeated substituting L-serine and L-hydroxy-proline for L-Threonine. The serine and hydroxyproline esters of (±)-Ibuprofen could not be readily separated in this fashion.

Synthetic Sequence:

1. SPI0015

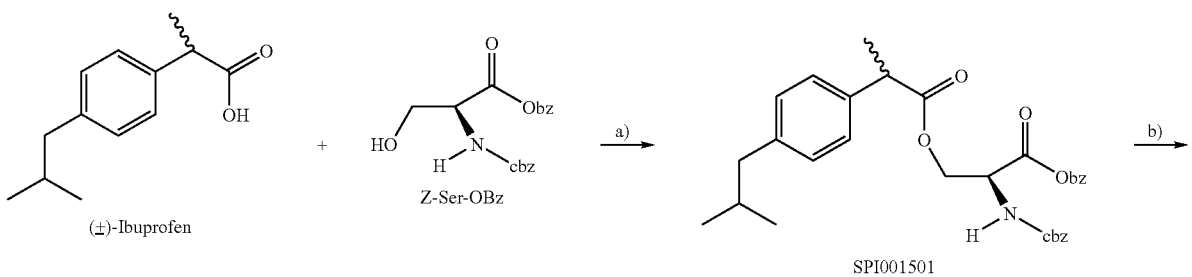

SPI001501

-continued
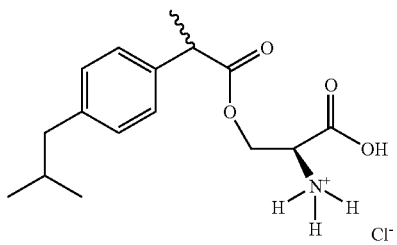
1. SPI0016A and SPI0016B
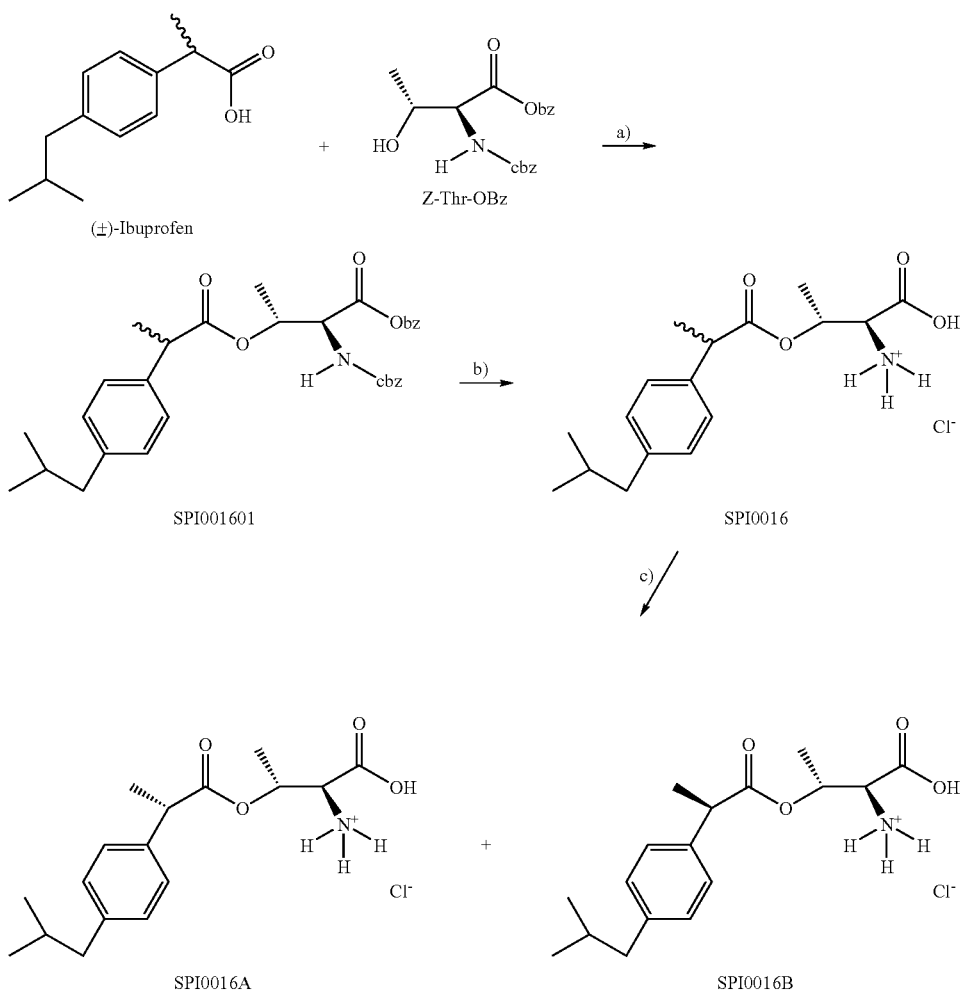
3. SPI0017
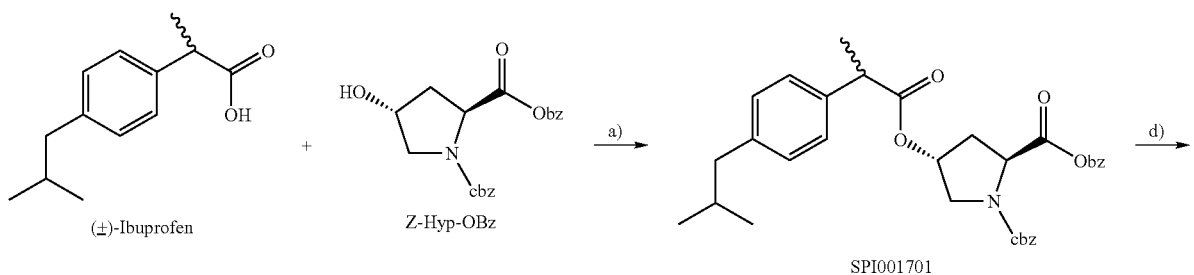

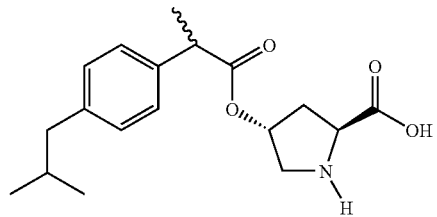

SPI0017

Synthesis of the L-serine, L-Threonine, and L-hydroxyproline esters of (±)-Ibuprofen: a) EDC, DMAP, CH$_2$Cl$_2$; b) HCl, 10% Pd/C, EtOH c) acetone, d) 10% Pd/C, EtOH.

Experimental Section:

The synthesis of SPI0015, SPI0016 and SPI0017 were conducted in two or three batches. Reagents mentioned in the experimental section were purchased at the highest obtainable purity from Sigma-Aldrich, Acros, or Bachem, except for solvents, which were purchased from either Fisher Scientific or Mallinkrodt.

1) Preparation of (±)-Ibuprofen-L-Serine Ester, Hydrochloride (SPI0015).

(±)-Ibuprofen (5.04 g, 24.4 mmole), N-carbobenzyloxy-L-serine benzyl ester (8.11 g, 24.6 mmole), 1-(3-dimethylaminopropyl)-3-ethylcarbodiimide, hydrochloride (EDC, 4.87 g, 25.4 mmole), and 4-(N,N-dimethylamino)-pyridine (DMAP, 0.40 g, 3.27 mmole) were dissolved in dichloromethane (150 mL) at room temperature, under an argon atmosphere. After stirring for 22 hours under an argon atmosphere at room temperature, water (100 mL) was added and the layers were separated. The dichloromethane layer was washed again with water (100 mL) and dried for 1 hour over sodium sulfate (5 g). After filtration and concentration under reduced pressure, the remaining oil was purified by flash chromatography on silica gel (250 g), eluting with hexanes/ethyl acetate (3:1). The procedure generated the protected L-serine-(±)-Ibuprofen ester (SPI001501) as a colorless solid (11.4 g, 90% yield).

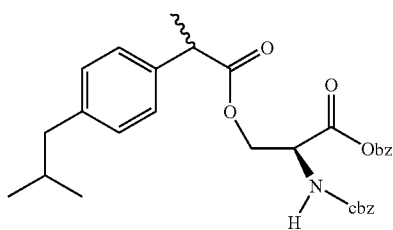

SPI001501

2(S)-Benzyloxycarbonylamino-3-[2(R,S)-(4-isobutyl-phenyl)-propionyloxy]-propionic acid benzyl ester:

$^1$H NMR (300 MHz, CDCl$_3$): δ=7.40-7.20 (m, 10H), 7.14-7.01 (m, 4H), 5.50 (d, ½H, J=8.4 Hz), 5.29 (d, ½H, J=8.4 Hz), 5.11-5.02 (m, 2.5H), 4.90 (d, ½H, J=12 Hz), 4.62 (m, 1H), 4.49-4.43 (m, 1H), 4.36-4.32 (m, 1H), 3.59 (m, 1H), 2.39-2.35 (m, 2H), 1.78 (m, 1H), 1.42-1.39 (m, 3H), 0.85 (d, 6H, J=6.6 Hz).

$^{13}$C NMR (75 MHz, CDCl$_3$): δ=174.05, 169.19, 169.07, 155.68, 140.73, 137.20, 136.12, 135.05, 134.91, 129.44, 128.67, 128.65, 128.60, 128.41, 128.33, 128.30, 128.19, 127.19, 127.16, 67.75, 67.32, 64.51, 64.32, 53.71, 45.16, 45.02, 30.35, 22.60, 18.27.

The protected Ibuprofen-L-serine ester (22.50 g, 43.4 mmole) was dissolved in ethanol (200 mL) at room temperature and added to a Parr bottle that contained 10% palladium on carbon (3.86 g, 50% wet) under a nitrogen atmosphere. Hydrochloric acid (10 mL 37% HCl in 30 mL water) was added and the nitrogen atmosphere was replaced with hydrogen gas (25 psi). After 4 hours of shaking, the palladium catalyst was removed by filtration through celite. The ethanol/water was removed under reduced pressure. The remaining white solids were washed with water (25 mL), acetone (20 mL) and dried under high vacuum (4 hours at 88° C.). The experiment produced (±)-Ibuprofen-L-serine ester, hydrochloride SPI0015 (11.3 g, 80% yield) as a colorless solid.

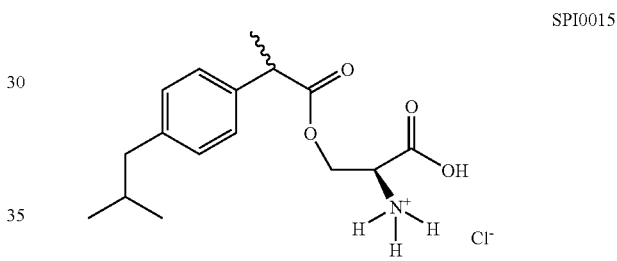

SPI0015

2(S)-Amino-3-[2(R,S)-(4-isobutylphenyl)-propionyloxy]-propionic acid, hydrochloride; ((R,S)-Ibuprofen-L-Serine ester, hydrochloride):

$^1$H NMR (300 MHz, DMSO): δ=8.92 (br s, 3H), 7.22 (t, 2H, J=7.5 Hz), 7.10 (d, 2H, J=7.5 Hz), 4.56 (m, 1H), 4.37-4.20 (m, 2H), 3.83 (q, 1H, J=6.9 Hz), 2.41 (d, 2H, J=6.9 Hz), 1.80 (m, 1H), 1.41 (d, 3H, J=6.9 Hz), 0.85 (d, 6H, J=6.9 Hz).

$^{13}$C NMR (75 MHz, DMSO): δ=173.36, 173.32, 168.08, 168.04, 139.70, 128.96, 129.92, 127.20, 127.05, 62.47, 51.59, 51.49, 44.28, 44.00, 43.90, 29.68, 22.28, 18.70, 18.42.

HPLC analysis:

99.13% purity; rt=3.133 min; Luna C18 5u column (sn 167917-13); 4.6×250 mm; 254 nm; 50% ACN/50% TFA buffer (0.1%); 35 C; 20 ul inj.; 1 ml/min; 1 mg/mL sample size; sample dissolved in mobile phase.

CHN analysis:

calc.: C, 58.27; H, 7.33; N, 4.25. found: C, 58.44; H, 7.46; N, 4.25.

Melting point: 169.5-170.5° C.

2a) Preparation and Separation of (±)-Ibuprofen-L-Threonine Ester, Hydrochloride (SPI0016A and SPI0016B).

(±)-Ibuprofen (4.15 g, 20.11 mmole), N-carbobenzyloxy-L-Threonine benzyl ester (6.90 g, 20.11 mmole), 1-(3-dimethylaminopropyl)-3-ethylcarbodiimide, hydrochloride (EDC, 3.95 g, 20.6 mmole), and 4-(N,N-dimethylamino)-pyridine (DMAP, 0.25 g, 2.0 mmole) were dissolved in dichloromethane (50 mL) at room temperature, under an argon atmosphere. After stirring for 19 hours, the dichloromethane layer was washed with water (50 mL), 5% hydrochloric acid (2×25 mL), water (25 mL), saturated sodium bicarbonate (2×25 mL), and water (50 mL). After drying for one hour over sodium sulfate (5 g), filtration, and concentration under reduced pressure, the remaining oil was used without further purification. The procedure generated the protected L-Threonine-(±)-Ibuprofen ester (SPI001601) as a light yellow oil (10.2 g, 95.3% yield), which solidified on standing.

SPI001601

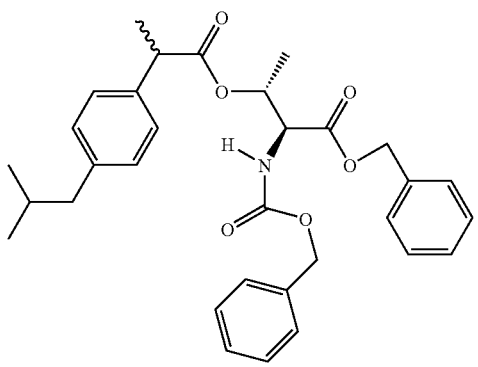

2(S)-Benzyloxycarbonylamino-3-[2(R,S)-(4-isobutyl-phenyl)-propionyloxy]-butyric acid benzyl ester:

$^1$H NMR (300 MHz, CDCl$_3$): δ=7.40-7.15 (m, 10H), 7.14-7.01 (m, 4H), 5.48-5.25 (m, 2H), 5.11-5.01 (m, 3H), 4.90 (d, ½H, J=12 Hz), 4.68 (d, ½H, J=12 Hz), 4.48 (m, 1H), 3.60-3.48 (m, 1H), 2.39 (m, 2H), 1.79 (m, 1H), 1.42-1.35 (m, 3H), 1.27 (d, 1.5H, J=6.6 Hz), 1.17 (d, 1.5H, J=6.6 Hz), 0.85 (m, 6H).

$^{13}$C NMR (75 MHz, CDCl$_3$): δ=173.32, 169.70, 169.30, 156.55, 140.75, 137.38, 137.22, 136.14, 135.07, 134.99, 129.45, 129.41, 128.65, 128.39, 128.22, 127.21, 127.14, 70.97, 70.70, 67.81, 67.66, 67.53, 57.83, 45.19, 30.39, 22.61, 18.57, 18.30, 17.18, 16.87.

The protected Ibuprofen-L-Threonine ester (10.15 g, 19.0 mmole) was dissolved in warm ethanol (150 mL) and added to a Parr bottle that contained 10% palladium on carbon (3.4 g, 50% wet) under a nitrogen atmosphere. Hydrochloric acid (6 mL 37% HCl in 20 mL water) was added and the nitrogen atmosphere was replaced with hydrogen gas (30 psi). After 3 hours of shaking, the palladium catalyst was removed by filtration through celite (30 g). The ethanol/water was removed under reduced pressure. The experiment produced (±)-Ibuprofen-L-Threonine ester, hydrochloride (SPI0016A and SPI0016B, 6.4 g, 97% crude yield) as a colorless solid. The crude mixture of diastereomers was stirred in acetone (200 mL) for 2 hours at room temperature under an argon atmosphere. After 2 hours the solids (2.84 g, SPI0016A) were filtered. The filtrate (SPI0016B, 3.0 g) was concentrated under reduced pressure.

Purification of SPI0016A (Active Isomer):

After 3 batches of the S-Ibuprofen-L-Threonine ester (SPI0016A) had been completed, the batches were combined (8.78 g total) and crystallized three times from deionited ultra filtered water ("DIUF") (100 mL). Each time a small amount of zwitterion was generated. In order to regenerate the salt, the solid generated (from each crystallization) was dissolved in 1% hydrochloric acid in ethanol (3 mL 37% hydrochloric acid in 100 mL ethanol). The ethanol solution was then concentrated under reduced pressure at room temperature. After the third crystallization and regeneration procedure, the salt (5.6 g) was stirred in acetonitrile (100 mL) for 44 hours at room temperature, under an argon atmosphere. The salt was then filtered and dried under high vacuum at 50-55° until the weight was constant (5.5 g).

SPI0016A

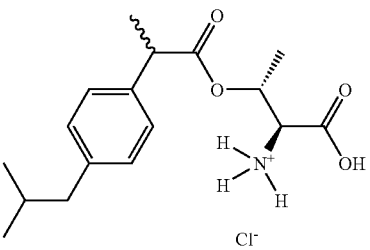

2(S)-Amino-3(R)-[2(S)-(4-isobutyl-phenyl)-propionyloxy]-butyric acid; (S-Ibuprofen-L-Threonine ester, hydrochloride, active isomer):

$^1$H NMR (300 MHz, DMSO): δ=8.76 (br s, 3H), 7.19 (d, 2H, J=8.1 Hz), 7.11 (d, 2H, J=8.1 Hz), 5.28 (dq, 1H, J=6.3, 3.6 Hz), 4.14 (q, 1H, J=3.6 Hz), 3.80 (q, 1H, J=7.2 Hz), 2.41 (d, 2H, J=7.2 Hz), 1.80 (m, 1H), 1.37 (d, 3H, J=7.2 Hz), 1.21 (d, 3H, J=6.3 Hz), 0.85 (d, 6H, J=6.6 Hz).

$^{13}$C NMR (75 MHz, DMSO): δ=172.66, 168.24, 139.68, 137.24, 128.95, 126.97, 67.98, 55.35, 44.23, 43.83, 29.66, 22.24, 18.52, 16.47.

CHN analysis:

calc.: C, 59.38; H, 7.62; N, 4.07. found: C, 59.17; H, 7.63; N, 4.04.

HPLC analysis:

98.28% purity; r.t.=6.951 min.; 60% TFA (0.1%)/40% acetonitrile; 1 mL/min; 37.5 C; Luna C18, 3u column (SN 167917-13), 4.6×250 mm; 22 ul injection.

Optical rotation: +24.5°

Melting Point: 189-190° C.

2) Purification of SPI0016B (Inactive Isomer):

After 3 batches of the R-Ibuprofen-L-Threonine ester (SPI0016B) had been completed, the batches were combined (9.02 g total) and crystallized from DIUF water (50 mL). A small amount of zwitterion was generated during the crystallization. In order to regenerate the salt, the solid generated was dissolved in 1% hydrochloric acid in ethanol (3 mL 37% hydrochloric acid in 100 mL ethanol). The ethanol solution was then concentrated under reduced pressure at room temperature. The remaining salt (5.93 g) was crystallized three times from hot toluene (100 mL) with the addition of a small amount on acetone (1 mL). The salt was then filtered and dried under high vacuum at room temperature until the weight was constant (5.1 g).

SPI0016B

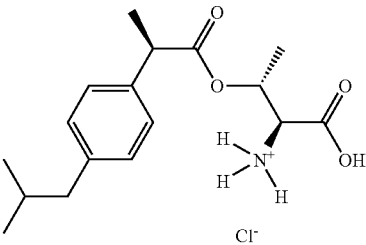

2(S)-Amino-3(R)-[2(R)-(4-isobutyl-phenyl)-propionyloxy]-butyric acid; (R-Ibuprofen-L-Threonine ester, hydrochloride, inactive isomer):

¹H NMR (300 MHz, DMSO): δ=8.82 (br s, 3H), 7.23 (d, 2H, J=7.8 Hz), 7.10 (d, 2H, J=7.8 Hz), 5.27 (m, 1H), 4.18 (m, 1H), 3.80 (q, 1H, 7.2 Hz), 2.41 (d, 2H, J=7.2 Hz), 1.81 (m, 1H), 1.41 (d, 3H, J=6.9 Hz), 1.34 (d, 3H, J=6.3 Hz), 0.85 (d, 6H, J=6.3 Hz).

¹³C NMR (75 MHz, DMSO): δ=72.56, 168.08, 139.64, 136.98, 128.84, 127.14, 68.8, 55.29, 44.28, 29.69, 22.28, 18.24, 16.41.

CHN analysis:

calc.: C, 59.38; H, 7.62; N, 4.07. found: C, 59.30; H, 7.60; N, 4.05.

HPLC analysis:

98.43% purity; r.t.=6.19 min.; 60% TFA (0.1%)/40% acetonitrile; 1 mL/min; 37.5 C; Luna C18, 3u column (SN 167917-13), 4.6×250 mm; 22 ul injection.

Optical Rotation: +10.4°

Melting Point: 176-177° C.

2b) Preparation of the S-(+)-Ibuprofen-L-Threonine Ester, Hydrochloride Standard (SPI0016S).

S-(+)-Ibuprofen (2.0 g, 9.69 mmole), N-carbobenzyloxy-L-Threonine benzyl ester (3.25 g, 9.91 mmole), 1-(3-dimethylaminopropyl)-3-ethylcarbodiimide, hydrochloride (EDC, 1.90 g, 9.91 mmole), and 4-(N,N-dimethylamino)-pyridine (DMAP, 0.12 g, 1.0 mmole) were dissolved in dichloromethane (25 mL) at room temperature, under an argon atmosphere. After stirring for 4 hours, the dichloromethane layer was washed with water (25 mL), 5% hydrochloric acid (25 mL), saturated sodium bicarbonate (2×25 mL), and water (25 mL). After drying for one hour over sodium sulfate (5 g), filtration, and concentration under reduced pressure, the remaining oil was used without further purification. The procedure generated the protected S-(+)-Ibuprofen-L-Threonine ester (SPI001601S) as a light yellow oil (5.01 g, 98% yield), which solidified on standing.

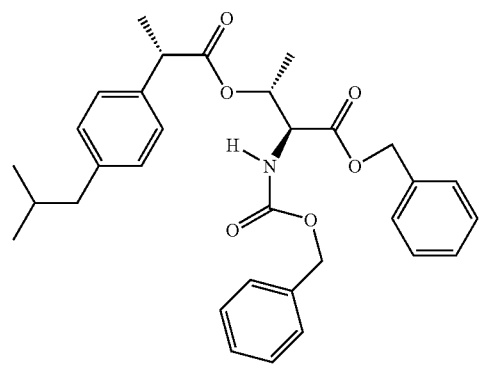

SPI001601S

2(S)-Benzyloxycarbonylamino-3-[2(R,S)-(4-isobutyl-phenyl)-propionyloxy]-butyric acid benzyl ester:

¹H NMR (300 MHz, CDCl₃): δ=7.35-7.23 (m, 10H), 7.10 (d, 2H, J=7.8 Hz), 7.05 (d, 2H, J=7.8 Hz), 5.48-5.25 (m, 2H), 5.17-5.01 (m, 4H), 4.50 (dd, 1H, J=9.6, 1.8 Hz), 3.50 (q, 1H, J=7.2 Hz), 2.40 (d, 2H, J=7.2 Hz), 1.80 (m, 1H), 1.37 (d, 3H, J=7.2 Hz), 1.17 (d, 3H, J=6.3 Hz), 0.86 (d, 6H, J=6.6 Hz).

¹³C NMR (75 MHz, CDCl₃): δ=173.29, 169.69, 156.51, 140.68, 137.21, 136.08, 135.06, 129.40, 128.70, 128.66, 128.57, 128.38, 128.24, 127.14, 70.70, 67.80, 67.53, 57.87, 45.19, 45.11, 30.39, 22.61, 18.57, 16.87.

The protected S-(+)-Ibuprofen-L-Threonine ester (5.0 g, 9.40 mmole) was dissolved in warm ethanol (100 mL) and added to a Parr bottle that contained 10% palladium on carbon (1.0 g, 50% wet) under a nitrogen atmosphere. Hydrochloric acid (1 mL 37% HCl in 10 mL water) was added and the nitrogen atmosphere was replaced with hydrogen gas (32 psi). After 2 hours of shaking, the palladium catalyst was removed by filtration through celite (30 g). The ethanol/water was removed under reduced pressure. The experiment produced S-(+)-Ibuprofen-L-Threonine ester, hydrochloride (SPI0016S, 2.8 g, 85% crude yield) as a colorless solid. The salt was stirred in acetone (50 mL) for 3 hours at room temperature under an argon atmosphere. After 3 hours the solids (2.24 g, 69% yield) were filtered and dried under high vacuum at room temperature, until the weight was constant.

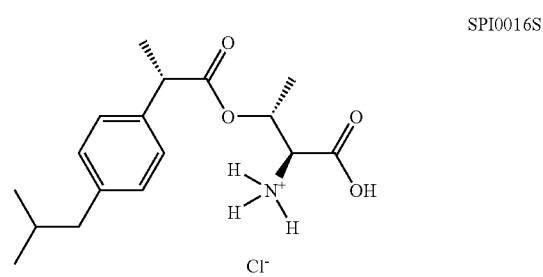

SPI0016S

2(S)-Amino-3(R)-[2(S)-(4-isobutyl-phenyl)-propionyloxy]-butyric acid; (S-Ibuprofen-L-Threonine ester, hydrochloride, active isomer):

¹H NMR (300 MHz, DMSO): δ=8.76 (br s, 3H), 7.19 (d, 2H, J=8.1 Hz), 7.11 (d, 2H, J=8.1 Hz), 5.28 (dq, 1H, J=6.3, 3.6 Hz), 4.14 (q, 1H, J=3.6 Hz), 3.80 (q, 1H, J=7.2 Hz), 2.41 (d, 2H, J=7.2 Hz), 1.80 (m, 1H), 1.37 (d, 3H, J=7.2 Hz), 1.21 (d, 3H, J=6.3 Hz), 0.85 (d, 6H, J=6.6 Hz).

¹³C NMR (75 MHz, DMSO): δ=172.66, 168.24, 139.68, 137.24, 128.95, 126.97, 67.98, 55.35, 44.23, 43.83, 29.66, 22.24, 18.52, 16.47.

HPLC analysis:

98.28% purity; r.t.=6.951 min.; 60% TFA (0.1%)/40% acetonitrile; 1 mL/min; 37.5 C; Luna C18, 3u column (SN 167917-13), 4.6×250 mm; 22 ul injection.

Optical rotation: +26.5

Melting Point: 189-190° C.

3) Preparation of the (±)-Ibuprofen-L-Hydroxyproline Ester (SPI0017).

(±)-Ibuprofen (5.10 g, 24.7 mmole), N-carbobenzyloxy-L-hydroxyproline benzyl ester (8.80 g, 24.7 mmole), 1-(3-dimethylaminopropyl)-3-ethylcarbodiimide, hydrochloride (EDC, 5.10 g, 26.0 mmole), and 4-(N,N-dimethylamino)-pyridine (DMAP, 0.30 g, 2.40 mmole) were dissolved in dichloromethane (100 mL) at room temperature, under an argon atmosphere. After stirring for 24 hours under an argon atmosphere at room temperature, water (100 mL) was added and the layers were separated. The dichloromethane layer was washed again with water (100 mL), 5% sodium bicarbonate (2×50 mL) and dried for 1 hour over sodium sulfate (5 g). After filtration and concentration under reduced pressure, the remaining oil was used without further purification. The procedure generated the protected (±)-Ibuprofen-L-hydroxyproline ester (SPI001701) as a light yellow oil (11.5 g, 85% yield).

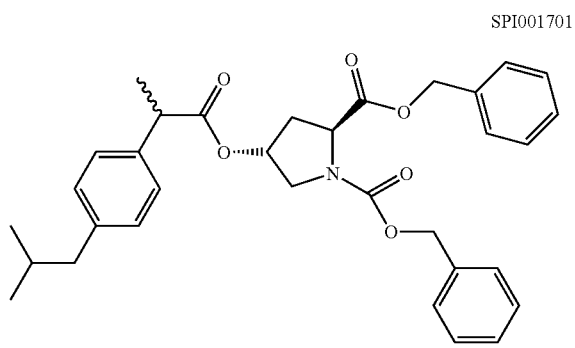

4(R)-[2-(4-Isobutyl-phenyl)-propionyloxy]-pyrrolidine-2(S)-carboxylic acid; ((R,S)-Ibuprofen-L-hydroxyproline ester):

$^1$H NMR (300 MHz, CDCl$_3$): δ=7.33-7.02 (m, 14H), 5.25-4.95 (m, 5H), 4.51-4.19 (m, 1H), 3.75-3.50 (m, 3H), 2.40 (d, 2H, J=6.9 Hz), 2.15 (m, 1H), 1.81 (m, 1H), 1.44 (d, 3H, J=7.0 Hz), 0.87 (d, 6H, J=6.6 Hz).

$^{13}$C NMR (75 MHz, CDCl$_3$): δ=173.99, 171.93, 171.72, 154.68, 154.15, 140.70, 137.33, 137.04, 136.23, 135.44, 135.23, 129.41, 128.59, 128.47, 128.35, 128.19, 128.08, 127.89, 127.02, 72.86, 72.16, 67.40, 67.18, 67.09, 58.12, 57.83, 52.66, 52.49, 52.13, 45.15, 36.63, 35.67, 32.07, 30.33, 29.23, 22.90, 22.58, 18.36.

The protected Ibuprofen-L-hydroxyproline ester (11.40 g, 43.4 mmole) was dissolved in ethanol (150 mL) at room temperature and added to a Parr bottle that contained 10% palladium on carbon (2.73 g, 50% wet) under a nitrogen atmosphere. The nitrogen atmosphere was replaced with hydrogen gas (34 psi). After 5 hours of shaking, the palladium catalyst was removed by filtration through celite. The ethanol was removed under reduced pressure. The remaining white solids (6.60 g) were washed with DIUF water (50 mL), diethyl ether (50 mL) and dried under high vacuum until the weight was constant. The experiment produced (±)-Ibuprofen-L-hydroxyproline ester SPI0017 (5.64 g, 84% yield) as a colorless solid.

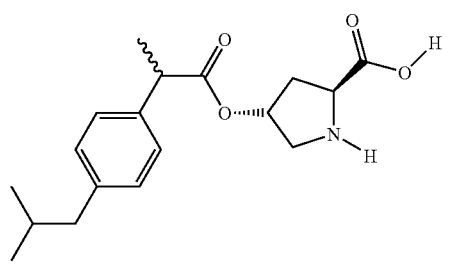

4(R)-[2-(4-Isobutyl-phenyl)-propionyloxy]-pyrrolidine-2(S)-carboxylic acid; ((R,S)-Ibuprofen-L-hydroxyproline ester):

$^1$H NMR (300 MHz, CDCl$_3$): δ=7.22 (d, 2H, J=7.2 Hz), 7.09 (d, 2H, J=7.2 Hz), 5.27 (m, 1H), 4.40 (t, 0.5H, J=7 Hz), 4.24 (t, 0.5H, J=9 Hz), 3.75 (m, 1H), 3.61 (m, 1H), 3.28 (d, 0.5H, J=13 Hz), 3.15 (d, 0.5H, J=13 Hz), 2.42-2.10 (m, 4H), 1.78 (m, 1H), 1.40 (br t, 3H, J=6 Hz), 0.82 (d, 6H, J=6 Hz). (mixture of diastereomers)

$^{13}$C NMR (75 MHz, CDCl$_3$): δ=173.28, 173.23, 168.98, 139.88, 137.33, 137.23, 129.12, 127.26, 127.17, 72.58, 57.60, 57.50, 50.24, 50.12, 44.34, 44.15, 34.31, 34.16, 29.77, 22.34, 18.43, 18.23. (mixture of diastereomers)

HPLC analysis:

100% purity; r.t.=5.35, 5.22 min.; 55% TFA (0.1%), 45% ACN; 1 mL/min; 32.3 C, Luna C18, serial #188255-37; 20 ul inj.

CHN analysis:

calc.: C, 67.69; H, 7.89; N, 4.39. found: C, 67.47; H, 7.87; N, 4.30.

Melting Point: 198-199° C.

Overview Ketoprofen S(+) Threonine Ester Synthesis:

The procedure for the synthesis of the L-Threonine esters of Ketoprofen is outlined in the Synthetic Sequence section. The complete procedure and analytical data is given in the Experimental Section. In general, (±)-Ketoprofen (5 g) was coupled with N-boc-L-Threonine t-butyl ester (1 equivalent) with 1-(3-dimethylaminopropyl)-3-ethylcarbodiimide, hydrochloride (EDC, 1 equivalent) in the presence of a catalytic amount of 4-(N,N-dimethyamino)-pyridine (DMAP). Once the reaction was complete, any excess EDC was removed by extraction with water, DMAP was removed by extraction with dilute acid, and Ketoprofen was removed by extraction with sodium bicarbonate. After drying over sodium sulfate, filtration, and concentration the crude protected L-Threonine-(±)-Ketoprofen was purified by flash chromatography on silica gel to generate the protected L-Threonine ester in good yield (98%). The protecting groups were removed by treatment with 2M hydrochloric acid in diethyl ether to cleave the boc group, followed by treatment with trifluoroacetic acid to remove the t-butyl ester. After drying, the mixture of L-Threonine-R,S(±)-Ketoprofen esters was separated by crystallization from acetonitrile. The hydrochloride salt of the L-Threonine-S(+)-Ketoprofen ester preferentially precipitated from acetonitrile. A sample of an optically pure standard was prepared starting with S(+)-ketoprofen for comparison. After drying and analysis, a sample of L-Threonine-S(+)-Ketoprofen ester, hydrochloride (1.75 g) was separated from the mixture.

Synthetic Sequence:

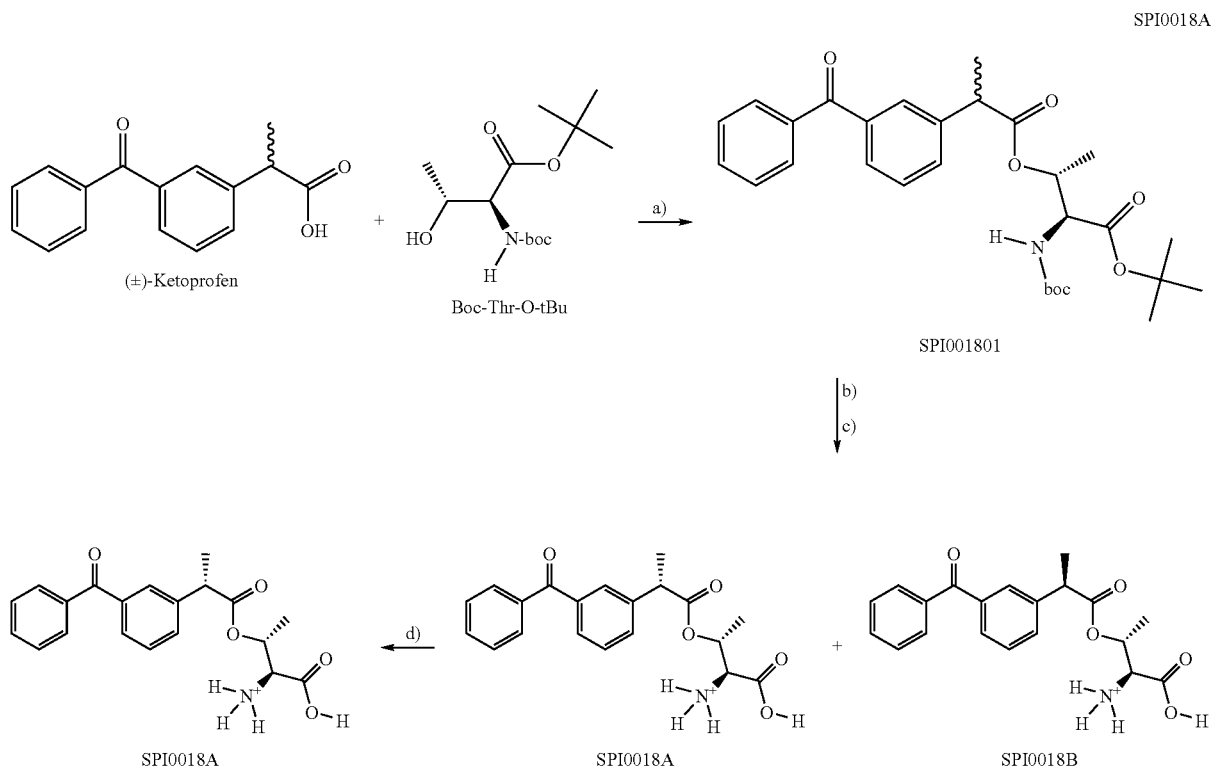

Synthesis of the L-Threonine esters of (±)-Ketoprofen: a) EDC, DMAP, CH₂Cl₂; b) HCl (2M); c) TFA; d) ACN (crystallization).

Experimental Section:

The synthesis of SPI0018A was conducted in a single batch. Reagents mentioned in the experimental section were purchased at the highest obtainable purity from Sigma-Aldrich, Acros, or Bachem, except for solvents, which were purchased from either Fisher Scientific or Mallinkrodt.

Preparation and Separation of S(+)-Ketoprofen-L-Threonine Ester, Hydrochloride (SPI0018A).

(±)-Ketoprofen (5.32 g, 20.92 mmol), N-t-butylcarbonyl-L-Threonine t-butyl ester (Boc-Thr-OtBu (5.17 g, 18.72 mmol), 1-(3-dimethylaminopropyl)-3-ethylcarbodiimide, hydrochloride (EDC, 4.0 g, 20.9 mmol), and 4-(N,N-dimethylamino)-pyridine (DMAP, 0.22 g) were dissolved in dichloromethane (50 mL) at room temperature, under an argon atmosphere. After stirring for 5 hours, the dichloromethane layer was washed with water (50 mL), 5% hydrochloric acid (2×25 mL), water (25 mL), saturated sodium bicarbonate (2×25 mL), and water (50 mL). After drying for one hour over sodium sulfate (5 g), filtration, and concentration under reduced pressure, the remaining oil (10.3 g) was purified by column chromatography on silica gel (150 g), eluting with hexanes/ethyl acetate (2:1). After combining the product containing fractions, concentration and drying under high vacuum, the procedure generated the protected L-Threonine-(±)-Ketoprofen ester (SPI001801) as a clear oil (9.42 g, 98% yield).

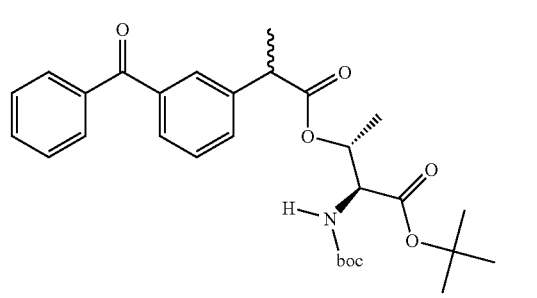

3-[2(R,S)-(3-Benzoyl-phenyl)-propionyloxy]-2(S)-tert-butoxycarbonylamino-butyric acid tert-butyl ester: (mix of diastereomers)

¹H NMR (300 MHz, CDCl₃): δ=7.83-7.42 (m, 9H), 5.43 (dd, 1H, J=13.2, 6.9 Hz), 5.10 (dd, 1H, J=20.7, 9.3), 4.29 (t, 1H, J=11.7 Hz), 3.75 (q, 1H, J=7.2 Hz), 1.50-1.42 (m, 19.5H), 1.30-1.18 (m, 4.5H).

¹³C NMR (75 MHz, CDCl₃): δ=196.18, 172.62, 172.55, 168.85, 168.58, 155.81, 140.33, 140.23, 137.86, 137.39, 132.46, 132.42, 131.54, 131.38, 130.00, 129.31, 129.13, 129.02, 128.54, 128.27, 82.50, 82.37, 80.05, 71.38, 71.22, 57.59, 57.52, 45.46, 45.31, 28.40, 27.98, 27.84, 18.54, 18.48, 17.19, 16.84.

The protected (R,S)-Ketoprofen-L-Threonine ester (9.42 g, 18.41 mmol) was dissolved in dichloromethane (25 mL) under an argon atmosphere, at room temperature. Anhydrous hydrochloric acid in diethyl ether (2M, 25 mL) was added to the solution and the mixture was allowed to stir for 17 hours at room temperature. The mixture was concentrated under reduced pressure. The remaining foam (8.2 g) was dissolved in a mixture of dichloromethane (10 mL) and trifluoroacetic acid (20 mL). After stirring at room temperature for 6.5 hours the solution was concentrated under reduced pressure. Toluene (25 mL) was added to the remaining oil and the mixture was concentrated a second time. A mixture of ethanol (20 mL) and anhydrous hydrochloric acid in diethyl ether (2M, 20 mL) was added and the solution was concentrated a third time. After drying under high vacuum for 2 hours at room temperature, the experiment produced (±)-Ketoprofen-L-Threonine ester, hydrochloride (mix of diastereomers, 7.11 g, 98% crude yield) as an off-white solid. The crude mixture of diastereomers (7.0 g) was crystallized 3 times from acetonitrile (200 mL). After the third crystallization, the remaining white solid was dried under high vacuum at 50° C. until the weight was constant (4 hours). The experiment produced L-Threonine-S(+)-Ketoprofen ester, hydrochloride SPI0018A (2.2 g, 30% yield from SPI001801).

SPI0018A

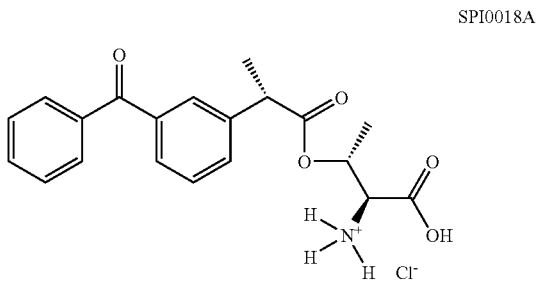

2(S)-Amino-3(R)-[2(S)-(3-benzoyl-phenyl)-propionyloxy]-butyric acid, hydrochloride (L-Threonine-S(+)-Ketoprofen ester, hydrochloride):

$^1$H NMR (300 MHz, DMSO): δ=14.08 (br s, 1H), 8.72 (br s, 3H), 7.74-7.51 (m, 9H), 5.29 (t, 1H, J=4.5 Hz), 4.16 (m, 1H), 3.97 (q, 1H, J=6.3 Hz), 1.42 (d, 3H, J=6.9 Hz), 1.23 (d, 3H, J=6.3 Hz).

$^{13}$C NMR (75 MHz, DMSO): δ=195.34, 172.26, 168.21, 140.42, 137.05, 136.74, 132.66, 131.66, 129.48, 128.73, 128.49, 128.30, 68.23, 55.31, 44.00, 18.44, 16.45.

CHN analysis:

calc.: C, 61.30; H, 5.66; N, 3.57. found: C, 61.02; H, 5.58; N, 3.58.

HPLC analysis:

98.28% purity; r.t.=25.14 min.; 55% DIUF water (0.1% TFA)/45% methanol; 1 mL/min; 36.4 C; Luna C18, 5u column (serial #211739-42), 4.6×250 mm; 20 ul injection.

Optical rotation: +27.0 (20 C, 174.4 mg/10 mL ethanol, 589 nm); Melting Point: 166-167° C.

Preparation of the S-(+)-Ketoprofen-L-Threonine Ester, Hydrochloride Standard.

(+)-Ketoprofen (1.87 g, 7.74 mmol), N-t-butylcarbonyl-L-Threonine t-butyl ester (Boc-Thr-OtBu, 2.25 g, 8.14 mmol), 1-(3-dimethylaminopropyl)-3-ethylcarbodiimide, hydrochloride (EDC, 1.65 g, 8.60 mmol), and 4-(N,N-dimethylamino)-pyridine (DMAP, 0.1 g) were dissolved in dichloromethane (25 mL) at room temperature, under an argon atmosphere. After stirring for 4 hours, the dichloromethane layer was washed with water (25 mL). After drying for one hour over sodium sulfate (5 g), filtration, and concentration under reduced pressure, the remaining oil was used without purification. The procedure generated the protected L-Threonine-(+)-Ketoprofen ester as a clear oil (4.01 g, ±100% yield).

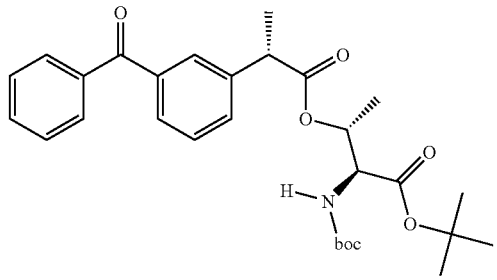

$^1$H NMR (300 MHz, CDCl$_3$): δ=7.81-7.42 (m, 9H), 5.43 (m, 1H), 5.10 (d, 1H, J=9.3), 4.29 (d, 1H, J=9.6 Hz), 3.75 (q, 1H, J=7.2 Hz), 1.50-1.42 (m, 21H), 1.18 (d, 3H, 6.3 Hz).

$^{13}$C NMR (75 MHz, CDCl$_3$): δ=196.4, 172.79, 168.99, 155.94, 140.44, 137.99, 137.51, 132.59, 131.50, 130.13, 129.31, 129.25, 129.15, 128.66, 128.40, 82.68, 80.24, 71.37, 57.71, 45.43, 28.53, 28.10, 18.99, 16.96.

The protected (S)-Ketoprofen-L-Threonine ester (3.92 g, 7.66 mmol) was dissolved in anhydrous hydrochloric acid in diethyl ether (2M, 50 mL) and stirred for 17 hours at room temperature. The mixture was concentrated under reduced pressure. The remaining foam (3.4 g) was dissolved in a mixture of dichloromethane (20 mL) and trifluoroacetic acid (20 mL). After stirring at room temperature for 6.5 hours the solution was concentrated under reduced pressure. Toluene (25 mL) was added to the remaining oil and the mixture was concentrated a second time. A mixture of ethanol (20 mL) and anhydrous hydrochloric acid in diethyl ether (2M, 20 mL) was added and the solution was concentrated a third time. After drying under high vacuum for 2 hours at room temperature, the experiment produced S(+)-Ketoprofen-L-Threonine ester, hydrochloride (3.05 g crude) as an off-white solid. The crude material was stirred with acetone (50 mL) for 2 hours at room temperature under an argon atmosphere. The remaining white solid was filtered and dried under high vacuum at 50° C. until the weight was constant (4 hours). The experiment produced L-Threonine-S(+)-Ketoprofen ester, hydrochloride (2.04 g, 67% yield).

$^1$H NMR (300 MHz, DMSO): δ=14.08 (br s, 1H), 8.72 (br s, 3H), 7.74-7.51 (m, 9H), 5.29 (t, 1H, J=4.5 Hz), 4.16 (m, 1H), 3.97 (q, 1H, J=6.3 Hz), 1.42 (d, 3H, J=6.9 Hz), 1.23 (d, 3H, J=6.3 Hz).

$^{13}$C NMR (75 MHz, DMSO): δ=195.34, 172.26, 168.21, 140.42, 137.05, 136.74, 132.66, 131.66, 129.48, 128.73, 128.49, 128.30, 68.23, 55.31, 44.00, 18.44, 16.45.

HPLC analysis:

99.43% purity; r.t.=25.14 min.; 55% DIUF water (0.1% TFA)/45% methanol; 1 mL/min; 36.4 C; Luna C18, 5u column (serial #211739-42), 4.6×250 mm; 20 ul injection.

Optical rotation: +27.1° (20 C, 177.8 mg/10 mL ethanol, 589 nm); Melting Point: 166-167° C.

Preparation of the (±)Ketoprofen-L-Serine Ester, Hydrochloride (±)-Ketoprofen (7.30 g, 28.7 mmol), N-t-butylcarbonyl-L-serine t-butyl ester (Boc-Ser-OtBu, (7.50 g, 28.7 mmol), 1-(3-dimethylaminopropyl)-3-ethylcarbodiimide, hydrochloride (EDC, 5.5 g, 28.7 mmol), and 4-(N,N-dimethylamino)-pyridine (DMAP, 0.12 g) were dissolved in dichloromethane (50 mL) at room temperature, under an argon atmosphere. After stirring for 3 hours, the dichloromethane layer was washed with water (50 mL), 5% hydrochloric acid (2×25 mL), water (25 mL), saturated sodium bicarbonate (2×25 mL), and water (50 mL). After drying for one hour over sodium sulfate (5 g), filtration, and concentration under reduced pressure, the remaining foam was used without purification. The procedure generated the protected L-serine-(±)-Ketoprofen ester as a clear foam (13.72 g, 96% yield).

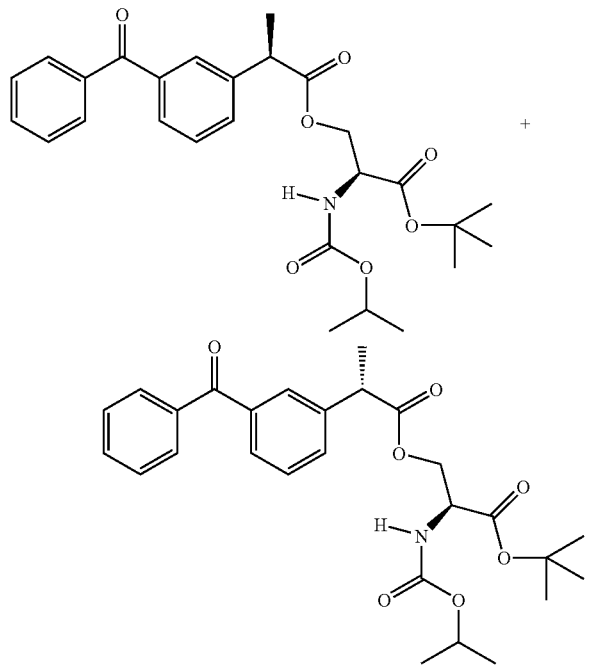

3-[2(R,S)-(3-Benzoyl-phenyl)-propionyloxy]-2(S)-tert-butoxycarbonylamino-propionic acid tert-butyl ester $^1$H NMR (300 MHz, CDCl$_3$): δ=7.77-7.38 (m, 9H), 5.29 (d, ½H, J=6.9 Hz), 5.13 (d, ½H, J=6.9 Hz), 4.44-4.30 (m, 3H), 3.78 (q, 1H, J=7 Hz), 1.50 (d, 3H, J=7 Hz), 1.39 (m, 18H).

$^{13}$C NMR (75 MHz, CDCl$_3$): δ=196.13, 173.37, 168.37, 154.99, 140.40, 137.89, 132.50, 131.44, 130.01, 129.25, 129.14, 128.53, 128.29, 82.72, 80.03, 65.22, 64.91, 53.62, 53.40, 45.29, 28.41, 28.02, 27.91, 18.59, 18.50.

The protected (R,S)-Ketoprofen-L-serine ester (13.6 g, 127.31 mmol) was dissolved in anhydrous hydrochloric acid in diethyl ether (2M, 100 mL) under an argon atmosphere, at room temperature. The mixture was allowed to stir for 23 hours at room temperature when dichloromethane was added (100 mL). After 48 hours, the mixture was concentrated under reduced pressure. The remaining light yellow foam (9.0 g) was dissolved in a mixture of dichloromethane (200 mL) and DIUF water (50 mL). After mixing at room temperature, the layers were separated. The dichloromethane layer was acidified with 2N hydrochloric acid in ether (5 mL) dried over sodium sulfate (10 g) filtered and concentrated under reduced pressure. The remaining foam (6.4 g) was stirred with dichloromethane (40 mL) for 30 minutes at room temperature under an argon atmosphere. Diethyl ether was added (20 mL) and the mixture was allowed to stir for 2 hours at room temperature. After 2 hours the solids were filtered and dried under high vacuum at room temperature until a constant weight was obtained. The experiment produced L-serine-R,S(±)-Ketoprofen ester, hydrochloride (2.5 g, 22% yield).

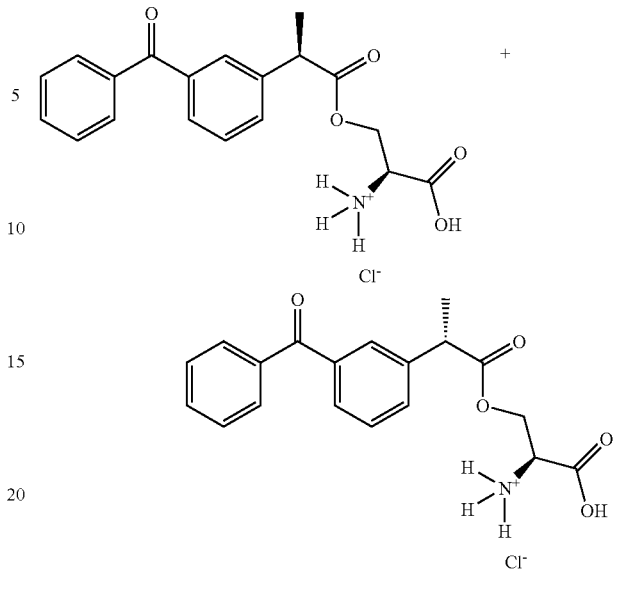

2(S)-Amino-3-[2(R,S)-(3-benzoyl-phenyl)-propionyloxy]-propionic acid, hydrochloride:

H NMR (300 MHz, DMSO): δ=8.79 (br s, 3H), 8.72 (br s, 3H), 7.76-7.54 (m, 9H), 4.57 (m, 1H), 4.42-4.28 (m, 2H), 4.01 (m, 1H), 1.46 (d, 3H, J=6 Hz).

$^{13}$C NMR (75 MHz, DMSO): δ=195.33, 172.92, 168.01, 167.96, 140.50, 140.39, 136.97 (d), 136.75, 132.66, 131.93 (d), 129.55, 128.65 (d), 128.49 (d), 62.18, 51.35 (d), 44.07, 18.62, 18.41.

HPLC analysis:

98.99% purity; r.t.=9.205 min. (broad peak); 55% DIUF water (0.1% TPA)/45% methanol; 1 mL/min; 36.4 C; Luna C18, 5u column (serial #211739-42), 4.6×250 mm; 20 ul injection.

CHN analysis:

calc.: C, 60.40; H, 5.34; N, 3.71. found: C, 60.15; H, 5.32; N, 3.72.

Melting Point: 116-120° C. (uncorrected)

Preparation of the (±)Ketoprofen-L-Hydroxyproline Ester, Hydrochloride (±)-Ketoprofen (6.70 g, 26.3 mmol), N-t-butylcarbonyl-trans-L-hydroxyproline-t-butyl ester (Boc-Hyp-OtBu, 7.40 g, 25.7 mmol), 1-(3-dimethylaminopropyl)-3-ethylcarbodiimide, hydrochloride (EDC, 5.25 g, 27.3 mmol), and 4-(N,N-dimethylamino)-pyridine (DMAP, 0.10 g) were dissolved in dichloromethane (50 mL) at room temperature, under an argon atmosphere. After stirring for 3.5 hours, the dichloromethane layer was washed with water (50 mL), 5% hydrochloric acid (2×25 mL), water (25 mL), saturated sodium bicarbonate (2×25 mL), and water (50 mL). After drying for one hour over sodium sulfate (5 g), filtration, and concentration under reduced pressure, the remaining light green oil (13.30 g) was used purified by column chromatography on silica gel (120 g), eluting with heptane/ethyl acetate (2:1). After combining the product containing fractions, concentration under reduced pressure and drying under high vacuum, the procedure generated the protected L-hydroxyproline-(±)-Ketoprofen ester as a clear oil (5.50 g, 41% yield).

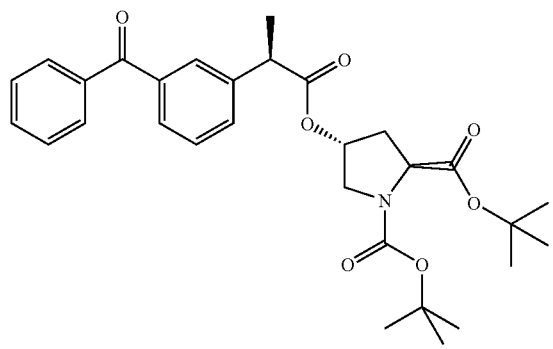

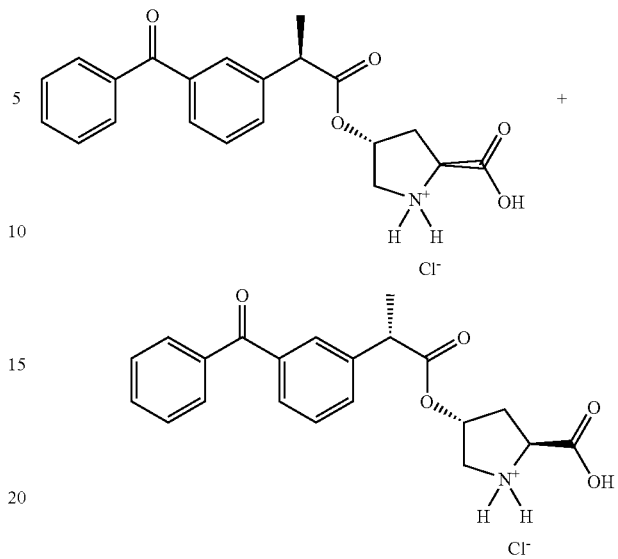

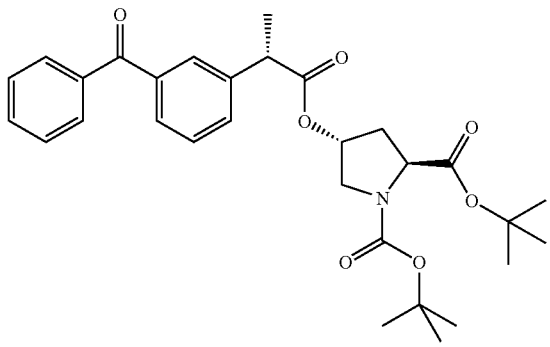

4(R)-[2(R,S)-(3-Benzoyl-phenyl)-propionyloxy]-pyrrolidine-1,2(S)-dicarboxylic acid di-tert-butyl ester:

$^1$H NMR (300 MHz, CDCl$_3$): δ=7.77-7.38 (m, 9H), 5.29 (d, ½H, J=6.9 Hz), 5.13 (d, ½H, J=6.9 Hz), 4.44-4.30 (m, 3H), 3.78 (q, 1H, J=7 Hz), 1.50 (d, 3H, J=7 Hz), 1.39 (m, 18H).

$^{13}$C NMR (75 MHz, CDCl$_3$): δ=196.25, 173.43 (d), 171.46 (d), 153.66 (d), 140.35, 138.00, 137.47, 132.55, 131.38, 130.05, 129.13, 128.67, 128.30, 81.55, 80.37 (d), 73.31, 72.48, 58.56, 51.86 (d), 45.43, 36.68 (d), 28.49, 28.18, 18.60.

The protected (R,S)-Ketoprofen-L-hydroxyproline ester (3.30 g, 6.31 mmol) was dissolved in anhydrous hydrochloric acid in diethyl ether (2M, 20 mL) under an argon atmosphere, at room temperature. After 72 hours, the mixture was concentrated under reduced pressure. The remaining light yellow foam (2.6 g) was dissolved in a mixture of dichloromethane (50 mL) and DIUF water (10 mL). After mixing at room temperature, the layers were separated. The dichloromethane layer was acidified with 2N hydrochloric acid in ether (5 mL) dried over sodium sulfate (5 g) filtered and concentrated under reduced pressure. The remaining foam (2 g) was stirred with diethyl ether (20 mL) for 30 minutes at room temperature under an argon atmosphere. The solids were filtered and dried under high vacuum at room temperature until a constant weight was obtained. The experiment produced L-hydroxyproline-R,S(±)-Ketoprofen ester, hydrochloride (1.2 g, 48% yield).

4(R)-[2(R,S)-(3-Benzoyl-phenyl)-propionyloxy]-pyrrolidine-2(S)-carboxylic acid, hydrochloride:

H NMR (300 MHz, DMSO): δ=10.25 (br s, 2H), 7.73-7.53 (m, 9H), 5.29 (br m, 1H), 4.38 (t, ½H, J=8.1 Hx), 4.26 (t, ½H, 9 Hz), 3.95 (m, 1H), 3.60 (m, 1H), 3.28 (d, ½H, J=13 Hz), 3.16 (d, ½H, J=12 Hz), 2.37-2.20 (m, 2H), 1.45 (m, 3H).

$^{13}$C NMR (75 MHz, DMSO): δ=195.38, 172.78, 172.73, 169.16, 140.50, 140.41, 137.08, 136.77, 132.67, 132.01, 131.89, 129.52, 128.78, 128.50, 128.50, 72.87 (d), 57.60, 57.52, 50.16 (d), 44.30, 44.20, 34.26, 34.15, 18.43, 18.25.

HPLC analysis:

99.99% purity; r.t.=7.842 and 7.689 min. (broad double peak); 55% DIUF water (0.1% TFA)/45% methanol; 1 mL/min; 36.4 C; Luna C18, 5u column (serial #211739-42), 4.6×250 mm; 20 ul injection.

CHN analysis:

calc.: C, 62.45; H, 5.49; N, 3.47. found: C, 61.78; H, 5.56; N, 3.62.

Melting Point: 170-173° C. (uncorrected).

These synthetic procedures demonstrate that L-threonine is capable of readily separating Ketoprofen into its respective enantiomeric esters, while other the hydroxyl amino acids such as Hydroxyproline or serine did not do so readily.

Synthesis of Keotorlac-L-Threonine Ester and Human Trials:

Overview:

The procedure for the synthesis of the L-threonine ester of Ketorolac is outlined in Synthetic Sequence section. The complete procedure and analytical data is given in the Experimental Section. In general, (±)-Ketorolac was extracted from the tromethamine salt (10 g) and coupled with N-boc-L-threonine t-butyl ester (1 equivalent) with 1-(3-dimethylaminopropyl)-3-ethylcarbodiimide, hydrochloride (EDCI) in the presence of a catalytic amount of 4-(N,N-dimethylamino)-pyridine (DMAP). The crude protected L-threonine-(±)-Ketorolac ester was purified by flash chromatography. The protecting groups were removed by treatment with trifluoroacetic acid. The mixture of L-threonine-R,S(±)-Ketorolac ester salts was separated by crystallization from acetonitrile/acetone. A sample of S(−)-Ketorolac L-threonine ester, hydrochloride (2.1 g) separated from the mixture was shipped to Signature for testing.

Synthetic Sequence:

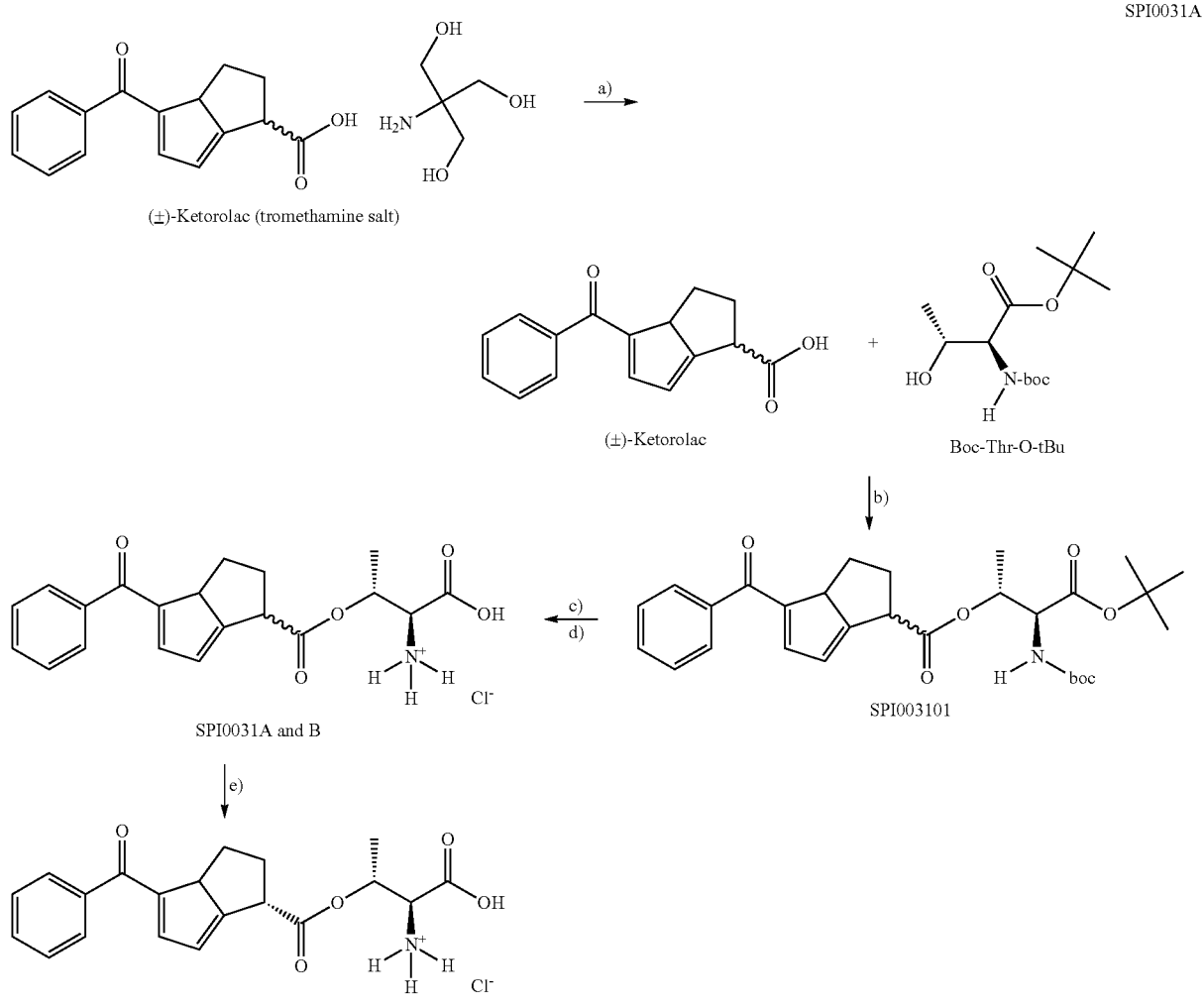

SPI0031A

Synthesis of the L-threonine esters of (±)-Ketorolac: a) AcOH/H₂O, CH₂Cl₂; b) EDC, DMAP, CH₂Cl₂; c) TFA; d) HCl, ethanol; e) ACN-acetone (crystallization).

Experimental Section:

The synthesis of SPI0031A was conducted in a single batch. The procedure was later repeated to ensure reproducibility. Reagents mentioned in the experimental section were purchased at the highest obtainable purity from Cayman Chemical, Sigma-Aldrich, Acros, or Bachem, except for solvents, which were purchased from either Fisher Scientific or Mallinkrodt.

Preparation and Separation of S(−)-Ketorolac L-Threonine Ester, Hydrochloride (SPI0031A).

(±)-Ketorolac tromethamine salt (10 g, Cayman Chemical) was dissolved in water (100 mL), acetic acid (20 mL), and dichloromethane (50 mL). After mixing for ten minutes, the layers were separated and the water fraction was extracted two additional times with dichloromethane (50 mL). The dichloromethane fractions were combined, dried over sodium sulfate, filtered, concentrated, and dried under high vacuum at room temperature until a constant weight was obtained. The procedure generated (±)-Ketorolac (6.78 g, 100% yield) as an off-white solid.

$^1$H NMR (300 MHz, CDCl$_3$): δ=9.62 (1H, br s), 7.80 (2H, d, J=6.9 Hz), 7.55-7.42 (3H, m), 6.84 (1H, d, J=4.0 Hz), 6.15 (1H, d, J=4.0 Hz), 4.62-4.41 (2H, m), 4.10 (1H, dd, J=8.4, 5.7 Hz), 2.97-2.75 (2H, m).

$^{13}$C NMR (75 MHz, CDCl$_3$): δ=185.25, 176.69, 142.04, 139.05, 131.61, 129.02, 128.26, 127.31, 125.43, 103.63, 47.77, 42.64, 31.20.

(±)-Ketorolac (6.80 g, 26.6 mmol), N-tert-butylcarbonyl-L-threonine tert-butyl ester (Boc-Thr-OtBu, 7.33 g, 26.6 mmol), 1-(3-dimethylaminopropyl)-3-ethylcarbodiimide, hydrochloride (EDCI, 5.50 g, 28.6 mmol), and 4-(N,N-dimethylamino)-pyridine (DMAP, 0.10 g) were dissolved in dichloromethane (75 mL) at room temperature, under an argon atmosphere. After stirring for 6 hours, the dichloromethane solution was washed with water (50 mL), saturated sodium bicarbonate 50 mL), and water (50 mL). After drying the dichloromethane solution for one hour over sodium sulfate (10 g), filtration, and concentration under reduced pressure, the remaining brown oil (14.55 g) was purified by column chromatography on silica gel (250 g), eluting with heptane/ethyl acetate (1:1). After combining the product containing fractions, concentration and drying under high vacuum, the procedure generated the protected L-threonine-(±)-Ketorolac ester (SPI003101) as light brown solid foam (13.53 g, 99.2% yield).

SPI003101

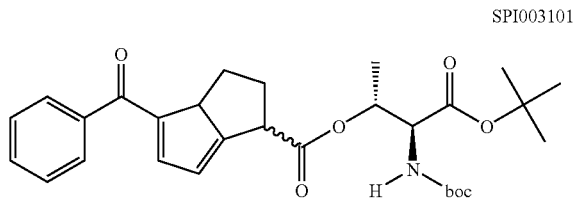

$^1$H NMR (300 MHz, CDCl$_3$): δ=7.80 (2H, m), 7.55-7.42 (3H, m), 6.81 (1H, m), 6.08 (1H, m), 5.47 (1H, m), 5.17 (1H, m), 4.60-4.34 (3H, m), 4.01 (1H, m), 2.90-2.70 (2H, m), 1.48-1.32 (21H, m).

$^{13}$C NMR (75 MHz, CDCl$_3$): δ=184.85, 169.91, 168.91, 155.84, 141.91, 139.12, 131.41, 128.86, 128.13, 127.18, 124.99, 103.56, 103.13, 82.76, 80.23, 72.15, 72.00, 57.64, 47.62, 42.71, 42.53, 32.02, 31.11, 28.44, 28.02, 17.03, 14.33.

The protected (±)-Ketorolac L-threonine ester SPI003101 (13.50 g, 26.33 mmol) was dissolved in trifluoroacetic acid (50 mL) under an argon atmosphere, at room temperature. The mixture was allowed to stir for 7 hours at room temperature under an argon atmosphere. The brown solution was concentrated under reduced pressure and dried under high vacuum at room temperature until a constant weight was achieved. The remaining brown solid (10.2 g) was stirred in acetone (250 mL) at room temperature for 3 hours. The white precipitate that fowled was filtered and dried under high vacuum. The remaining solid (5.70 g) was dissolved in a minimal amount of DIUF water (5-10 mL) and a 1:1 mixture of acetonitrile-acetone (100 mL) was added drop-wise over 1 hour while stirring at room temperature. After the addition was complete, the mixture was stored for 2 hours at room temperature. The white precipitate that formed was filtered and dried under high vacuum at room temperature to a constant weight. The white solid (3.0 g) was purified a final time by dissolving in DIUF water (5 mL). Most of the water was removed under reduced pressure to generate a thick, clear oil. Acetone (100 mL) was added to the oil in a drop-wise fashion over 30 minutes while stirring under an argon atmosphere. The mixture was stored for 3 hours at ±10° C. The precipitate was filtered and dried under high vacuum at room temperature until the weight was constant. The experiment produced S(−)-Ketorolac-L-threonine ester, hydrochloride SPI10031A (2.32 g, 22.4% yield based on SPI003101, 98.12% purity by HPLC) as white solid.

$^1$H NMR (300 MHz, DMSO): δ=8.80 (3H, br s), 7.73 (2H, d, 7.5 Hz), 7.61-7.46 (3H, m), 6.77 (1H, d, J=3.9 Hz), 6.16 (1H, d, J=3.9 Hz), 5.33 (1H, m), 4.42-4.22 (4H, m), 2.76 (2H, m), 1.35 (3H, d, J=6.6 Hz).

$^{13}$C NMR (75 MHz, DMSO): δ=183.41, 169.64, 168.19, 142.32, 138.59, 131.44, 128.35, 128.26, 126.22, 124.27, 103.18, 68.84, 55.31, 47.34, 41.83, 30.18, 16.59.

CHN analysis:
calc.: C, 58.09; H, 5.39; N, 7.13; Cl, 9.02 (C$_{19}$H$_{21}$ClN$_2$O$_5$).
found: C, 58.61; H, 5.26; N, 7.10; Cl, 8.16.

HPLC analysis:
98.12% purity, r.t.=19.617 min, sample dissolved in DIUF water/ACN, 50% DIUF water (0.1% TFA)/50% ACN, Gemini C18 (#262049-2), 5u, 250×4.6 mm, 1 mL/min., 37° C., 20 uL inj. vol., SPD-10Avp, ch1-210 nm.

Specific rotation: −108 deg (25° C., 52.5 mg/5 mL water, 589 nm)

Melting Point: 155-157° C. (decomposed)

Large negative specific rotation is consistent with the S(−) Ketorolac moiety.

Synthesis of Fibric Acid Threonine Derivatives

Overview:

The procedure for the synthesis of the L-threonine esters of fenofibric acid is outlined in the Synthetic Sequence section. The complete procedure and analytical data is given in the Experimental Section. In general, fenofibric acid (100 g batches) was prepared from 4-chloro-4'-hydroxybezophenone in accordance with the known procedure. Fenofibric acid was coupled with the t-butyl esters of N-boc protected amino acid (L-threonine) using EDC as the coupling agents and a catalytic amount of DMAP. The protecting groups were removed at low temperature (5° C., 3-6 days) with a mixture of hydrochloric acid in acetic acid (1M) with dichloromethane. The amino acid ester salts of fenofibric acid were purified by crystallization from ethyl acetate, dried under high vacuum, and shipped to Signature Pharmaceuticals Inc., after analysis by NMR, HPLC, CHN, and melting point. This procedure was repeated substituting L-serine and L-hydroxyproline for L-Threonine for comparative purposes.

Synthetic Sequence:

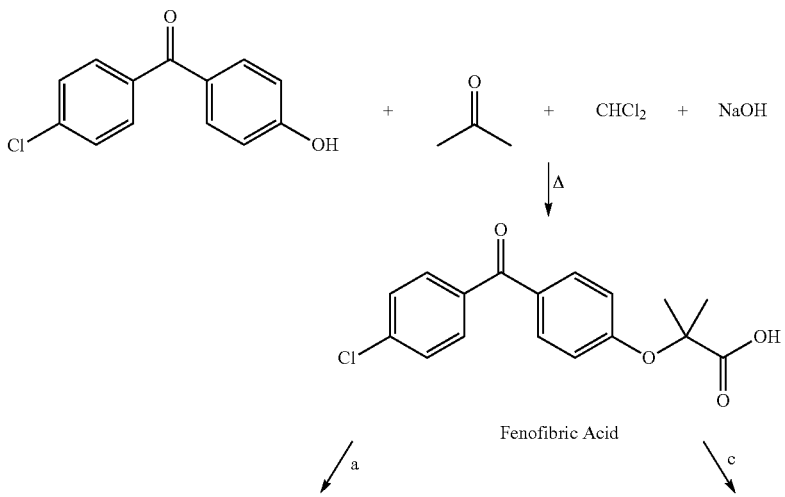

-continued

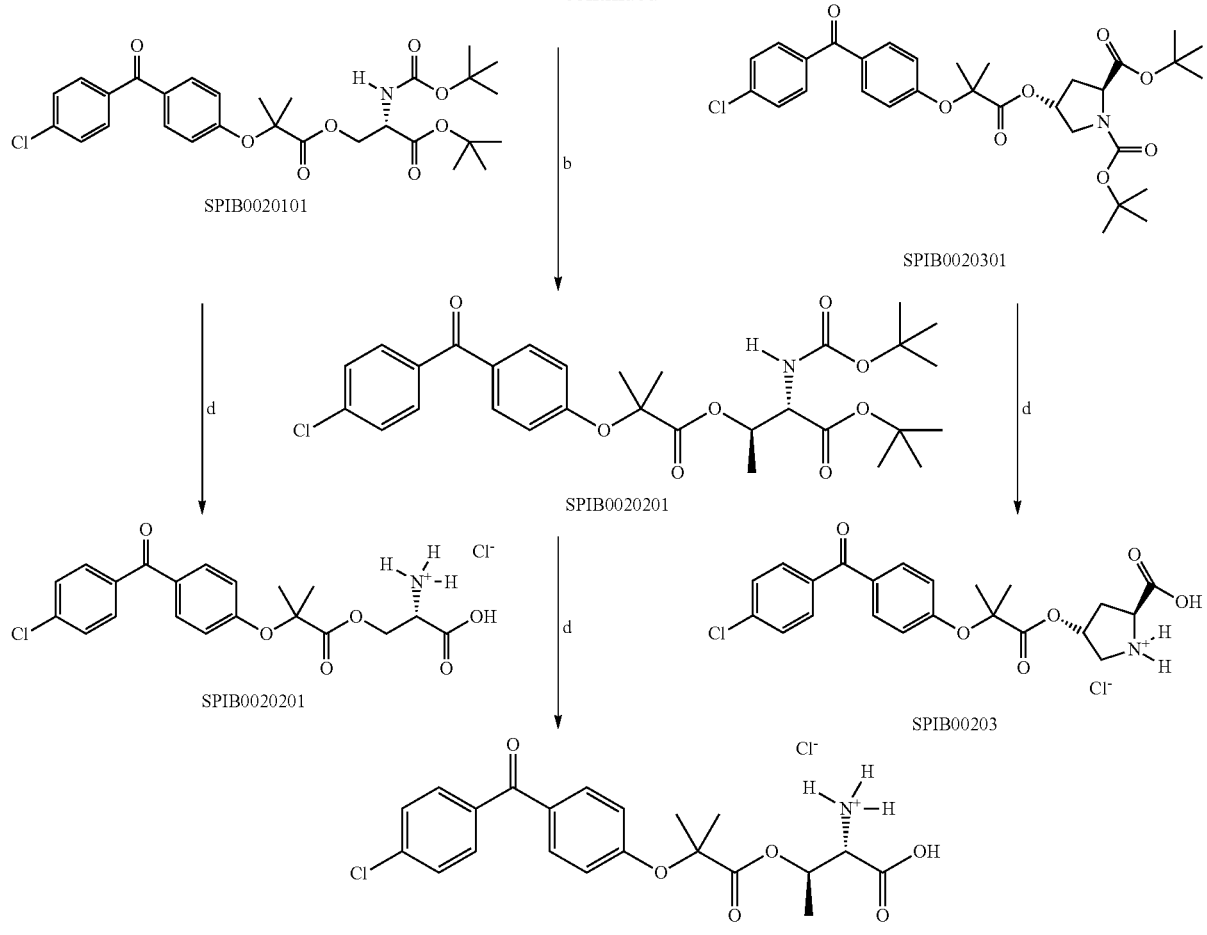

Synthesis of the L-serine, L-threonine, and L-hydroxyproline esters of fenofibric acid: a) Boc-Ser-OtBu, EDC, DMAP, $CH_2Cl_2$; b) Boc-Thr-OtBu, EDC, DMAP, $CH_2Cl_2$; c) Boc-Hyp-OtBu, EDC, DMAP, $CH_2Cl_2$; d) HCl, AcOH, $CH_2Cl_2$.

Experimental Section:

The synthesis of SPIB00201, SPIB00202 and SPIB00203 was conducted in one or two batches. Reagents mentioned in the experimental section were purchased at the highest obtainable purity from Lancaster, Sigma-Aldrich, Acros, or Bachem, except for solvents, which were purchased from either Fisher Scientific or Mallinkrodt.

Synthesis of Fenofibric Acid:

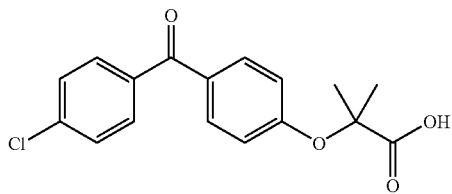

A mixture of 4-chloro-4'-hydroxybezophenone (116 g, 0.500 mole) and sodium hydroxide (120 g, 3.00 mole) in acetone (1 L) was heated to reflux for 2 hours. The heating was stopped and the heating source was removed. A mixture of chloroform (179 g, 1.50 mole) in acetone (300 mL) was added drop-wise. The reaction mixture was stirred overnight without heating. The mixture was heated to reflux for 8 hours and then allowed to cool to room temperature. The precipitate was removed by filtration and washed with acetone (100 mL). The filtrate was concentrated under reduced pressure to give a brown oil. Water (200 mL) was added to the brown oil and was acidified (to pH=1) with 1N hydrochloric acid. The precipitate, which formed was filtered and dried under high vacuum. The remaining yellow solid (268 g) was recrystallized from toluene in 4 batches (400 mL toluene each). After filtration and drying under high vacuum, the experiment produced fenofibric acid (116 g, 73% yield) as a light yellow solid.

$^1$H NMR (300 MHz, DMSO-$d_6$): δ=13.22 (1H, s, br), 7.72 (4H, d, J=8.4 Hz), 7.61 (2H, d, J=7.8 Hz), 6.93 (2H, d, J=7.8 Hz), 1.60 (6H, s).

$^{13}$C NMR (75 MHz, DMSO-$d_6$): δ=192.96, 174.18, 159.35, 136.84, 136.12, 131.67, 131.02, 129.12, 128.43, 116.91, 78.87, 25.13.

2) SPIB00201: L-Serine-Fenofibric Acid Ester

To a mixture of fenofibric acid (11.6 g, 36.3 mmol), N-carbobenzyloxy-L-serine t-butyl ester (Boc-Ser-OtBu, 8.62 g, 33.0 mmol), EDC (7.59 g, 39.6 mmol), and DMAP (484 mg, 3.96 mmol) cooled in an ice-water bath was added anhydrous dichloromethane (150 mL) dropwise. After addition was complete, the ice bath was removed and the reaction mixture was stirred under an argon atmosphere at room temperature for 20 hours. After 20 hours, the additional dichloromethane (200 mL) was added and the solution was washed with water (2×200 mL) and brine (200 mL). After drying over sodium sulfate and filtration, the solution was concentrated under reduced pressure. The remaining yellow oil (21.2 g) was purified by column chromatography on silica gel (400 g, 0.035-0.070 mm, 6 nm pore diameter), eluting with heptane/ethyl acetate (3:1). After concentration of the product-containing fractions under reduced pressure and drying under high vacuum until the weight was constant, the experiment produced the protected L-serine-fenofibric acid ester SPIB0020101 (16.2 g, 87% yield) as a light yellow oil.

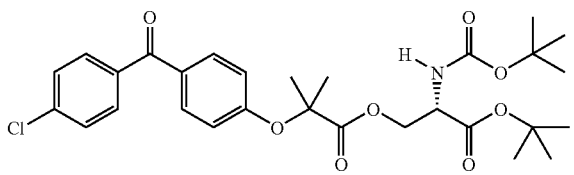

$^1$H NMR (300 MHz, CDCl$_3$): δ=7.75 (2H, d, 9.0 Hz), 7.72 (2H, d, J=9.0 Hz), 7.45 (2H, d, J=8.7 Hz), 6.86 (2H, d, J=8.7 Hz), 5.04 (1H, d, J=6.9 Hz), 4.55-4.42 (3H, m), 1.66 (3H, s), 1.65 (3H, s), 1.43 (9H, s), 1.39 (9H, s).

$^{13}$C NMR (75 MHz, CDCl$_3$): δ=193.92, 172.99, 168.07, 159.24, 154.87, 138.24, 136.19, 131.94, 131.06, 130.40, 128.41, 117.26, 82.88, 80.13, 79.24, 65.44, 53.44, 28.27, 27.92, 25.70, 25.30.

To a stirred solution of the protected L-serine-fenofibric acid ester SPIB0020101 (16.2 g, 28.8 mmol) in anhydrous dichloromethane (100 mL) cooled to 5° C., under an argon atmosphere was added a solution of hydrogen chloride in acetic acid (400 mL, 1M, 400 mmol) drop-wise. The reaction mixture stirred for 3 days at 5° C. After three days the mixture was concentrated under reduced pressure and dried under high vacuum to remove acetic acid. To the remaining light yellow oil (24.7 g) was added ethyl acetate (100 mL). The solution was concentrated and dried a second time. To the remaining light yellow oil (17.0 g) was added ethyl acetate (65 mL). The mixture was heated to reflux for 5 minutes and cooled to room temperature. The precipitate was removed by filtration and dried under high vacuum overnight at room temperature, then at 43° C. for one hour. The experiment produced the L-serine-fenofibric acid ester, hydrochloride SPIB00201 (7.66 g, 60% yield) as a white solid.

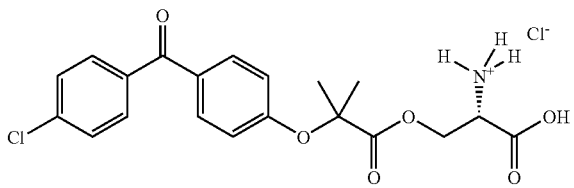

$^1$H NMR (300 MHz, DMSO-d$_6$): δ=14.12 (1H, s, br), 8.77 (3H, s, br), 7.72 (4H, m), 7.62 (2H, d, J=8.4 Hz), 6.92 (2H, d, J=9.0 Hz), 4.62 (1H, dd, J=12.0, 4.2 Hz), 4.50 (1H, dd, J=12.0, 2.4 Hz), 4.41 (1H, m), 1.64 (3H, s), 1.63 (3H, s).

$^{13}$C NMR (75 MHz, DMSO-d$_6$): δ=193.06, 171.70, 168.05, 158.72, 136.93, 136.06, 131.73, 131.09, 129.62, 128.49, 117.64, 79.02, 62.99, 51.11, 25.04, 24.94.

HPLC analysis:

100% purity; r.t.=4.361 min.; 55% TFA (0.1%), 45% ACN; 1 mL/min; 32.3 C, Luna C18, serial #167917-13; 20 ul inj., NB275-49.

CHN analysis:

calc.: C, 54.31; H, 4.79; N, 3.17. found: C, 54.37; H, 4.78; N, 3.12.

Melting point: 151° C. (dec.)

SPIB00202: L-Threonine-Fenofibric Acid Ester

To a mixture of fenofibric acid (25.5 g, 79.9 mmol), N-carbobenzyloxy-L-threonine t-butyl ester (Boc-Thr-OtBu, 20.0 g, 72.6 mmol), EDC (16.7 g, 87.1 mmol), and DMAP (1.06 g, 8.71 mmol) cooled in an ice-water bath was added anhydrous dichloromethane (200 mL), dropwise. After the addition was complete, the ice bath was removed and the reaction mixture was stirred under an argon atmosphere at room temperature for 20 hours. After 20 hours, additional EDC (1.39 g, 7.26 mmol) was added and the experiment was allowed to stir over the weekend at room temperature under an argon atmosphere. After 4 days, additional dichloromethane (300 mL) was added and the solution was washed with water (300 mL) and brine (300 mL). After drying over sodium sulfate and filtration, the solution was concentrated under reduced pressure. The remaining yellow oil (53.5 g) was purified by column chromatography on silica gel (500 g, 0.035-0.070 mm, 6 nm pore diameter), eluting with heptane/ethyl acetate (3:1). After concentration of the product-containing fractions under reduced pressure and drying under high vacuum until the weight was constant, the experiment produced the protected L-threonine-fenofibric acid ester SPIB0020201 (34.1 g, 82% yield) as a white foam.

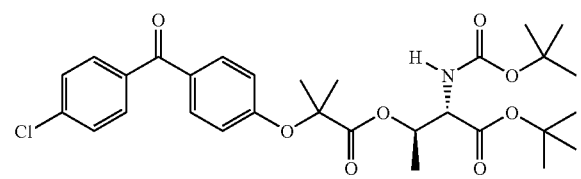

$^1$H NMR (300 MHz, CDCl$_3$): δ=7.74 (2H, d, J=8.4 Hz), 7.72 (21-1, d, J=8.4 Hz), 7.45 (2H, d, J=8.4 Hz), 6.87 (2H, d, J=8.4 Hz), 5.47 (1H, m), 4.98 (1H, d, J=9.9 Hz), 4.31 (1H, d, J=9.9 Hz), 1.65 (3H, s), 1.64 (3H, s), 1.45 (9H, s), 1.42 (9H, s), 1.22 (3H, d, 6.3 Hz).

$^{13}$C NMR (75 MHz, CDCl$_3$): δ=193.94, 172.14, 168.70, 159.26, 155.62, 138.28, 136.18, 131.90, 131.08, 130.37, 128.43, 117.40, 82.70, 80.17, 79.38, 72.02, 57.46, 28.30, 27.99, 26.44, 24.79, 16.90.

To a stirred solution of the protected L-threonine-fenofibric acid ester SPIB0020201 (34.1 g, 59.2 mmol) in anhydrous dichloromethane (100 mL) cooled to 5° C., under an argon atmosphere was added a solution of hydrogen chloride in acetic acid (600 mL, 1M, 600 mmol) drop-wise. The reaction mixture was kept for 6 days at 5° C. The mixture was concentrated under reduced pressure and dried under high vacuum to remove acetic acid. To the remaining white solid (45.8 g) was added ethyl acetate (500 mL). The mixture was heated to reflux for 10 minutes and cooled to room temperature. The precipitate was removed by filtration and dried under high vacuum overnight at room temperature. The experiment produced the L-threonine-fenofibric acid ester, hydrochloride SPIB00202 (26.3 g, 97% yield) as a white solid.

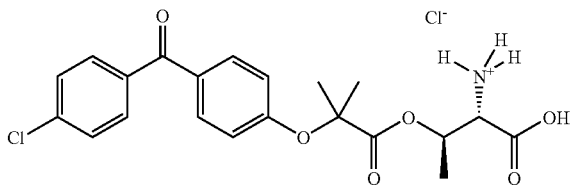

$^1$H NMR (300 MHz, DMSO-d$_6$): δ=14.10 (1H, s, br), 8.84 (3H, s, br), 7.73 (4H, m), 7.63 (2H, d, J=8.1 Hz), 6.89 (2H, d, J=8.7 Hz), 5.44 (1H, m), 4.31 (1H, s), 1.64 (3H, s), 1.62 (3H, s), 1.38 (3H, d, J=6.3 Hz).

$^{13}$C NMR (75 MHz, DMSO-d$_6$): δ=193.04, 171.00, 168.13, 158.76, 136.90, 136.08, 131.70, 131.06, 129.49, 128.48, 117.41, 78.99, 69.40, 55.21, 25.59, 24.22, 16.06.

HPLC analysis:

98.59% purity; r.t.=4.687 min.; 55% TFA (0.1%), 45% ACN; 1 mL/min; 32.3 C, Luna C18, serial #16791743; 20 ul inj., NB275-49, DAD1 B, Sig=210.4, Ref-550,100.

CHN analysis:

calc.: C, 55.27; H, 5.08; N, 3.07. found: C, 54.98; H, 5.13; N, 3.03.

Melting point: 160.5° C. (dec.)

SPIB00203: L-Hydroxyproline-Fenofibric Acid Ester

To a mixture of fenofibric acid (24.9 g, 78.1 mmol), N-carbobenzyloxy-L-hydroxyproline t-butyl ester (Boc-Hyp-OtBu, 20.4 g, 71.0 mmole), EDC (16.3 g, 85.2 mmol), and DMAP (1.04 g, 8.52 mmol) cooled in an ice-water bath was added anhydrous dichloromethane (200 mL) dropwise. After the addition was complete, the ice bath was removed and the reaction mixture was stirred under an argon atmosphere at room temperature for 20 hours. After 20 hours, additional EDC (1.63 g, 8.52 mmol) was added and the experiment was allowed to stir over the weekend at room temperature under an argon atmosphere. After 4 days the solution was washed with water (200 mL) and brine (200 mL). After drying over sodium sulfate and filtration, the solution was concentrated under reduced pressure. The remaining yellow oil (49.4 g) was purified by column chromatography on silica gel (500 g, 0.035-0.070 mm, 6 nm pore diameter), eluting with heptane/ethyl acetate (2:1). After concentration of the product containing fractions under reduced pressure and drying under high vacuum until the weight was constant, the experiment produced the protected L-hydroxyproline-fenofibric acid ester SPIB0020301 (26.4 g, 63% yield) as a colorless oil.

SPIB0020301

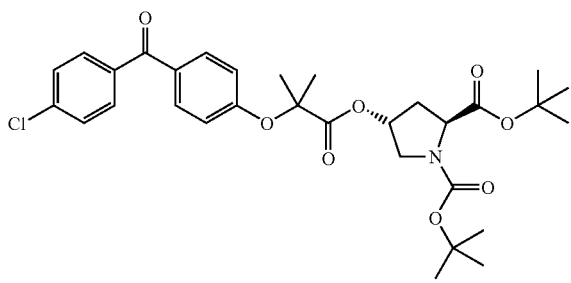

$^1$H NMR (300 MHz, CDCl$_3$): δ=7.76 (2H, d, J=8.1 Hz), 7.73 (2H, d, J=8.1 Hz), 7.46 (2H, d, J=8.1 Hz), 6.84 (2H, d, J=8.1 Hz), 5.32 (1H, m), 4.13 (0.38H, t, J=7.8 Hz), 4.00 (0.62H, t, J=7.8 Hz), 3.67 (1.62H, m), 3.46 (0.38H, d, J=12.6 Hz), 2.29 (1H, m), 2.15 (1H, m), 1.68 (3H, s), 1.66 (3H, s), 1.44-1.38 (18H, m).

$^{13}$C NMR (75 MHz, CDCl$_3$): δ 193.88, 172.98, 171.14, 159.25, 153.48, 138.23, 136.16, 131.99, 131.08, 130.36, 128.44, 117.03, 116.91, 81.48, 80.32, 80.20, 79.19, 74.03, 73.26, 58.23, 51.88, 51.58, 36.33, 35.31, 31.92, 28.29, 28.00, 25.89, 24.95.

To a stirred solution of the protected L-hydroxyproline-fenofibric acid ester SPIB0020301 (26.0 g, 44.2 mmol) in anhydrous dichloromethane (100 mL) cooled to 5° C., under an argon atmosphere was added a solution of hydrogen chloride in acetic acid (450 mL, 1M, 450 mmol) drop-wise. The reaction mixture stirred for 4 days at 5° C. After four days the mixture was concentrated under reduced pressure and dried under high vacuum to remove acetic acid. To the remaining yellow oil (31.5 g) was added ethyl acetate (200 mL). The mixture was sonicated and then concentrated under reduced pressure and dried under high vacuum. To the remaining white solid (23.2 g) was added ethyl acetate (300 mL). The ethyl acetate mixture was heated to reflux for 10 minutes and cooled to room temperature. The precipitate was removed by filtration and dried under high vacuum overnight at room temperature. The experiment produced the L-hydroxyproline-fenofibric acid ester, hydrochloride SPIB00203 (15.8 g, 76% yield) as a white solid.

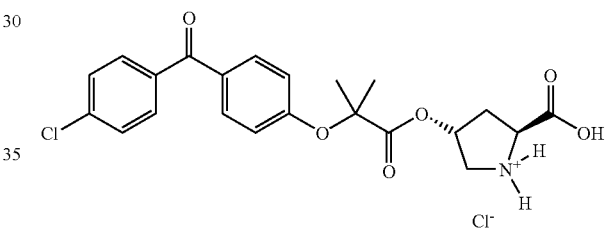

$^1$H NMR (300 MHz, DMSO-d$_6$): δ=14.07 (1H, s, br), 10.75 (1H, s, br), 9.40 (1H, s, br), 7.71 (4H, d, J=8.1 Hz), 7.60 (2H, d, J=8.1 Hz), 6.96 (2H, d, J=8.1 Hz), 5.42 (1H, m), 4.24 (1H, t, J=9.0 Hz), 3.61 (1H, dd, J=13.2, 4.2 Hz), 3.28 (1H, d, J=13.2 Hz), 2.35 (2H, m), 1.66 (3H, s), 1.64 (3H, s).

$^{13}$C NMR (75 MHz, DMSO-d$_6$): δ=193.00, 171.52, 169.14, 158.81, 136.87, 136.09, 131.81, 131.05, 129.48, 128.46, 117.28, 78.99, 73.79, 57.54, 50.23, 34.13, 25.69, 24.49.

HPLC analysis:

100% purity; r.t.=8.369 min.; 60% DIUF water (0.1% TFA)/40% acetonitrile; 1 mL/min; 36.4 C; Luna C18, 5u column (serial #191070-3), 4.6×250 mm; 20 ul injection; DAD1A, Sig=210.4, Ref=550,100.

HPLC-MS (ESI): calculated: M$^+$=431. found M+H=432.3

Melting point: 187.5° C. (dec.)

Overview: L-Threonine Derivative of Acetylsalkyelic Acid

The procedure for the synthesis of the L-Threonine of acetylsalicylic acid is outlined in the Synthetic Sequence section. The complete procedure and analytical data is given in the Experimental Section. In general, acetylsalicyloyl chloride (10 g-25 g, in batches) was coupled with the N-benzyloxy/benzyl ester protected amino acids in the presence of pyridine. Once the reactions were complete (24 to 48 hours at room temperature), the mixture was poured into ice-cold 2N hydrochloric acid. The dichloromethane fraction was then washed with sodium bicarbonate, water and brine. After drying over sodium sulfate, filtration, and concentration the crude protected amino acid esters of acetylsalicylic acid were purified by flash chromatography on silica gel. The procedure generated the protected amino acid esters of acetylsalicylic acid in yields ranging from 68% to 95%. The protecting groups were removed by hydrogenation (20 psi $H_2$) in the presence of 10% palladium on carbon. The amino acid esters of acetylsalicylic acid were extracted away from the palladium catalyst with water, concentrated, and dried. The final compounds were washed with solvent (water, dioxane, acetonitrile, and/or dichloromethane) until pure and dried under high vacuum until a constant weight was achieved. The L-serine and the L-hydroxyproline esters were prepared for comparative purposes.

Synthetic Sequence:

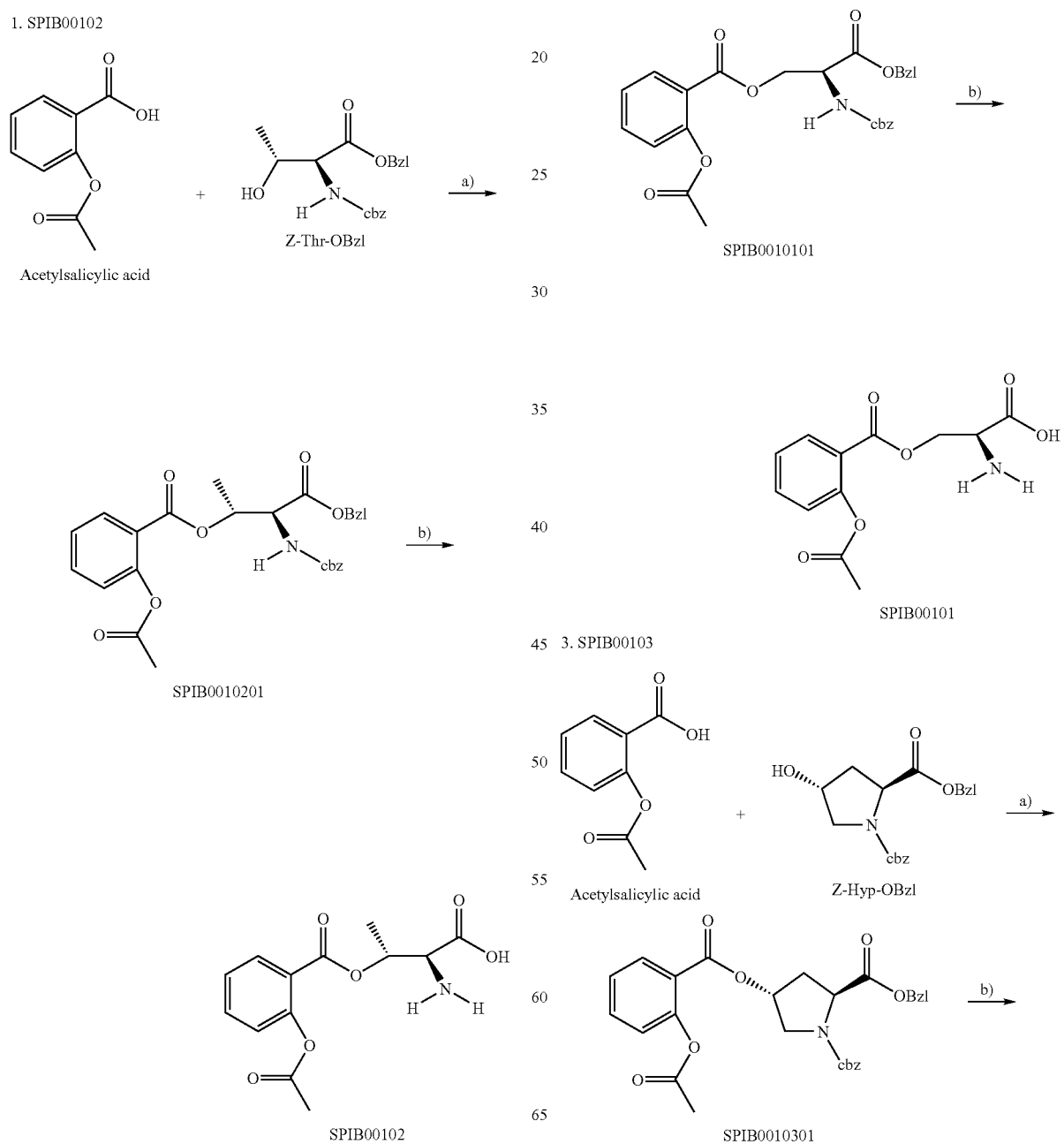

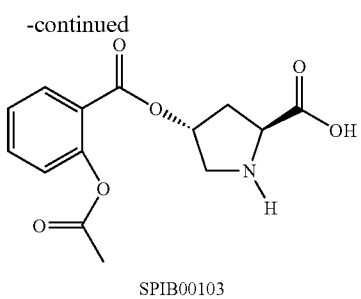

SPIB00103

Synthesis of the L-serine, L-threonine, and L-Hydroxyproline esters of acetylsalicylic acid: a) pyridine, CH₂Cl₂; b) 10% Pd/C, EtOH, EtOAc.

Experimental Section:

The synthesis of SPIB00101, SPIB00102 and SPIB00103 was conducted in one or two batches. Reagents mentioned in the experimental section were purchased at the highest obtainable purity from Lancaster, Sigma-Aldrich, Acros, or Sachem, except for solvents, which were purchased from either Fisher Scientific or Mallinckrodt.

SPIB00102: 2-O-Acetylsalicylic Acid (2S,3R)-(−)-Threonine Ester

A mixture of N-carbobenzyloxy-L-threonine benzyl ester (Z-Thr-OBzl, 21.77 g, 63.40 mmole) and pyridine (25 mL) in anhydrous dichloromethane (500 mL) was cooled in an ice bath while under a nitrogen atmosphere. Acetylsalicyloyl chloride (17.63 g, 88.76 mmole) was added and the mixture was allowed to warm to room temperature and stir overnight. After 24 hours, the mixture was poured into ice-cold 2N hydrochloric acid (400 mL). After mixing, the layers were separated and the dichloromethane fraction was washed with water (500 mL), saturated sodium bicarbonate solution (500 mL), water (500 mL), brine (500 mL) and dried over sodium sulfate (25 g). After filtration, concentration under reduced pressure, and drying under high vacuum, the remaining yellow oil (35.43 g) was purified by flash chromatography on silica gel (300 g, 0.035-0.070 mm, 6 nm pore diameter), eluting with hexanes/ethyl acetate (3:1). After concentration of the product containing fractions under reduced pressure and drying under high vacuum until the weight was constant, the experiment produced the protected acetylsalicylic-L-threonine ester SPIB0010201 (28.1 g, 88% yield) as a colorless oil.

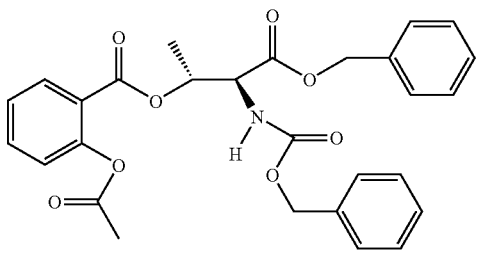

SPIB0010201

¹H NMR (300 MHz, CDCl₃): δ=7.74 (1H, d, J=7.5 Hz), 7.51 (1H, dt, J=7.5, 1.5 Hz), 7.34-7.17 (11H, m), 7.06 (1H, d, J=7.2 Hz), 5.62 (2H, m), 5.13 (4H, m), 4.65 (1H, dd, J=9.6, 2.4 Hz), 2.29 (3H, s), 1.38 (3H, d, J=6.6 Hz).

¹³C NMR (75 MHz, CDCl₃): δ=169.35, 169.22, 162.73, 156.26, 150.41, 135.79, 134.67, 133.77, 131.24, 128.35, 128.24, 128.08, 127.95, 125.78, 123.51, 122.61, 71.22, 67.72, 67.26, 57.64, 20.98, and 16.88.

The protected acetylsalicylic-L-threonine ester SPIB0010201 (14.50 g, 28.68 mmole) was dissolved in ethanol (100 mL) and ethyl acetate (100 mL) at room temperature and added to a Parr bottle that contained 10% palladium on carbon (3.0 g, 50% wet) under a nitrogen atmosphere. The nitrogen atmosphere was replaced with hydrogen gas (20 psi). After 20 hours of shaking, the palladium catalyst was removed by filtration through celite. The remaining solids (palladium/celite and product) were washed with water (600×4 mL) until the product was removed. The ethanol and water fractions were concentrated under reduced pressure at room temperature. The remaining solids were washed with water (20 mL) and dioxane (20 mL) for 48 hours. After filtration, the remaining white solid was dried at room temperature under high vacuum until the product weight was constant (16 hours). The experiment produced acetylsalicylic-L-threonine ester, SPIB00102 (4.40 g, 55% yield) as a white solid.

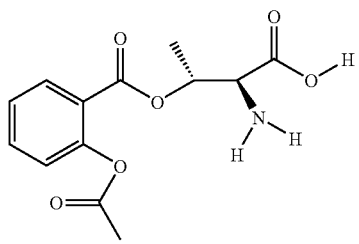

SPIB00102

¹H NMR (300 MHz, D₂O-DCl): δ=8.00 (1H, dd, J=7.8, 1.5 Hz), 7.74 (1H, dt, 1H=7.8, 1.5 Hz), 7.47 (1H, dt, J=7.8, 1.5 Hz), 7.27 (1H, dd, J=7.8, 1.5 Hz), 5.76 (1H, dq, J=6.9, 3.0 Hz), 4.49 (1H, d, 3.0 Hz), 2.39 (3H, s), 1.55 (3H, d, J=6.9 Hz).

¹³C NMR (75 MHz, D₂O-DCl): S=173.03, 168.84, 163.97, 149.56, 135.32, 131.26, 126.85, 123.48, 121.49, 69.16, 56.36, 20.45, and 15.86.

HPLC analysis:

98.7% purity; r.t=6.233 min; Luna C18 5u column (sn 167917-13); 4.6×250 mm; 254 nm; 35% MeOH/65% TFA (0.1%) pH=1.95; 35 C; 20 ul inj.; 1 ml/min; sample dissolved in mobile phase with 1 drop phosphoric acid.

CHN analysis:

calc.: C, 55.51; H, 5.38; and N, 4.98. found: C, 55.37; H, 5.40; and N, 5.03.

Melting point: 153.5° C. (dec.)

SPIB00101: 2-O-Acetylsalicylic Acid (2S)-(+)-Serine Ester

A mixture of N-carbobenzyloxy-L-serine benzyl ester (Z-Ser-OBzl, 23.17 g, 70.34 mmole) and pyridine (30 mL) in anhydrous dichloromethane (500 mL) was cooled in an ice bath while under a nitrogen atmosphere. Acetylsalicyloyl chloride (21.07 g, 106.1 mmole) was added and the mixture was allowed to warm to room temperature and stir over two days. After 48 hours, the mixture was poured into ice-cold 2N hydrochloric acid (400 mL). After mixing, the layers were separated and the dichloromethane fraction was washed water (500 mL), saturated sodium bicarbonate solution (500 mL), water (500 mL), brine (500 mL) and dried over sodium sulfate (25 g). After filtration, concentration under reduced pressure, and drying under high vacuum, the remaining brown solid (47.19 g) was purified by flash chromatography on silica gel (200 g, 0.035-0.070 mm, 6 nm pore diameter), eluting with hexanes/ethyl acetate (3:1). After concentration of the product containing fractions under reduced pressure and drying under high vacuum until the weight was constant, the protected acetylsalicylic-L-serine ester SPIB0010101 (32.97 g, 95% yield) was produced as a white solid.

SPIB0010101

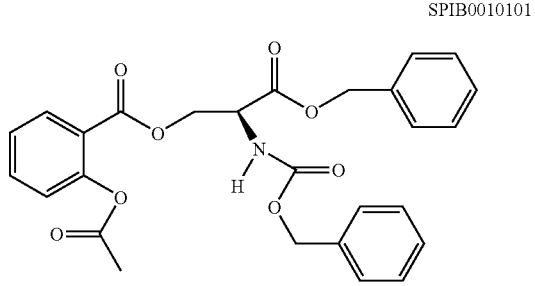

$^1$H NMR (300 MHz, CDCl$_3$): δ=7.74 (1H, d, J=7.8 Hz), 7.55 (1H, dt, J=7.8, 1.5 Hz), 7.33-7.21 (11H, m), 7.08 (1H, d, J=7.5 Hz), 5.68 (1H, d, J=8.4 Hz), 5.20 (2H, s), 5.12 (2H, s), 4.77 (1H, m), 4.66 (1H, dd, J=11.4, 3.3 Hz), 4.57 (1H, dd, J=11.4, 3.3 Hz), 2.30 (3H, s).

$^{13}$C NMR (75 MHz, CDCl$_3$): δ=169.45, 169.09, 163.68, 163.35, 155.57, 150.77, 135.87, 134.75, 134.07, 131.44, 128.50, 128.43, 128.27, 128.14, 128.04, 125.92, 123.71, 122.18, 67.83, 67.27, 64.63, 53.55, and 21.03.

The protected acetylsalicylic-L-serine ester SPIB0010101 (21.0 g, 42.7 mmole) was dissolved in ethanol (100 mL) and ethyl acetate (100 mL) at room temperature and added to a Parr bottle that contained 10% palladium on carbon (4.20 g, 50% wet) under a nitrogen atmosphere. The nitrogen atmosphere was replaced with hydrogen gas (20 psi). After 5 hours additional 10% palladium catalyst (4.26 g) was added and the hydrogen atmosphere was returned (20 psi). After an additional 20 hours of shaking at room temperature, the palladium catalyst was removed by filtration through celite. The remaining solids (palladium/celite and product) were washed with water (1500×2 mL) until the product was removed. The ethanol and water fractions were concentrated under reduced pressure at room temperature. The remaining solid (7.17 g) was dissolved in DIUF water (4.3 L), filtered through celite to remove insoluble material, and concentrated under high vacuum at room temperature. The white solid was then washed with 1,4-dioxane (100 mL) and DIUF water (50 mL) overnight. After 24 hours the solid was filtered and dried under high vacuum until the weight was constant (24 hours).

The experiment produced the acetylsalicylic-L-serine ester SPIB00101 (6.17 g, 54% yield) as a white solid.

SPIB00101

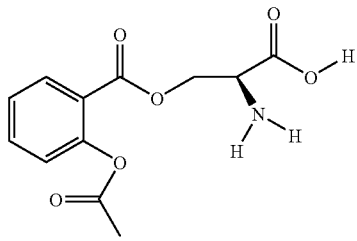

$^1$H NMR (300 MHz, D$_2$O-DCl): δ=8.05 (1H, dd, J=7.8, 1.5 Hz), 7.75 (1H, dt, J=7.8, 1.5 Hz), 7.47 (1H, dt, J=7.8, 0.9 Hz), 7.27 (1H, dd, J=7.8, 0.9 Hz), 4.87 (1H, dd, 12.6, 4.2 Hz), 4.79 (1H, dd, J=12.6, 3.0 Hz), 4.62 (1H, dd, 4.2, 3.0 Hz), 2.39 (3H, s).

$^{13}$C NMR (75 MHz, D$_2$O-DCl): δ=173.01, 168.58, 164.54, 149.72, 135.39, 131.59, 126.87, 123.62, 121.15, 62.38, 52.05, and 20.44.

HPLC analysis:

98.1% purity; r.t.=5.839 min.; 65% TFA (0.1%)/35% methanol; 1 mL/min; 35 C; Luna C18, 3u column (SN 184225-37), 4.6×250 mm; 22 ul injection; DAD1B, Sig=240, 4 Ref=550,100.

CHN analysis:

calc.: C, 53.93; H, 4.90; and N, 5.24. found: C, 54.02; H, 5.00; and N, 5.23.

Melting point: 147.0° C. (dec.)

SPIB00103: 2-O-Acetylsalicylic Acid (2S,4R)-4-Hydroxyproline Ester

A mixture of N-carbobenzyloxy-L-Hydroxyproline benzyl ester (Z-Ser-OBzl, 21.5 g, 60.5 mmole) and pyridine (25 mL) in anhydrous dichloromethane (500 mL) was cooled in an ice bath while under a nitrogen atmosphere. Acetylsalicyloyl chloride (13.2 g, 66.6 mmole) was added and the mixture was allowed to warm to room temperature and stir overnight. After 24 hours, additional acetylsalicyloyl chloride (5.0 g, 25.2 mmole) was added and the mixture was allowed to stir overnight. After 48 hours, the mixture was poured into ice-cold 1N hydrochloric acid (500 mL). After mixing, the layers were separated and the dichloromethane fraction was washed with water (500 mL), saturated sodium bicarbonate solution (500 mL), water (500 mL), brine (500 mL) and dried over sodium sulfate (25 g). After filtration, concentration under reduced pressure, and drying under high vacuum, the remaining yellow oil (40.7 g) was purified by flash chromatography on silica gel (460 g, 0.035-0.070 mm, 6 nm pore diameter), eluting with heptane/ethyl acetate (3:1). After concentration of the product containing fractions under reduced pressure and drying under high vacuum until the weight was constant, the protected acetylsalicylic-L-Hydroxyproline ester SPIB0010301 (21.31 g, 68% yield) was produced as a colorless oil.

SPIB0010301

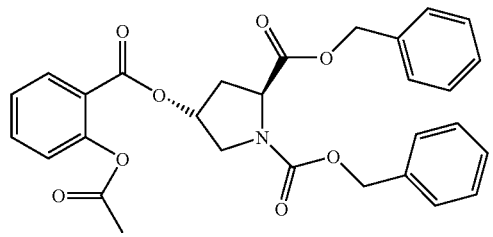

$^1$H NMR (300 MHz, CDCl$_3$): δ=7.92 (1H, d, J=7.8 Hz), 7.56 (1H, t, J=7.8 Hz), 7.34-7.21 (10H, m), 7.09 (1H, d, J=7.8 Hz), 5.48 (1H, s), 5.21 (2H, m), 5.03 (2H, d, J=15 Hz), 4.57 (1H, m), 3.85 (2H, m), 2.53 (1H, m), 2.28 (4H, m).

$^{13}$C NMR (75 MHz, CDCl$_3$): δ=171.72, 171.49, 169.25, 163.47, 163.30, 154.52, 153.93, 150.54, 136.05, 135.94, 135.21, 135.00, 134.17, 134.12, 128.43, 128.32, 128.28, 128.20, 128.05, 127.98, 127.94, 127.79, 125.89, 123.70, 122.46, 122.38, 73.24, 72.59, 67.33, 67.11, 66.97, 58.02, 57.69, 52.47, 52.15, 36.74, 35.65, 20.90.

The protected acetylsalicylic-L-Hydroxyproline ester SPIB0010301 (10.6 g, 20.5 mmole) was dissolved in ethanol (75 mL) and ethyl acetate (75 mL) at room temperature and added to a Parr bottle that contained 10% palladium on carbon (3.0 g, 50% wet) under a nitrogen atmosphere. The nitrogen atmosphere was replaced with hydrogen gas (20 psi). After 17 hours of shaking at room temperature, the reaction mixture was washed with water (500 mL) for two hours. The organic layer (top) was removed via pipette and the aqueous layer was filtered through celite. The water fraction was concentrated under reduced pressure at room temperature. The remaining solid (6.71 g) was then washed with anhydrous dichloromethane (35 mL) overnight. After 24 hours the solid was filtered and dried under high vacuum until the weight was constant (24 hours). The acetylsalicylic-L-Hydroxyproline ester, SPIB00301 (2.87 g, 47.7% yield) was produced as a white solid.

SPIB00103

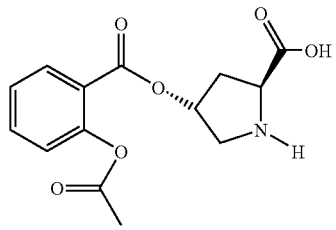

$^1$H NMR (300 MHz, D$_2$O-DCl): δ=8.09 (1H, d, J=7.5 Hz), 7.75 (1H, t, J=7.5 Hz), 7.48 (1H, t, J=7.5 Hz), 7.28 (1H, d, J=7.5 Hz), 5.69 (1H, m), 4.76 (1H, t, J=7.5 Hz), 3.86 (1H, dd, J=13.5, 3.9 Hz), 3.74 (1H, d, J=13.5 Hz), 2.81 (1H, dd, J=15.0, 7.5 Hz), 2.60 (1H, m), 2.40 (3H, s).

$^{13}$C NMR (75 MHz, D$_2$O-DCl): δ=173.13, 170.25, 164.31, 149.65, 135.36, 131.54, 126.87, 123.54, 121.37, 73.86, 58.34, 50.95, 34.38, and 20.48.

HPLC analysis:
98.3% purity; r.t.=7.201 min.; 65% TPA (0.1%)/35% methanol; 1 mL/min; 35 C; Luna C18, 3u column (SN 184225-37), 4.6×250 mm; 22 ul injection; DAD1B, Sig=240, 4 Ref=550,100.

CHN analysis:
calc.: C, 57.34; H, 5.16; and N, 4.78. found: C, 57.09; H, 5.23; and N, 4.91.

Melting point: 162° C. (dec.)

Specificity of L-Threonine to Separate Racemic and Stereoisomeric Mixtures:

When the racemic Ibuprofen, racemic Ketoprofen, racemic Ketorolac were reacted with L-Threonine, the resulting racemic drug-L-Threonine esters had quite varying physicochemical properties, and it was easy to crystallize or precipitate from the reaction mixture. One trained in the art of making amino acid esters of such drug would conclude that Hydroxy proline and Serine esters of these drugs will also result in separation of the reacemic mixtures in the form of corresponding esters. The inventor surprisingly found that only L-Threonine ester are readily separable and it is not the same with other amino acids. In case of both Hydroxyproline and Serine esters of Ketoprofen, the resulting Ketoprofen Hydroxyproline ester or serine ester were not as readily separable like L-Threonine ester of Ketoprofen. Only L-Threonine ester was able to separate the racemic mixture of Ketoprofen into the individual enantiomeric esters. The same surprising results were obtained for Ketorolac as well.

Efficacy (Anti Nociceptive Potential) of Synthesis of the L-Serine, L-Threonine, and L-Hydroxyproline Esters of (±)-Ibuprofen by Employing Acetylcholine Induced Abdominal Constriction Method in Male Albino Mice:

The present study was conducted to evaluate the efficacy of L-serine, L-Threonine, and L-hydroxyproline esters of (±)-Ibuprofen taking into account the antagonizing property on acetylcholine induced writhe as an index in albino mice.

Ibuprofen (racemic mixture) and ibuprofen (S)-(+) served as reference controls.

Different new formulations of ibuprofen and reference controls viz., ibuprofen (racemic mixture) and ibuprofen (S)-(+) were administered by gavage to male albino mice (Swiss strain), using 5% (v/v) Tween 80 in milli Q water as the vehicle. The study was conducted at two dose levels viz. 50 mg and 100 mg/kg body weight along with a vehicle control group. At each dose level 10 animals were used. All the doses were expressed as ibuprofen molar equivalents. The doses used as well as the molar equivalents are presented below.

TABLE 2

| Formulation: Molar Equivalent: | |
|---|---|
| Formulation | Molar equivalent |
| S-(+)-Ibuprofen-L-Threonine ester | 0.833 units are equivalent to 1 unit of Ibuprofen |
| (±)-Ibuprofen-L-serine ester | 1.6 units are equivalent to 1 unit of Ibuprofen |
| (±)-Ibuprofen-L-hydroxyproline ester | 1.55 units are equivalent to 1 unit of Ibuprofen |

TABLE 3

| Test Item: Group: Dose(mg/kg): Equivalent wt. Of the test item: | | | |
|---|---|---|---|
| Test Item | Group | Dose (mg per kg) [in terms of Ibuprofen] | Equivalent weight of the Test item [mg/kg] |
| Vehicle | Vehicle control Group | 0.0 | — |
| S-(+)-Ibuprofen-L-Threonine ester | Test Group 1 | 50.0 | 41.65 |
| | Test Group 2 | 100.0 | 83.30 |
| (±)-Ibuprofen-L-serine ester (Ibuprofen S) | Test Group 3 | 50.0 | 80.0 |
| | Test Group 4 | 100.0 | 160.0 |
| (±)-Ibuprofen-L-hydroxyproline ester | Test Group 5 | 50.0 | 77.5 |
| | Test Group 6 | 100.0 | 155.0 |
| Ibuprofen (racemic mixture) | Test Group 7 | 50.0 | 50.0 |
| | Test Group 8 | 100.0 | 100.0 |
| Ibuprofen S+ | Test Group 9 | 50.0 | 25.0 |
| | Test Group 10 | 100.0 | 50.0 |

The efficacy in terms of antagonizing effect on acetylcholine induced single writhe at two dose levels –50.0 and 100.0 mg/kg for the three formulations and reference controls are presented below.

TABLE 4

| Test Item: Group: Dose (mg/kg): Number of animals showing absence of single writhe (out of 10) | | | | |
|---|---|---|---|---|
| | | Dose (mg per kg) | Number of animals showing absence of single writhe (number of animals per dose = 10) | |
| Test Item | Group | [in terms of Ibuprofen] | One hour after dosing | Three hours after dosing |
| Vehicle | Vehicle control | 0.0 | 0 | 0 |
| S-(+)-Ibuprofen-L-Threonine ester | Low dose | 50.0 | 1 | 0 |
| | High dose | 100.0 | 3 | 0 |

TABLE 4-continued

Test Item: Group: Dose (mg/kg): Number of animals showing absence of single writhe (out of 10)

| Test Item | Group | Dose (mg per kg) [in terms of Ibuprofen] | Number of animals showing absence of single writhe (number of animals per dose = 10) | |
|---|---|---|---|---|
| | | | One hour after dosing | Three hours after dosing |
| (±)-Ibuprofen-L-serine ester | Low dose | 50.0 | 4 | 2 |
| | High dose | 100.0 | 6 | 4 |
| (±)-Ibuprofen-L-hydroxyproline ester | Low dose | 50.0 | 5 | 4 |
| | High dose | 100.0 | 7 | 7 |
| Ibuprofen (racemic mixture) | Low dose | 50.0 | 4 | 2 |
| | High dose | 100.0 | 6 | 6 |
| Ibuprofen S+ | Low dose | 50.0 | 5 | 1 |
| | High dose | 100.0 | 6 | 6 |

Statistical analysis employing Chi—square test procedure did not show any statistically significant difference among the formulations in comparison to reference control, while comparing the number of animals not showing writhe in each groups, as the respective "p" was found to be greater than 0.05, the level of significance. Also note that the dose of S(+)Ibuprofen-L-Threonine ester is only ½ the normal dose of Ibuprofen.

From clinical observation based on the number of animals not showing writhes due to administration of acetylcholine, (±)-Ibuprofen-L-hydroxyproline ester was found to be more effective in antagonizing the acetylcholine induced writhe when compared to other formulations and Ibuprofen (racemic) and Ibuprofen (S)-(+).

TABLE 5

Summary of Efficacy of L-serine, L-Threonine, and L-hydroxyproline esters of (±)-Ibuprofen, Ibuprofen (racemic mixture) and Ibuprofen (S)-(+) - Based on Antagonizing Property of Acetylcholine Induced Writhe in Albino Mice

| Dose (mg/kg) [in terms of Ibuprofen] | Test Item | Number of animals showing absence of single writhe (number of animals per dose = 10) | |
|---|---|---|---|
| | | One hour after dosing | Three hours after dosing |
| 50 mg/kg | Vehicle control | 0 | 0 |
| | S-(+)-Ibuprofen-L-Threonine ester | 1 | 0 |
| | (±)-Ibuprofen-L-serine ester | 4 | 2 |
| | (±)-Ibuprofen-L-hydroxyproline ester | 5 | 4 |
| | Ibuprofen (racemic mixture) | 4 | 2 |
| | Ibuprofen (S)-(+) | 5 | 1 |

TABLE 6

| 100 mg/kg | Vehicle control | 0 | 0 |
|---|---|---|---|
| | S-(+)-Ibuprofen-L-Threonine ester | 3 | 0 |
| | (±)-Ibuprofen-L-serine ester | 6 | 4 |
| | (±)-Ibuprofen-L-hydroxyproline ester | 7 | 7 |
| | Ibuprofen (racemic mixture) | 6 | 6 |
| | Ibuprofen (S)-(+) | 6 | 6 |

The data were subjected to statistical analysis employing Chi—square test procedure for evaluating the efficacy of the new formulations in comparison to the reference controls. The test did not show any statistically significant difference among the formulations in comparison to reference control, while comparing the number of animals not showing writhe in each groups, as the respective "p" was found to be greater than 0.05, the level of significance.

Figure 2:
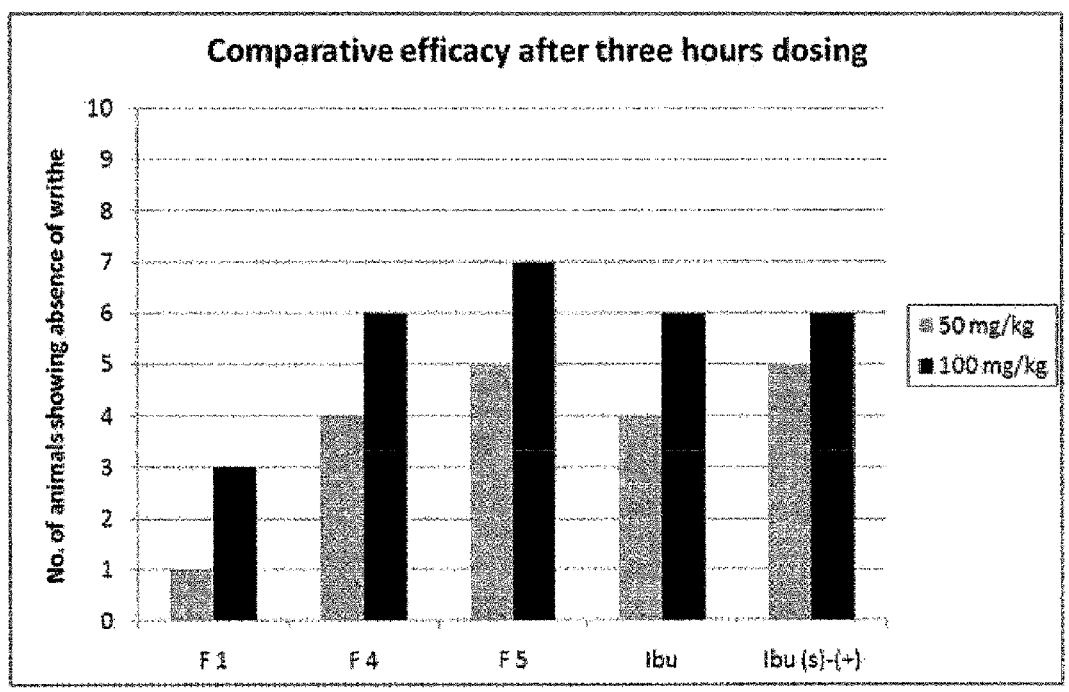
FIG. 2 graphically compares the efficacy of L-serine ester of (±) Ibuprofen, (F1), L-Threonine ester of, (I) Ibuprofen (F2), L-hydroxyproline ester of (±) Ibuprofen (F3), ± Ibuprofen and S(+) Ibuprofen after 3 hour dosing, based on the antagonizing property of Acetylcholine induced writhes in albino mice.
Figure 3:
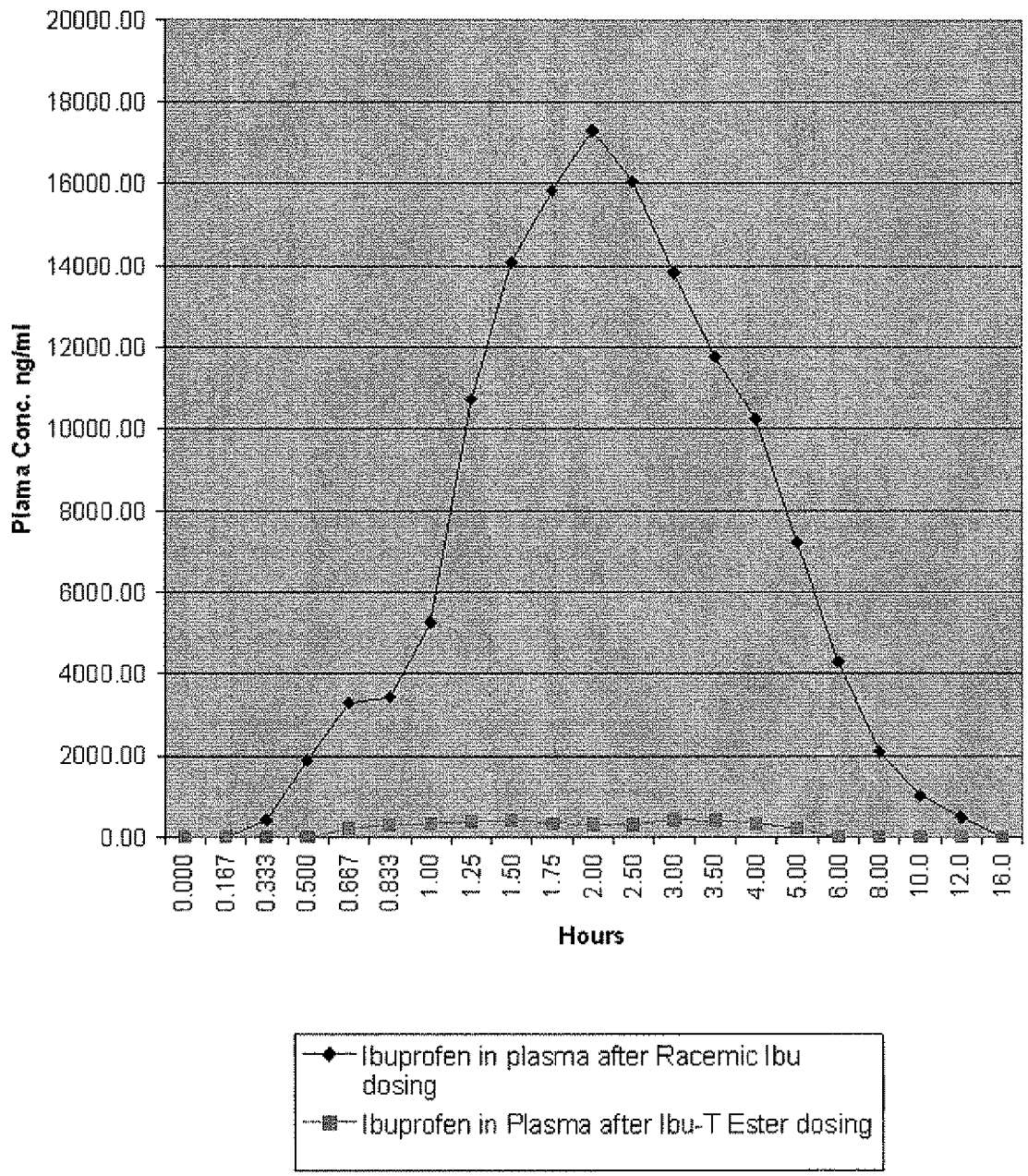
FIGS. 3-8 compares graphically the plasma concentration in humans after administration of ibuprofen and ibuprofen Threonine ester.
Figure 4:
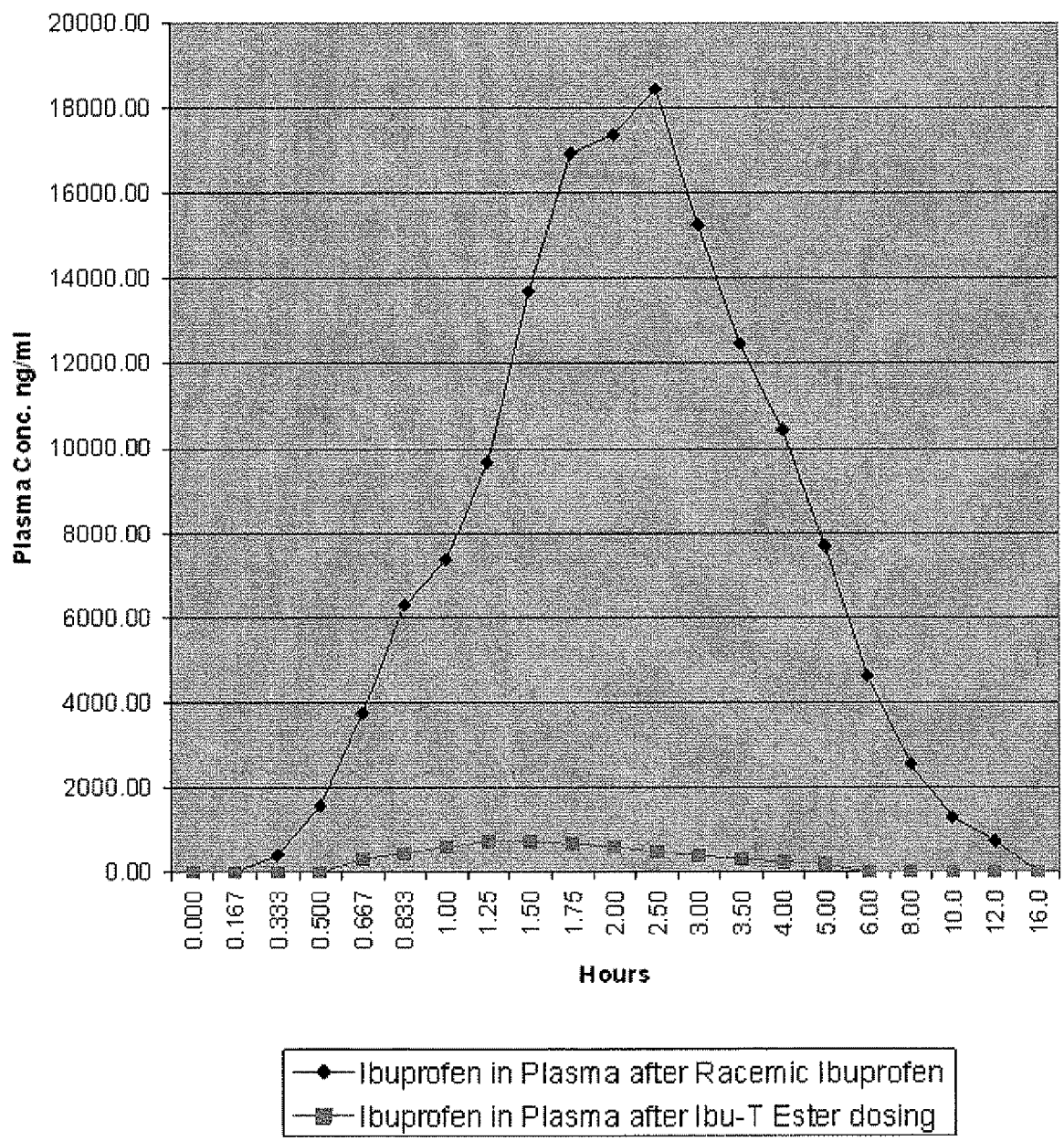
Figure 5:
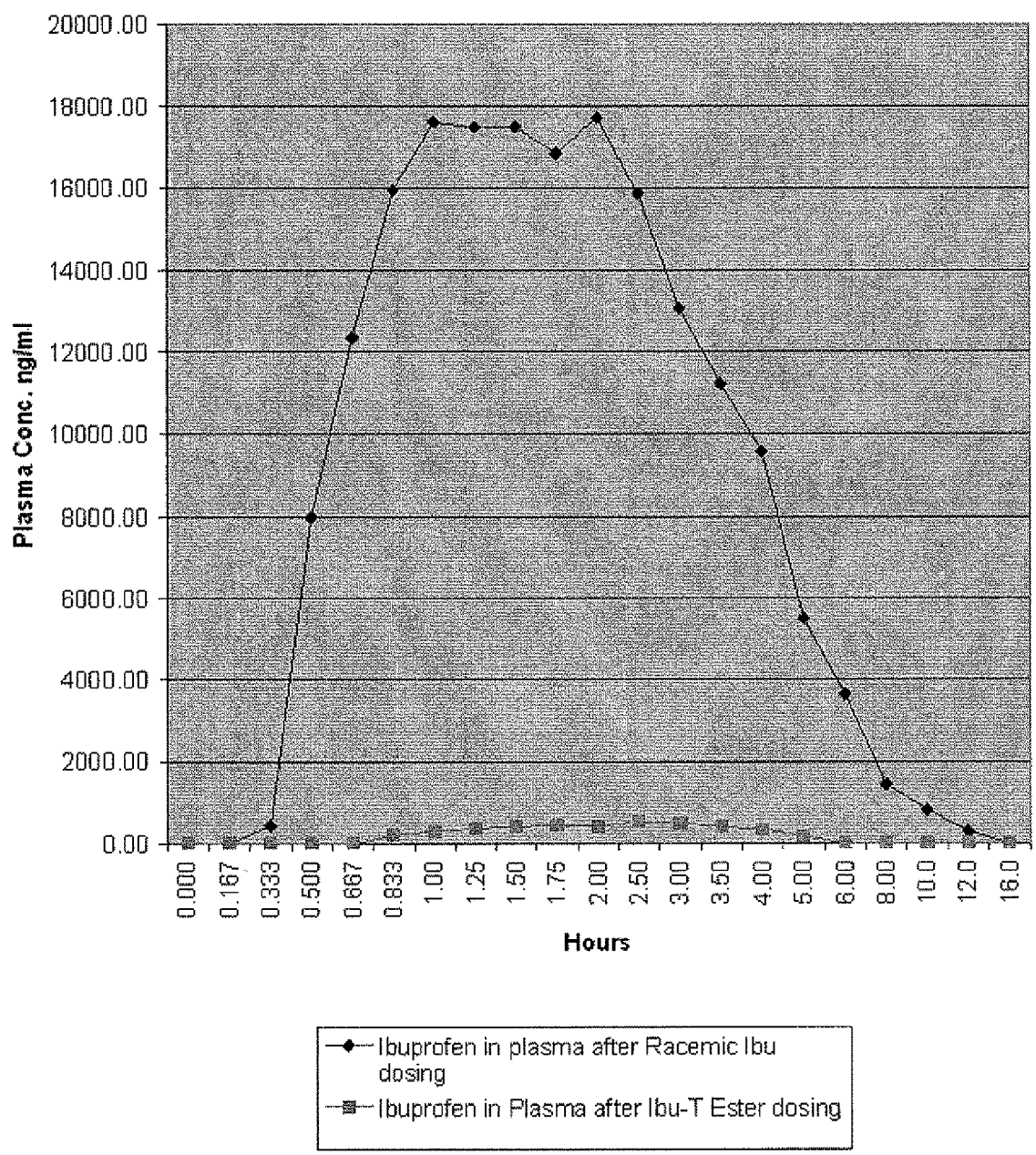
Figure 6:
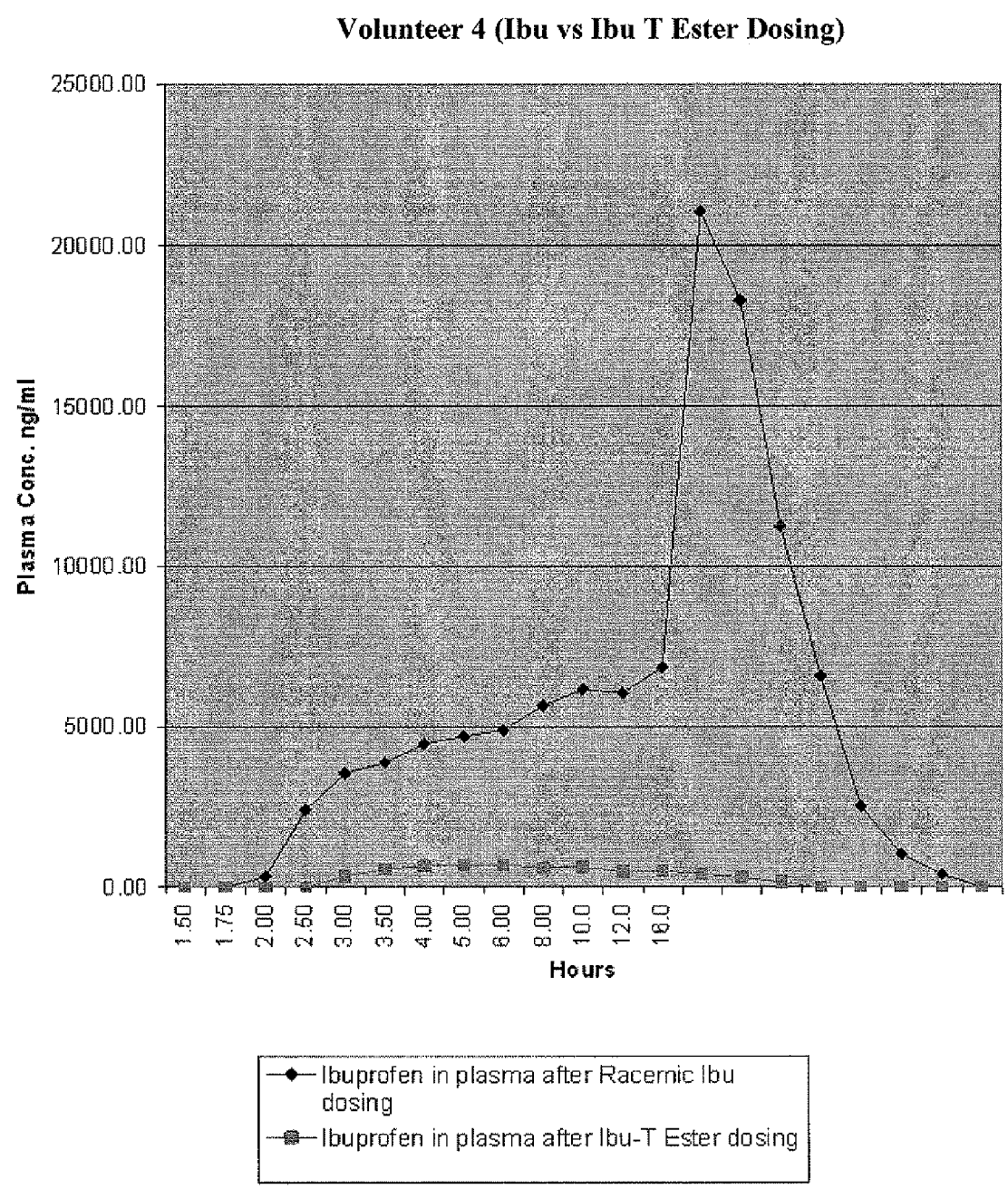
Figure 7:
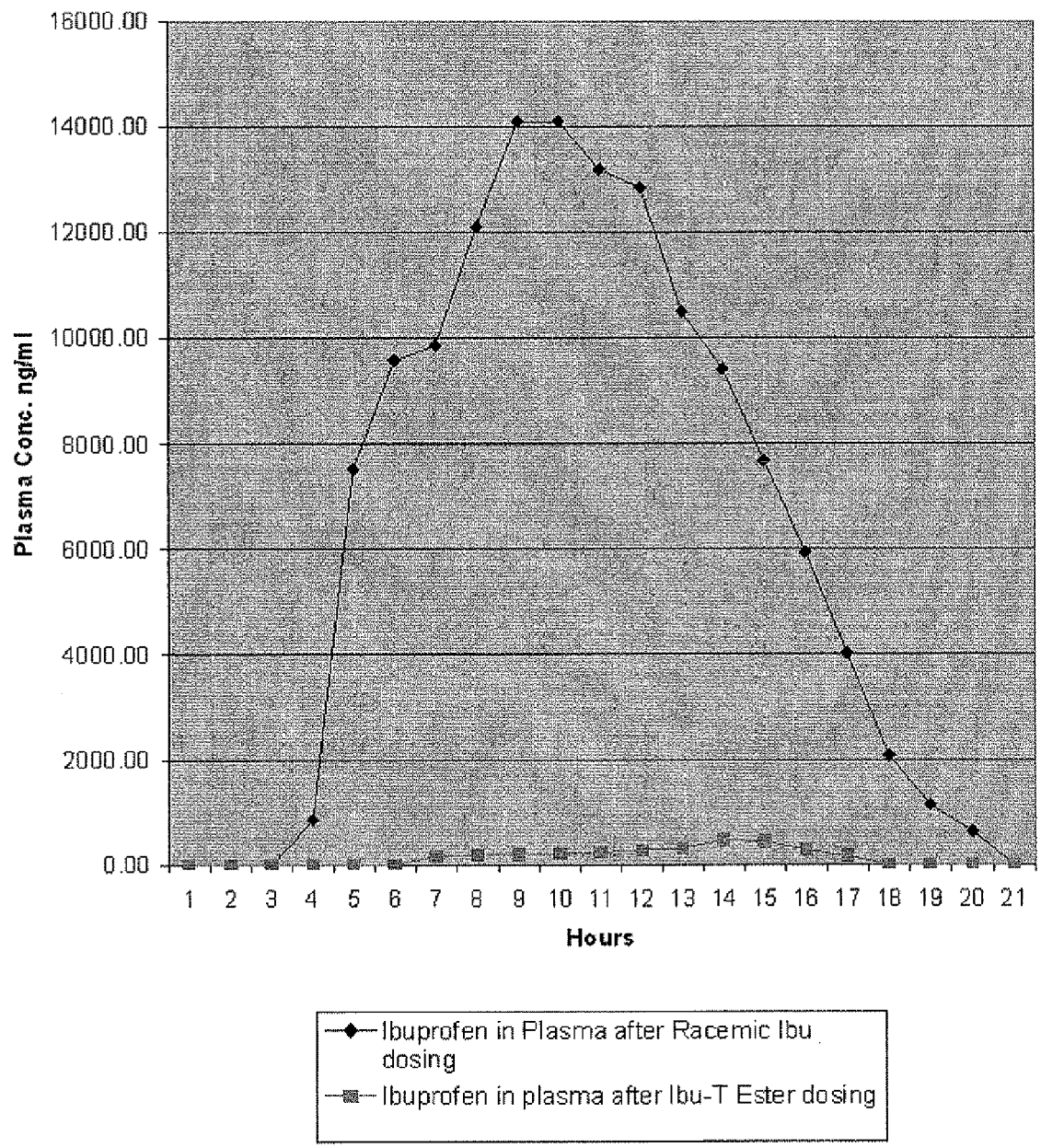
Figure 8:
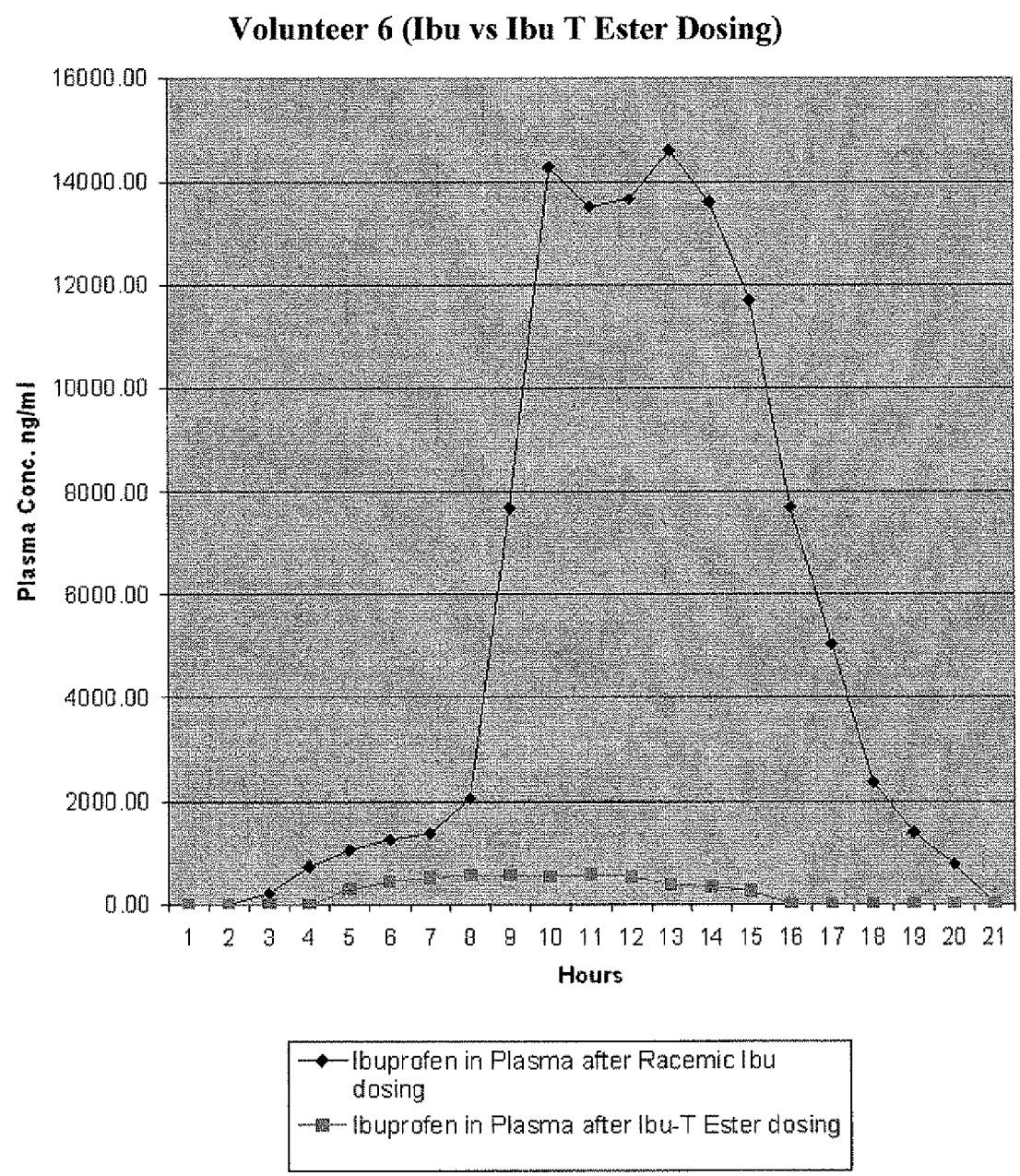

The data is also summarized in FIGS. 1 and 2. From clinical observations and bar diagram for comparative efficacy (FIGS. 1 and 2) based on the number of animals not showing writhes due to administration of acetylcholine, (±)-Ibuprofen-L-hydroxyproline ester was found to be more effective in antagonizing the acetylcholine induced writhe when compared to other formulations and Ibuprofen (racemic) and Ibuprofen (S)-(+). However, as shown hereinbelow, the hydroxyproline ester was found to be more toxic than the threonine ester, as shown in the 28 day chronic toxicity study described hereinbelow. Thus, the therapeutic index for the L-Threonine ester is significantly more favorable than with the other esters of hydroxy containing amino acids.

CONCLUSION

The present study was conducted to evaluate the relative efficacy of new formulations of ibuprofen. For this the antagonizing property of new formulations on acetylcholine writhes was taken as an index to determine the relative efficacy of the formulations. Ibuprofen (racemic mixture and ibuprofen (S)-(+) served as reference controls. The study was conducted at two dose levels (50.0 and 100.0 mg/kg) along with a vehicle control group.

Gastric mucosal irritation potential of L-serine, L-Threonine, and L-hydroxyproline esters of (±)-Ibuprofen in fasted male albino rats

SUMMARY

The present study was conducted to determine the relative potential of new formulations of ibuprofen (L-serine, L-Threonine, and L-hydroxyproline esters of (±)-Ibuprofen) to cause gastric mucosal irritation/lesions in fasted male albino rats. Ibuprofen (racemic mixture) and Ibuprofen(S)-(+) served as reference controls.

Different new formulations of ibuprofen and ibuprofen (racemic mixture) and ibuprofen(S)-(+) were administered by gavage to fasted male albino rats (Wistar strain), using 5% solution of Tween 80 in milli Q water as the vehicle. The study was conducted at two dose levels viz. 200 mg and 300 mg/kg body weight along with a vehicle control group. At each dose level 5 animals were used. All the doses were expressed as ibuprofen (racemic mixture) molar equivalents. The doses used as well as the molar equivalents were presented below.

TABLE 7

Formulation: Molar Equivalent

| Formulation | Molar equivalent |
| --- | --- |
| S-(+)-Ibuprofen-L-Threonine ester | 0.833 units are equivalent to 1 unit of Ibuprofen |
| (±)-Ibuprofen-L-serine ester | 1.60 units are equivalent to 1 unit of Ibuprofen |
| (±)-Ibuprofen-L-hydroxyproline ester | 1.55 units are equivalent to 1 unit of Ibuprofen |

The various groups used are tabulated hereinbelow:

TABLE 8

Test item: group: Dose (mg/kg) Equivalent wt.

| Test item | Group | Dose (mg per kg) [in terms of Ibuprofen] | Equivalent weight of the Test item [mg/kg] |
| --- | --- | --- | --- |
| Vehicle | Vehicle control Group | 0.0 | — |
| S-(+)-Ibuprofen-L-Threonine ester | Test Group 1 | 200.0 | 0.0 |
| | Test Group 2 | 300.0 | 166.6 |
| (±)-Ibuprofen-L-serine ester | Test Group 1 | 200.0 | 249.9 |
| | Test Group 2 | 300.0 | 320.0 |
| (±)-Ibuprofen-L-hydroxyproline ester | Test Group 1 | 200.0 | 480.0 |
| | Test Group 2 | 300.0 | 310.0 |
| Ibuprofen (racemic mixture) | Test Group 1 | 200.0 | 465.0 |
| | Test Group 2 | 300.0 | 300.0 |
| Ibuprofen (S)-(+) | Test Group 1 | 200.0 | 100.0 |
| | Test Group 2 | 300.0 | 150.0 |

The rats were fasted for a period of 18 to 22 hours before dosing. The test item was administered as a single dose by gavage. Three hours after drug administration, the animals were killed humanely by $CO_2$ gas inhalation. The stomach was dissected out and observed for the quantity of mucous exudate, degree of hyperemia and thickening of stomach wall, hemorrhagic spots (focal or diffuse), nature of hemorrhages (petechial or ecchymotic) along with the size and perforations or any other lesions The observations on gastric mucosal irritation of animals of various groups were summarized as follows: None of the animals in the Vehicle control group, S(+)Ibuprofen-L-Threonine Ester (200 and 300 mg/kg), (±)Ibuprofen-L-Serine (200 and 300 mg/kg), (±)Ibuprofen-L-Hydroxyproline (200 and 300 mg/k) groups showed any evidence of gastric mucosal irritation. In the (±)Ibuprofen 200 mg/kg dose, 1 out of 5 animals showed evidence of gastric mucosal irritation. In the case of (±)Ibuprofen 300 mg/kg dose, 3 out of 5 animals showed severe gastric mucosal irritation. Surprisingly, in the S(+)Ibuprofen group at 200 mg/kg dose, all five animals dosed showed evidence of gastric mucosal irritation, and 3 out of 5 animals showed severe gastric mucosal irritation in the S(+)Ibuprofen group. Please note that the last group is pure enantiomer, S(+) variety.

The results of the present study showed that none of the formulations of ibuprofen had caused any evidence of irritation of gastric mucosa in fasted male albino rats of male sex at the two dose levels tested (200 mg and 300 mg/kg body weight). In contrast both ibuprofen (racemic mixture) and ibuprofen S(+) had caused irritation of gastric mucosa at the two dose levels tested. Further ibuprofen S(+) was found to be more gastric mucosal irritant than ibuprofen racemic mixture.

28-Day Chronic Toxicity Studies with S(+) Ibuprofen L-Threonine Ester in Rats

Chronic toxicity of S(+) Ibuprofen-L-Threonine ester was compared against a vehicle, (+/−)racemic Ibuprofen and (+/−) racemic Ibuprofen-L-Hydroproline ester. Test species used was Swiss Albino Mice, both male and female with body weight range of 18-27 gms. Randomization was done by the method of stratified randomization procedure using SAS software program (Version 8.2) with stratification by bodyweight. The various groups are depicted below:

TABLE 9

| GROUP | TEST ITEM | NUMBER OF ANIMALS | ANIMAL NUMBERS Female | ANIMAL NUMBERS Male |
| --- | --- | --- | --- | --- |
| Vehicle Control | Vehicle | 10 | 01 to 05 | 06 to 10 |
| Test Group 1 | L-Threonine ester of S(+) Ibuprofen | 10 | 11 to 15 | 16 to 20 |
| Test Group 2 | L-Hydroxyproline ester of S(+) Ibuprofen | 10 | 21 to 25 | 26 to 30 |
| Reference Test Group | Ibuprofen USP | 10 | 31 to 35 | 36 to 40 |

The test doses are expressed as Ibuprofen molar equivalents

TABLE 9A

| Test Item | Group | Dose (mg per kg) [in terms of Ibuprofen] | Equivalent weight of the Test item [mg] |
| --- | --- | --- | --- |
| Vehicle | Vehicle Control | 0.0 | 0.0 |
| L-Threonine ester of S(+) Ibuprofen | Test Group 1 | 200.0 | 334.0 |
| L-Hydroxyproline ester of Racemic Ibuprofen | Test Group 2 | 200.0 | 310.0 |
| Ibuprofen USP (Racemic mixture) | Reference Control | 200.0 | 200.0 |

The duration of dosing was 28 days. All the animals were daily till the end of the study for the presence/absence of clinical symptoms of toxicity. Cage side observations included changes in the skin, eyes, posture, gait, respiration and behavior pattern. The incidence of twitching, tremors, convulsions, salivation, diarrhea and death if any, were also recorded.

Animals exposed to different doses of the test substance did not indicate any symptoms of toxicity (Table 10).

TABLE 10

Summary of Clinical Symptoms of Toxicity in Albino Mice

| GROUP (mg/kg body weight) | Symptoms of toxicity | Sex | Animal Numbers | Period of Signs in days From-to | Mortality |
|---|---|---|---|---|---|
| Vehicle Control (0.0) (No Treatment) | No symptoms of toxicity were observed | Female | 01 to 05 | 0-28 | Nil |
| | No symptoms of toxicity were observed | Male | 6 to 10 | 0-28 | Nil |
| Test Group 1 (Ibuprofen S + T) (334.0 mg/kg) | No symptoms of toxicity were observed | Female | 11 to 15 | 0-28 | Nil |
| | No symptoms of toxicity were observed | Male | 16 to 20 | 0-28 | Nil |
| Test Group 2 (Ibuprofen HP) (310.0 mg/kg) | No symptoms of toxicity were observed | Female | 21 to 25 | 0-28 | 1/5 |
| | No symptoms of toxicity were observed | Male | 26 to 30 | 0-28 | Nil |
| Reference Control 3 (Ibuprofen USP) (200.0 mg/kg) | No symptoms of toxicity were observed | Female | 31 to 35 | 0-28 | 3/5 |
| | No symptoms of toxicity were observed | Male | 36 to 40 | 0-28 | 1/5 |

In the above table, Ibuprofen S+T refers to S(+)Ibuprofen-L-Threonine Ester and Ibuprofen. HP refers to Ibuprofen hydroxy Praline Ester.

Death Record

Ibuprofen HP

Animal no. 23 (female animal) died on 21 day of dosing.

Positive Control Group

Animal no. 31 (female animal) died on 23 day of dosing.

Animal no. 32 (female animal) died on 21 day of dosing.

Animal no. 33 (female animal) died on 24 day of dosing.

Animal no. 40 (male animal) died on 10 day of dosing.

While there were no cage side specific toxicity noted, surprisingly 40% of the animals receiving racemic ibuprofen died, only 10% of the rats receiving Hydroxyproline ester of Ibuprofen did not complete the full course, and even more surprisingly, none of the animals in the S(+)Ibuprofen-L-Threonine ester group died. The average increase/decrease is body weight, and percentage change of body weight of the surviving animals in various groups are shown below:

TABLE 11

| Treatment | Average Change In body Weight (gms) | Percentage Change (No of animals survived) |
|---|---|---|
| Vehicle | 4.65 | 19.97 (10) |
| S(+)Ibuprofen Threonine Ester | −0.68 | −3.61 (10) |
| Ibuprofen Hydroxy-Proline Ester | 1.43 | 5.75 (9) |
| Racemic Ibuprofen | 2.97 | 12.54 (6) |

While there was increase in body weight in treatments with racemic Ibuprofen and Ibuprofen Hydroxyproline ester, both group have mortalities, with currently marketed Ibuprofen showing more mortality than Hydroxyproline ester. Hence all the amino acid esters are far superior to Ibuprofen racemic mixture or the active S(+)Ibuprofen. However, the best product so far seems to be S(+)Ibuprofen-L-Threonine Ester, making it one of the ideal candidates to be advanced to human trials.

Human Clinical Trials with S(+)Ibuprofen-L-Threonine Ester:

Determination of the analgesic and anti-inflammatory effects of S(+)Ibuprofen-L-Threonine Ester in three human volunteers:

Two male, age 49 and 50 having severe headache took 1 capsule containing S(+)Ibuprofen-L-Threonine Ester. The capsule contents were equivalent to 200 mg of racemic Ibuprofen. Relief from headache was reported after 15 min, and complete absence of any pain from headache was reported at the end of 1 hour, which lasted for another 12 hours.

Two males age 49 and 51 took 1 capsule each containing S(+)Ibuprofen-L-Threonine ester for arthritic knee pain, which was perceptible. After 12 hours, both volunteers reported significant reduction in the pain associated with their right knee. Such amolearation of pain was further sustained for another 24 hours.

Pharmacokinetics of Ibuprofen in Human Volunteers:

Based upon preliminary analgesic and anti-inflammatory response from the 4 volunteers, Ibuprofen racemic drug was compared against S(+)Ibuprofen-L-Threonine ester at 200 mg equivalent dose. The plasma-concentration time profile in 6 volunteers, where S(+)Ibuprofen-L-Threonine ester concentrations were plotted against racemic ibupronfe concentrations in plasma for each volunteers.

Based upon the results of comparative bioavailability of racemic Ibuprofen versus Ibuprofen released from S(+)Ibuprofen-L-Threonine ester it is clear that only very small amount of Ibuprofen is released intact into human blood stream. This is due to the fact that S(+)Ibuprofen-L-threonine ester does not act as a prodrug of Ibuprofen, instead the Threonine ester had intact activity.

FIG. 3-8 are plots of plasma concentration of Ibuprofen in human volunteers after administration of 200 mg (or equivalent) of racemic Ibuprofen to human volunteers. The overall bioavailability of Ibuprofen from Ibuprofen Racemic mixture of 200 mg and equivalent dose of S(+)Ibuprofen-L-Threonine ester are shown in the table below:

TABLE 12

| Volunteer | AUC1 | AUC2 | % Availability |
|---|---|---|---|
| 1 | 69197.618 | 893.226 | 1.3 |
| 2 | 41861.277 | 1978.925 | 4.7 |
| 3 | 73121.747 | 940.133 | 1.3 |
| 4 | 38993.502 | 2101.642 | 5.4 |
| 5 | 34567.246 | 1657.496 | 4.8 |
| 6 | 66710.152 | 925.000 | 1.4 |

In the above table, AUC1 represents the cumulative area under the plasma concentration time curve following oral administration of 200 mg of racemic ibuprofen to human volunteers, and AUC2 represents the cumulative area under the plasma concentration time curve following oral administration of 200 mg ibuprofen equivalence of S(+)Ibuprofen-L-Threonine ester. The third column in the above table shows relative bioavailability of Ibuprofen in human plasma after oral administration of S(+)Ibuprofen-L-Threonine ester at equivalent doses. This clearly demonstrates that any activity seen in human volunteers is not due to release of any significant amounts of S(+)Ibuprofen into the plasma after oral ingestion of the Threonine ester.

The reason that S(+)Ibuprofen advanced to human pharmacokinetic studies was due to a lack of toxicity in 28-day chronic administration in rats compared to Ibuprofen, or Hydroxyproline ester of Ibuprofen. Furthermore, earlier studies indicated that S(+)Ibuprofen is highly toxic to gastric mucosa of rats. Similar results were also shown in various studies elsewhere, for example, other investigators compared S(+) and R(−) enantiomers of ibuprofen in male Wistar rats. At 40 mg/kg dose, microscopic evaluation of the GI tissue samples revealed significance difference in GI toxicity caused by S(+) than R(−) Ibuprofen (See Janjikhel, R K, Bricker, J D, Borochovitz, D, Adeyeye, C M, Stereoselective Disposition of Sustained Release Microspheres of Ibuprofen Enantiomers in Rats: II, Acute Gastrointestinal Toxicity. Drug Delivery, Vol 6, No. 3, August 1999, pp 163-170). However S(+)Ibuprofen-L-Threonine ester was GI sparing, and had no toxicity.

Furthermore, it has been reported that R(−)Ibuprofen may be capable of inhibiting both therapeutic and toxic effects of S(+)Ibuprofen (See Kaehler, S T, Phleps, W, Hesse, E. Dexibuprofen: Pharmacology, therapeutic uses and safety. Infammopharmacology, Vol 11 No. 4-6, 2003, pp 371-383). This is also consistent with observation, since in acute GI toxicity studies racemic ibuprofen was somewhat less toxic than S(+) Ibuprofen.

Similarly, Rainsford K D, in Pharmacology and Toxicology of Ibuprofen, in Rainsford, K D, ed. Ibuprofen, A critical bibliographic Review. London, Taylor and Francis, 2000, states that competition between the enantiomers of ibuprofen for prostaglandin production in vitro was evident, and that inhibition of binding of S(+) ibuprofen by R(−) ibuprofen in the racemic mixture contributed to the GI tolerance of the racemate.

However, what is not known in the art is that an ester of S(+)Ibuprofen would also be nontoxic. For example, one trained in the art of such derivative pharmacology, would have concluded that as S(+)Ibuprofen is highly toxic to the GI mucosa, and since S(+)Ibuprofen will be released from S(+) Ibuprofen-L-Threonine ester by the esterase enzymes in GI tract, and by the action of pancreatin enzyme in the duodenum, one trained in the art would have predicted that there will not be any reduction in toxicity. However, the current inventor surprisingly noted that S(+)Ibuprofen-L-Threonine ester is significantly and completely non-toxic to GI mucosa in the rats tested.

In spite of no ibuprofen appearing in the human plasma after oral administration of S(+)Ibuprofen-L-Threonine ester, significant analgesic and anti-inflammatory response was seen in the 2 volunteers each tested twice. Thus, S(+)Ibuprofen-L-threonine ester does not act as a prodrug, and it seems to have intact pharmacological activity.

While less effectiveness was seen in rat model with S(+) Ibuprofen-L-Threonine ester, the overriding factor that demonstrate that this drug is more suitable for human treatment of various diseases such as arthritis etc., is due to the fact that on chronic toxicity trials none of the animal died in this drug group. Furthermore, the S(+)Ibuprofen-L-Threonine ester exhibited no toxicity in either the gastric system or in the whole animal (as determined by number of surviving rats), thereby indicating that there is no toxicity potential in systemic circulation of human subjects with respect to this threonine derivative. Thus, S(+)Ibuprofen-L-Threonine ester exhibits enhanced pharmacological action, such as observed analgesic, anti-inflammatory and likely anti-pyretic properties elicited in humans.

Human Clinical Trial:

S(−)Ketorolac-L-Threonine ester capsules were filled using dextrose as the filler. The Ketorolac-L-Threonine ester dose was comparable to racemic Ketorolac Tromethamine tablets. For example, 13 mg of S(−)Ketorolac-L-Threonine ester was roughly equivalent to 13 mg of racemic Ketorolac tromethamine in tablet and/or capsule form.

A Female patient (age 72) suffering from severe ankolysing spodolytis, arthritis and other inflammatory joint problems was under treatment with Indomethacin, 25 mg twice daily dose. In order the evaluate the analgesic activity of S(−) Ketorolac-L-Threonine ester, the patient was withdrawn from treatment of Indomethacin. After 24 hours, the pain was returning and she was administered with 13 mg of S(−) Ketorolac L-Threonine ester, once in the morning and once in the evening. This was repeated for 5 days. During the entire period, the patient demonstrated lack of pain, no gastric irritation symptoms, or other side effects.

About 3 months later, the same above female volunteer repeated the experiment. In this time, she went off the indomethacin, and was administered only one dose of 13 mg of S(−) Ketorolac-L-Threonine ester. After the $2^{nd}$ day, she complained of the pain resurfacing, and the dose was then increased on the morning of the $3^{rd}$ day to twice daily 13 mg each. Beginning the $3^{rd}$ day she informed the doctor of lack of any pain, and this treatment was continued for another 3 days at two capsules of 13 mg each. On the $6^{th}$ day, morning she was then switched back to Indomethacin. This study showed that in this particular volunteer, 13 mg twice daily was the appropriate dose to alleviate her severe pain.

There are a number of screening tests to determine the utility of the derivatives created according to the disclosed methods. These include both in vitro and in vivo screening methods.

Surprisingly better results with L-Threonine esters of various drugs, racemic or otherwise were obtained. For examples, as described hereinabove, it was shown that the L-Threonine ester of Ibuprofen and Ketorolac possessed good clinical activity, and were less toxic in the animal models (Ibuprofen). Similar results were also obtained with respect to studies done with L-Threonine esters of various other drugs which were not racemic mixtures. Examples worth noting are Aspirin and Fenofibric Acid.

Synthesis of the various amino acid esters of Aspirin and Fenofibric acid are described in U.S. Ser. No. 11/343,557 and WO 2005/046575, the contents of both which are incorporated by reference in their entirety herein.

Gastric Mucosa Irritation Potential of the L-Serine, L-Threonine, and L-Hydroxyproline Esters of Acetylsalicylic Acid Compared to Acetylsalicylic Acid: —

A study was conducted to determine the relative potential of various derivatives of aspirin (L-serine, L-Threonine, and L-Hydroxyproline esters of acetylsalicylic acid) to cause gastric mucosal irritation/lesions in fasted male albino rats. Aspirin served as reference control.

The amino acid esters of aspirin and aspirin were administered by gavage to fasted male albino rats (Wistar strain), using 0.5% (w/v) Carboxymethylcellulose (CMC) in Phosphate Buffer (pH 2.6) solution as the vehicle. The study was conducted at two dose levels viz. 100 mg and 200 mg/kg body weight along with a vehicle control group. At each dose level 5 animals were used.

The rats were fasted for a period of 18 to 22 hours before dosing. The test item was administered as a single dose by gavage. Three hours after drug administration, the animals were killed humanely by $CO_2$ gas inhalation. The stomach was dissected out and observed for the quantity of mucous exudate, degree of hyperemia and thickening of stomach wall, hemorrhagic spots (focal or diffuse), nature of hemorrhages (petechial or ecchymotic) along with the size and perforations It was observed that none of the L-serine, L-Threonine, and L-Hydroxyproline esters of acetylsalicylic acid induced any evidence of irritation of gastric mucosa at the two doses tested viz., 0.100 and 200 mg/kg body weight. In contrast, aspirin (acetylsalicylic acid) caused irritation of the gastric mucosal in all the fasted male albino rats at the dose level of 200 mg/kg.

However at the dose level of 100 mg/kg aspirin failed to cause any evidence of gastric mucosal irritation in the male rats. Further none of the animals of different test groups showed any clinical symptoms of toxicity throughout the observation period of three hours.

However, the Threonine ester is less toxic than the other esters of the other hydroxy containing amino acids, and thus has a more effective relative therapeutic index.

Preliminary Blood Clotting Time Efficacy Trials in Rodents:

Since Aspirin is associated with a number of toxicities, primarily GI irritation, bleeding, ulcer and hemorrhage, several amino acid derivatives of Aspirin were prepared.

Drug Derivatives Synthesized: a) Aspirin-L-Serine Ester; b) Aspirin-L-Threonine Ester; c) Aspirin-L-Hydroxyproline Ester.

Doses Used: 1, 4, 10 and 20 mg/kg (Aspirin Equivalence)

Observations of Blood Clotting Time:

The data on the mean clotting time (MCT) of the animals of low, intermediate and high dose groups of different formulations, vehicle control and positive control groups estimated one hour after dosing were presented below (Table 13 and FIGS. 9 to 14):

TABLE 13

Summary of Mean Clotting Time (±S.D.) in Minutes-L-serine, L-Threonine, and L-Hydroxyproline esters of acetylsalicylic acid and Aspirin (Positive control)

|  | 1 mg/kg | 4 mg/kg | 10 mg/kg |
|---|---|---|---|
| Vehicle control |  | 4.9 ± 1.10 |  |
| L-Serine ester of acetylsalicylic acid | 5.7 ± 1.34 | 6.8 ± 1.48 | 6.9 ± 1.37 |
| L-Hydroxyproline ester of acetylsalicylic acid | 6.1 ± 1.10 | 5.7 ± 0.82 | 7.5 ± 1.18 |
| L-Threonine, ester of acetylsalicylic acid | 5.2 ± 1.14 | 5.6 ± 0.84 | 7.4 ± 0.97 |
| Positive control (acetylsalicylic acid) | 6.2 ± 1.40 | 8.1 ± 1.97 | 9.8 ± 1.32 |

Figure 9:
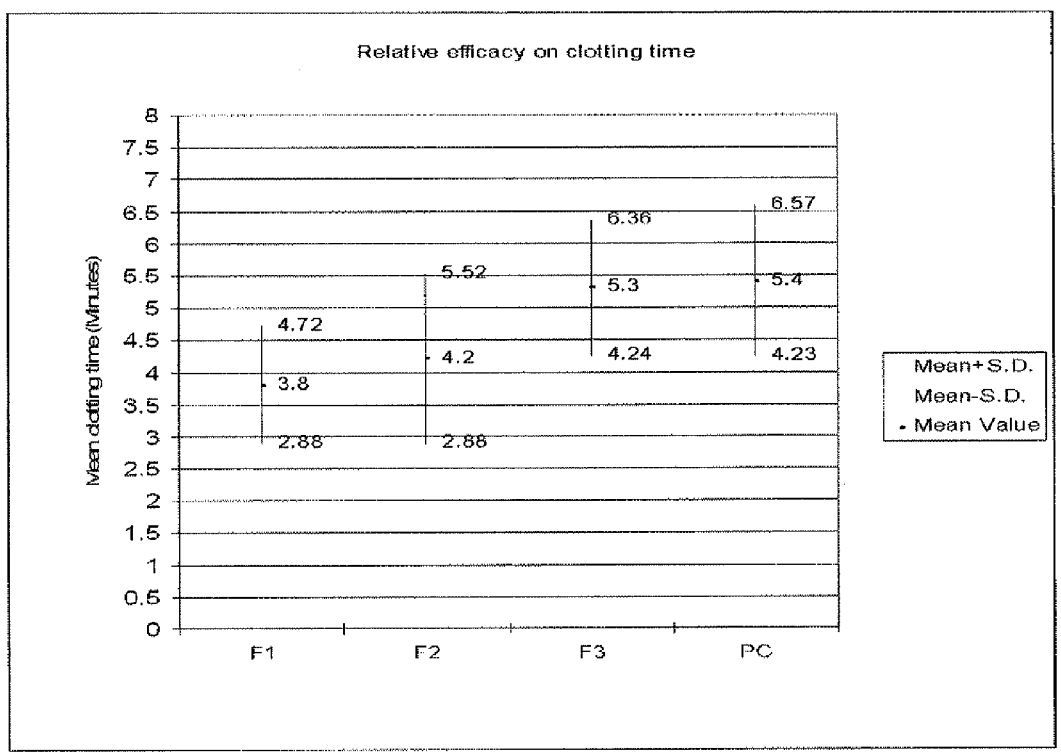
FIG. 9 depicts graphically the mean clotting time of acetylsalicyclic acid and L-serine, L-Threonine and L-hydroxy proline acetylsalicyclic acid.

The group mean data of animals comparing the Relative Efficacy of L-serine, L-Threonine, and L-Hydroxyproline esters of acetylsalicylic acid to each and compared to acetylsalicylic acid on Mean Clotting Time (±SD.) in Minutes is depicted in FIG. 9.

The statistical analysis of FIG. 9 showed that L-Threonine, and L-Hydroxyproline esters of acetylsalicylic acid are as effective as acetylsalicylic acid. There is no significant difference at 5% significance level for L-Hydroxyproline ester of acetylsalicylic acid and L-Threonine ester of acetylsalicylic with respect to positive control for the mean blood clotting time observed after two hours. However, combined with the gastric irritation potential, the L-serine, L-Threonine, and L-Hydroxyproline esters of acetylsalicylic acid are far superior (See FIG. 10).

Figure 10:
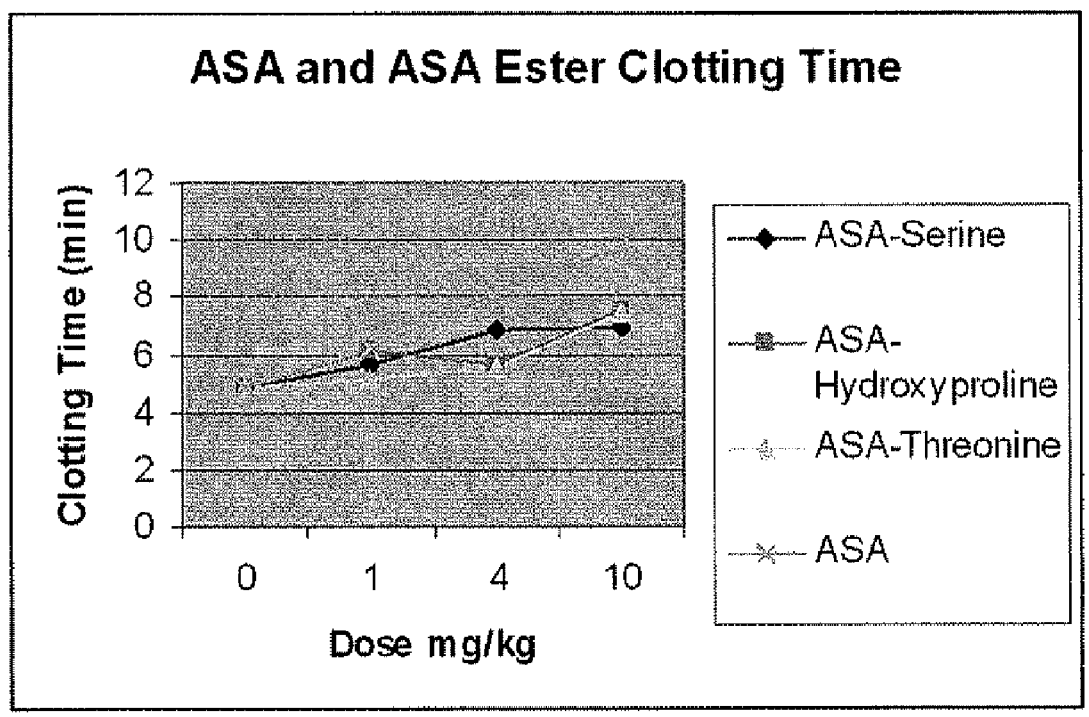
FIG. 10 shows clotting time in minutes versus doses administered to rats at 1,4 and 10 mg/kg for test drugs, ASA-Serine Ester, ASA-Hydroxyproline Ester and ASA-Threonine Ester versus Aspirin as the reference standard.

FIG. 10 shows a clotting time in minutes verses doses administered to rats at 1, 4 and 10 mg/kg for test drugs ASA-Serine Ester, ASA-Hydroxyproline Ester and ASA-Threonine Ester versus Aspirin. Statistically significant increases clotting time was noted for all test and reference drugs at 10 mg/kg dose.

The following additional data were obtained, when the same drugs were compared in rats on a different date with different time intervals and doses:

TABLE 14

|  | Clotting Time (min) | | | | |
|---|---|---|---|---|---|
| Dose | ASA-Serine | ASA-HP | ASA-T | ASA | Vehicle |
| 10 mg/kg 1 hr | 6.9 | 7.5 | 7.4 | 9.8 | 4.9 |
| 10 mg/kg 24 hr | 4.4 | 3.3 | 3.6 | 4.4 | 2.7 |
| 20 mg/kg 2 hr | 3.8 | 4.2 | 5.3 | 5.4 | 2.7 |

Two of the better esters of ASA at various conditions are as follows:

10 mg/kg 1 hr ASA-HP and ASA-T
10 mg/kg 24 hr ASA-S and ASA-T
20 mg/kg 2 hr ASA-HP and ASA-T Thus Acetylsalicylic Acid-L-Threonine Ester (ASA-T) was the preferred derivative for treatment in the advanced Chronic 28 Day Toxicity Studies.

Note: The statistical analysis showed that L-Threonine, and L-Hydroxyproline esters of acetylsalicylic acid are as effective as acetylsalicylic acid. There is no significant difference at 5% significance level for L-Hydroxyproline ester of acetylsalicylic acid and L-Threonine ester of acetylsalicylic with respect to positive control for the mean blood clotting time observed after two hours. However, combined with the gastric irritation potential, the L-serine, L-Threonine, and L-Hydroxyproline esters of acetylsalicylic acid are far superior. Furthermore, when compared against esters, L-Threonine Ester of Aspirin seems to be the ideal candidate as it showed consistently better response in the rat blood clotting time.

Based upon consistently improved toxicity profile, efficacy and better therapeutic index, Acetylsalicylic Acid-L-Threonine Ester was advanced to GMP synthesis.

Results of the 28-Day Chronic Dosing in Rodents, Comparative Toxicology:

The purpose of this study is to establish the toxicity of Acetylsalicylic Acid-L-Threonine Ester in relation to Aspirin (Make: Sigma, Batch number 090K0884) which served as a reference drug by conducting a 28-day repeated dose oral toxicity test in male and female albino rats.

Aspirin and Acetylsalicylic Acid-L-Threonine Ester were administered to albino rats (Wistar strain), by oral gavage daily for a period of 28 days, using 0.5% Carboxymethylcellulose (CMC) in phosphate buffer solution (pH 2.6) as vehicle. The study was conducted at one dose level only along with a vehicle control group as per the recommendation of the Sponsor. The test doses are expressed as Aspirin molar equivalents. Acetylsalicylic Acid-L-Threonine Ester was compared against Aspirin and Vehicle at 100 mg/kg dose administered to rats for 28 days.

The salient features of the study are as follows, where ASA-T represents Acetylsalicylic Acid-L-Threonine Ester:

1. All the animals of vehicle control group and the test group (Acetylsalicylic Acid-L-Threonine Ester) and reference control group (Aspirin) survived through the dosing period of 28 days.
2. None of the animals of the vehicle control group, test group (Acetylsalicylic Acid-L-Threonine Ester), and reference control group (Aspirin) exhibited any clinical symptoms of toxicity through out the dosing period.
3. Changes in the Body weight.

TABLE 15

| Body Weight | Comparison | Significance[P < 0.05] |
| --- | --- | --- |
| Gain | ASA-T vs Aspirin vs Vehicle | Normal (Male) |
| Gain | ASA-T and Aspirin vs Vehicle | Decrease (Female) |

The percentage decrease were 29% and 21% for Acetylsalicylic Acid-L-Threonine Ester and Aspirin 4. Food intake of the animals of both the sexes of test group (Acetylsalicylic Acid-L-Threonine Ester) and reference control group (Aspirin) was found to be normal and comparable to the animals of vehicle control group.
5. Results of hematological analysis of the animals of different groups are shown below:

TABLE 16

| Hematological | Comparison | Significance[P < 0.05] |
| --- | --- | --- |
| All Blood Parameters | ASA-T vs Aspirin vs Vehicle | None |
| Platelet Count | ASA-T vs Aspirin | Increase (Male) |

1. Results of clinical chemistry analysis of the animals of different groups are summarized below:

TABLE 17

| Clinical Chemistry | Comparison | Significance[P < 0.05] |
| --- | --- | --- |
| Alkaline Phosphatase | AST-T Ester vs Vehicle | Increase (Female) |
| Total Protein | ASA-T Ester vs Vehicle | Increase (Female) |
| Creatinine | ASA-T Ester vs Vehicle | Decrease (Male) |
| Cholesterol | ASA-T Ester vs Vehicle | Increase (Male) |
| Alkaline Phosphatase | Aspirin vs Vehicle | Increase (Female) |
| Sodium | Aspirin vs Vehicle | Increase (Female) |
| Blood Urea | Aspirin vs Vehicle | Decrease (Female) |
| SGPT and Cholesterol | Aspirin vs Vehicle | Increase (Male) |
| All Clinical Chemistry | ASA-T Ester vs Aspirin | None(but two below) |
| Blood Glucose | ASA-T Ester vs Aspirin | Decrease (Female) |
| Creatinine | ASA-T Ester vs Aspirin | Decrease (Male) |

Necropsy of the surviving animals at the end of the study (terminal necropsy) of vehicle control and different treatment groups did not reveal any gross pathological changes in any of the vital organs. Further there is no evidence of gastric mucosal irritation in the animals of vehicle control, test group (ASA-T Ester) and reference control group (Aspirin).

The data on absolute (Abs) and relative (Rel) organ weights of liver, kidney, adrenals, heart, spleen and testes showed the following changes in the organ weights:

TABLE 18

| Rel/Abs Organ Wts | Comparison | Significance[P < 0.05] |
| --- | --- | --- |
| Adrenals (Abs) | ASA-T Ester vs Vehicle | Decrease (Male) |
| Kidney (Abs) | Aspirin vs Vehicle | Decrease (Male) |
| Spleen (Abs) | Aspirin vs Vehicle | Decrease (Female) |
| Kidney (Rel) | Aspirin vs Vehicle | Increase (Male) |
| Spleen (Rel) | Aspirin vs Vehicle | Increase (Female) |
| Kidney (Abs) | ASA-T Ester vs Aspirin | Decrease (Male) |
| Spleen (Abs) | ASA-T Ester vs Aspirin | Decrease (Male) |
| Kidney (Rel) | ASA-T Ester vs Aspirin | Increase (Male) |

Histological sections of the following organs viz. brain, stomach, small intestines, large intestine, liver, kidney, adrenal, spleen, heart, lungs and gonads of male and female animals treated with Acetylsalicylic Acid-L-Threonine Ester or reference drug (Aspirin) groups did not show any histopathological changes and were found to be normal and comparable to that of animals of vehicle control group. However few animals treated with reference drug (Aspirin) showed mild fatty changes in the cardiac muscle fibers of heart and mild catarrhal changes of gastric mucosa.

Human Clinical Trials:

Several blood clotting time studies were done in a limited number of human volunteers with Acetylsalicylic Acid-L-Threonine Ester. Results are shown in FIGS. 11-14.

Figure 11:
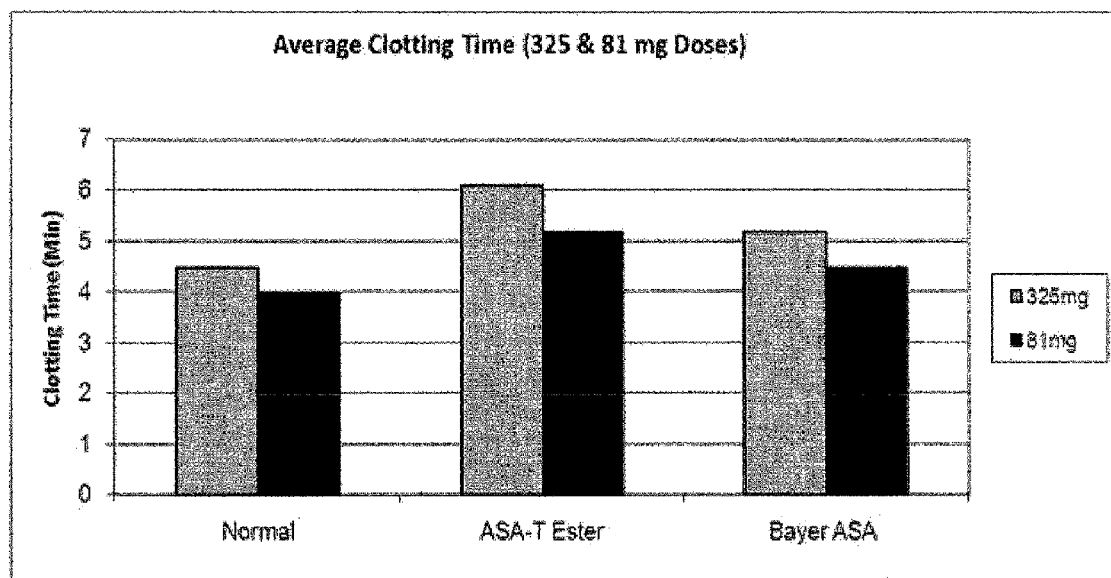
FIG. 11 depicts the average Clotting time after 325 mg and 81 mg Acetylsalicylic Acid-L-Threonine Ester and Bayer Aspirin is administered to human Volunteers. The first set of columns (Normal) is the average clotting times observed prior to administration of the Aspirin derivative and Aspirin.

Acetylsalicylic Acid-L-Threonine Ester at low dose of 80 mg was as effective as 325 mg Bayer Aspirin (with baseline correction)! And, it is more effective than 81 mg Bayer Aspirin as the results in FIG. 11 show.

FIG. 11 depicts Average Clotting Time after 325 mg and 81 mg Acetysalicylic Acid-L-Threonine Ester and Bayer Aspirin is administered to human Volunteers. The first set of columns (Normal) is average clotting times observed prior to administration of the Aspirin derivative and Aspirin—This data is given in table 19 below.

Table 19 shows the Comparative average clotting time (min) details of Acetylsalicylic Acid-L-Threonine Ester vs. Bayer ASA at 325 mg and 81 mg levels.

TABLE 19

| | AVERAGE CLOTTING TIME (MIN) | | | | |
|---|---|---|---|---|---|
| | 325 mg ASA-T ESTER Volunteer 1 | 325 mg ASA Bayer Volunteer 2 | 81 mg ASA-T ESTER Volunteer 1 | 81 mg ASA Bayer Volunteer 2 | 81 mg ASA-T ESTER Volunteer 3 |
| Normal | 4.5 | 4.5 | 4 | 4 | 4 |
| With ASA-T ESTER | 6.2 | 6.0 | 5.2 | NA | 5.1 |
| With ASA (Bayer) | 5.7 | 5.7 | NA | 4.5 | NA |

Figure 12:
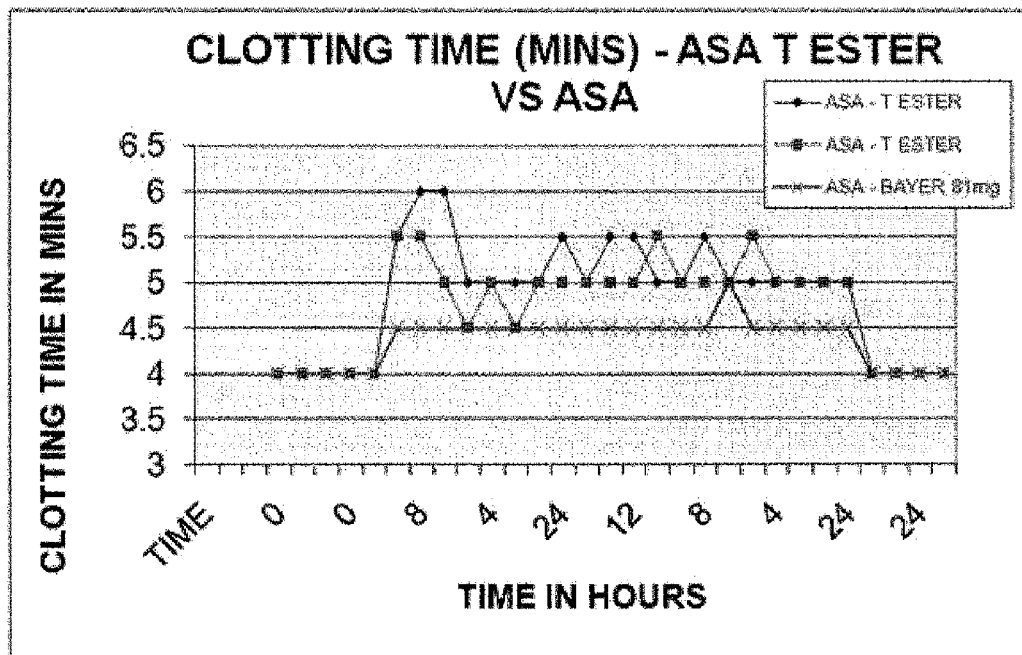
FIG. 12 shows clotting time in minutes −5 day administration of 81 mg ACETYLSALICYLIC ACID-L-THREONINE ESTER and Bayer Aspirin in Human Volunteers. Total of 3 volunteers participated in this study. Two volunteers took ACETYLSALICYLIC ACID-L-THREONINE ESTER (bottom line in FIG. 12).

FIG. 12 shows the clotting time in minutes –5 day administration of 81 mg Acetylsalicyclic Acid L-Threonine Ester and Bayer Aspirin in human volunteers. A total of three volunteers participated in the study, two took Acetylsalicyclic Acid L-Threonine ester (bottom line in FIG. 12).

Figure 13:
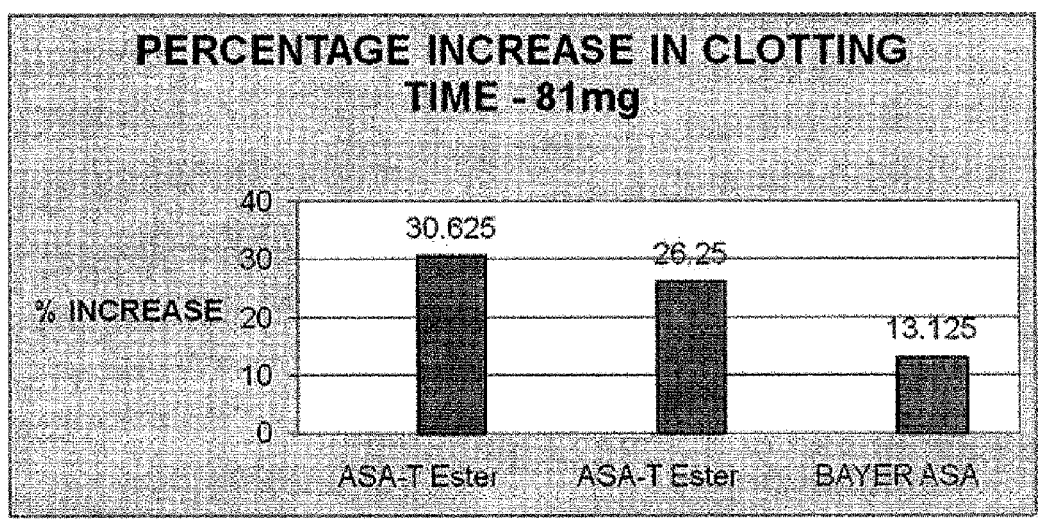
FIG. 13 graphically depicts percentage increase in clotting time of Acetylsalicylic Acid-L-Threonine Ester vs. Aspirin (Bayer) at 81 mg dose based on 5-day average increase. The two Acetylsalicylic Acid-L-Threonine Ester blocks shown correspond to two separate volunteers who took the test drug over a period of 5 days. The third volunteer took Bayer Aspirin for 5 days.
Figure 14:
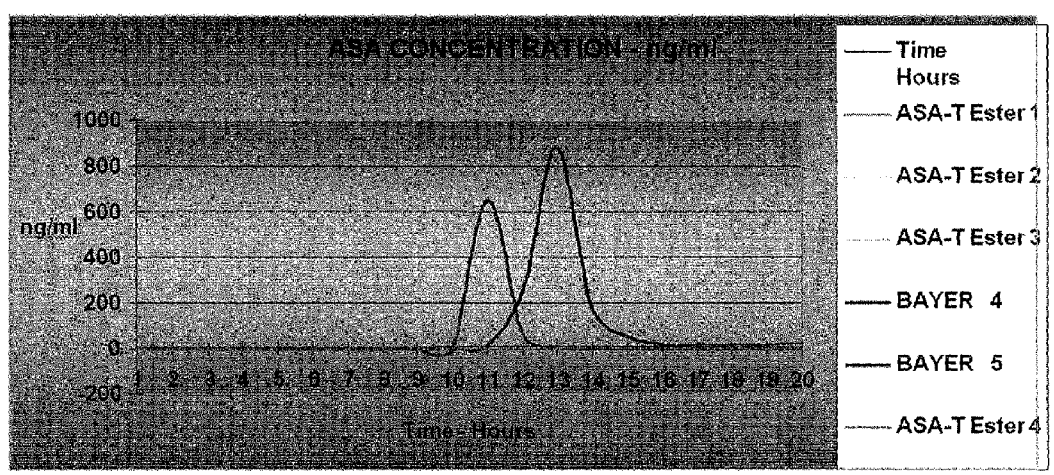
FIG. 14 is a plot of the concentration of Aspirin versus time in 4 volunteers who took Acetylsalicylic Acid-L-Threonine Ester and 2 volunteers who took Bayer Aspirin.

FIG. 13 graphically depicts the percentage increase in clotting time of the Acetylsalicyclic Acid L-Threonine Ester relative to Aspirin (Bayer) at 81 mg dose based on a five day average increase. This plot was derived from Table 13. The two acetylsalicyclic L-Threonine esters blocks shown in FIG. 13 correspond to two separate volunteers who took the test drug over a period of five days. The third volunteer took Bayer Aspirin for five days. As shown hereinbelow, an increase in clotting time occurred on the very first day of drug intake and remained higher than Bayer ASA during the subsequent administrations FIG. 14 shows pharmacokinetic results in 4 volunteers who took Acetylsalicyclic Acid-L-Threonine Ester versus two volunteers who took Bayer Aspirin at 325 mg dose.

Therefore, as shown by the data, Acetylsalicylic Acid-L-Threonine Ester is a Superior Anti platelet drug:

1. Does not produce any gastric irritation;
2. Does not inhibit prostaglandin synthesis;
3. Does not have any COX-1 or COX-2 activity on the endothelial or vascular tissues, as no ASA from Acetylsalicyclic Acid-L-Threonine Ester reaches systemic circulation.
4. Thus, none of the side effects of Aspirin are seen with Acetylsalicyclic Acid-L-Threonine Ester.

Figure 15:
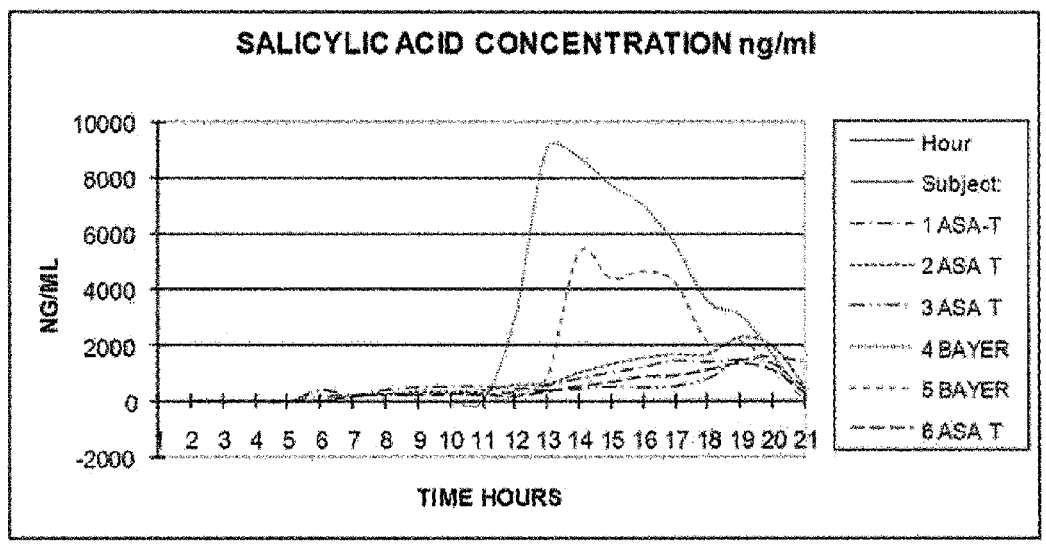
FIG. 15 is a plot of the plasma concentration of Salicylic Acid versus time in human plasma for 4 volunteers who took Acetylsalicylic Acid-L-Threonine Ester and two volunteers who took Aspirin.

FIG. 15 graphically depicts a plot of plasma concentration of salicyclic Acid versus time in human plasma in four volunteers who ingested Acetylsalicyclic Acid-L-Threonine ester and two volunteers who ingested aspirin.

Rapid influx and efflux of Salicylic Acid from Aspirin administration was seen in the two volunteers who took Aspirin (FIG. 15). There was prolonged and sustained formation and disappearance of Salicylic acid in volunteers who took Acetylsalicyclic Acid-L-Threonine Ester (FIG. 15). This is indicative of the fact the there is a high likelihood of Acetylsalicylic Acid-L-Threonine Ester exhibiting sustained, specific and irreversible acetylation of the platelets in the portal circulation. Since there was no aspirin found in the systemic circulation after oral dosing of Acetylsalicyclic Acid-L-Threonine Ester, it is likely that site specific action of acetylation of the platelets has been achieved, and the unwanted effect of aspirin in the endothelial system has been avoided. Thus it is evident from the human pharmacokinetic studies, clinical trials, rat gastric mucosa irritation results, Acetylsalicyclic Acid-L-Threonine Ester is a superior anti-platelet drug that does not have the toxicity of Aspirin and also has a better Therapeutic Index.

Anti-Hyperlipidemic Effect of Fenofibric Acid Derivatives:

Surprisingly, the L-threonine derivatives of Fenofibric acids made are either equipotent or showed better efficacy in rat anti-hyperlipidemic model. In this study, Albino rats were placed on a hypertriglyceridemic diet, viz., 30% sucrose in drinking water for a period 7 days. The sucrose solution was supplied ad libitum along with normal diet. Albino rats were administered with appropriate daily dose of the test item daily for a period of 7 days from day 8 to 14. During this period rats are provided with normal diet only. Blood samples were collected on day zero (before providing sucrose solution) on day 7 (before the start of first dose) and on day 14 (end of the study). Serum was separated and analyzed for triglycerides. Basing on the data the hypolipidemic property of the ester of Fenofibric acid were evaluated with reference to fenofibrate (reference control). The results are shown in the following table, where Fen-S Ester, Fen-T Ester and Fen-HP Ester are Fenofibric Acid L-Serine Ester, Fenofibric Acid L-Threonine ester and Fenofibric Acid L-Hydroxyproline ester respectively.

TABLE 20

Anti-lipidemic Effects of Fenofibric Acid and its Derivatives

| | Dose | Absolute Change from day 0 | Absolute Change from day 7 | % Change from day 0 | % Change from day 7 |
|---|---|---|---|---|---|
| Vehicle | mg/kg | 50.4 | −5.6 | 83.17% | −4.80% |
| Fen-S Ester | 25 | −54 | −90 | −61.64% | −72.82% |
| | 50 | −31.4 | −84.2 | −44.10% | −67.90% |
| | 100 | −20.8 | −72 | −33.23% | −63.27% |
| Fen-T Ester | 25 | −18.2 | −36.4 | −23.21% | −37.68% |
| | 50 | −23.8 | −77.6 | −35.00% | −63.71% |
| | 100 | −63.8 | −88.4 | −68.45% | −75.04% |
| Fen-HP Ester | 25 | −16 | −47.8 | −32.92% | −59.45% |
| | 50 | −35.8 | −70.8 | −49.31% | −65.80% |
| | 100 | −3.4 | −112 | −7.52% | −72.82% |
| Fenofibrate | 25 | −10.8 | −51 | −15.21% | −45.86% |
| | 50 | −13.4 | −87.6 | −22.95% | −66.06% |
| | 100 | −40.8 | −71.6 | −61.26% | −73.51% |

While all of the esters were active and showed efficacy, there were important distinguishing factors between the various esters and Fenofibrate. For example, dose dependent decrease in triglycerides were noted with L-Threonine ester, and also maximum decrease from baseline level and treatment level were also noted for this compound. Thus Fenofibric Acid-L-Threonine ester had overall superior anti-hyperlipidemic properties.

The in vitro methods include acid/base hydrolysis of the derivatives, hydrolysis in pig pancreas hydrolysis in rat intestinal fluid, hydrolysis in human gastric fluid, hydrolysis, as described in Simmons, D M, Chandran, V R and Portmann, G A, Danazol L-Threonine Derivatives: In Vitro and In Situ Biopharmaceutical Evaluation, Drug Development and Industrial Pharmacy, Vol 21, Issue 6, Page 687, 1995, the contents of all of which are incorporated by reference.

The compounds of the present invention are effective in treating diseases or conditions in which NSAIDs normally are used. The derivatives disclosed herein are transformed within the body to release the active compound and enhances the therapeutic benefits of the NSAIDs by reducing or eliminating biopharmaceutical and pharmacokenetic barriers associated with each of them. However it should be noted that these derivatives themselves will have sufficient activity without releasing any active drug in the mammals. Since the derivatives is more soluble in water then Ibuprofen or other NSAIDs, it does not need to be associated with a carrier vehicle, such as alcohol or castor oil which may be toxic or produce unwanted side reactions. Moreover, oral formulations containing the NSAID derivatives are absorbed into the blood and are quite effective.

Thus, the derivatives of the present invention enhance the therapeutic benefits by removing biopharmaceutical and pharmacokenetic barriers of existing drugs.

Furthermore, these derivatives are easily synthesized in high yields using reagents which are readily and commercially available.

As defined herein, the term lower alkyl refers to an alkyl group containing 1-6 carbon atoms. The alkyl groups may be straight chained or branched. Examples include, methyl, ethyl, propyl, isopropyl, n-butyl, sec butyl, isobutyl, t-butyl, n-pentyl amyl, isopentyl, hexyl and the like. The preferred lower alkyl group is methyl.

The term aryl refers to an aromatic ring containing only carbon ring atoms and having 6, 10 or 14 ring carbon atoms and up to a total of 18 carbon atoms. It may be moncyclic or bicyclic or tricyclic. If it contains more than 1 ring, the rings are all fused, but all of the rings are fully aromatic. Examples include phenyl, α-naphthyl, B-naphthyl and the like. The preferred aryl group is aryl.

Examples of aryl lower alkyl include benzyl, phenethyl, naphthylmethyl, naphthylethyl and the like.

The term cycloalkyl, as used herein, refers to an alicyclic hydrocarbon containing 3-14 ring carbon atoms and up to a total of 18 carbon atoms. It may be monocyclic or it may be bicyclic, tricyclic or tetracyclic. If it contains more than 1 ring, the rings are fused to each other. The cycloalkyl group may be fully saturated or partially saturated. It also may contain an aromatic moiety ring. Examples include cyclopropyl, cyclobutyl, cyclopentyl, cyclohexyl, cycloheptyl, cyclooctyl, decalinyl, norbornyl, adamantyl, indanyl, and the like. The preferred cycloalkyl contains 5-8 ring carbon atoms and especially 5-6 ring carbon atoms.

Examples of cycloalkyl lower alkyl include cyclohexylmethyl, cyclohexylethyl, trans-1,3-dimethyleyclohxyl, trans 1,3-dimethyl-cyclpentyl and the like.

The term heterocyclic refers to a cycloalkyl or aryl ring, as defined herein, wherein at least one of the ring carbon atoms has been substituted with a heteratom selected from nitrogen, sulfur or oxygen. The term heterocycles also includes the heteroaramatics. The heterocycle group may contain 1, 2, 3 or 4 ring heteratoms, but preferably 1 or 2 ring heteroatoms. Examples include furyl, tetrahydrofuryl, pyrridyl, pyrryl, thienyl, pyrazolyl, pyrrolyl, imidazolyl, indolyl, thiazolyl, oxazolyl, isothiazolyl, isoxazolyl, piperidyl, pyrrolinyl, piperazinyl, quinolyl, triazolyl, tetrazolyl, isoquinolyl, benzofuryl, benzothienyl, morpholinyl, benzoxazolyl, tetrahydrofuryl, purinyl, indolinyl, pyrazolindinyl, imidazolinyl, imadazolindinyl, pyrrolidinyl, furazanyl, N-methylindolyl, methylfuryl, pyridazinyl, pyrimidinyl, pyrazinyl, pyridyl, aziridino, oxetanyl, azetidinyl, the N-oxides of the nitrogen containing heterocycles, such as the nitric oxides of pyridyl, pyrazinyl, and pyrimidinyl and the like.

The terms "compounds of the present invention", "derivatives of the present invention", "drugs of the present invention" are used interchangeably. They refer to the drugs in which a L-Threonine moiety as described herein, is covalently bound to a drug or medicament.

The term ASA refers to acetyl salicyclic acid.

As used herein, the term "cage size toxicity" has been used with respect to the administration of ibuprofen and/or its derivatives. What this term refers to is that a number of animals died during the 28-day toxicity studies. However, in most instances there were no visible signs of impending death, such as lethargy, significant weight loss, loss of mobility, and other outward signs of approaching death that were noted. Therefore it was not easy to predict which of the animals would die. When the cages were opened, the next morning one or more animals were noted to be dead. Thus visual observation of toxicity of animals on the cage is also noted as "cage side specific toxicity".

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A L-Threonine ester of a drug wherein the drug is 5-HETE, Acetaminophen, Alfaprostol Acid, Arachadonic Acid, Beraprost, Capacitabine, Carboprost, Clofibric Acid, γ-Linolenic Acid, Diclofenac, Fenprostalene Acid, Fluprostenol, Gemprost, Leukotrienes, Limaprost, Mycophenolic Acid, Nicotinic Acid, Ozagrel, Propofol, Prostaglandins E1, E2, and F2alpha, Prostanoic Acid, Rosaprostol or Trimoprostil.

2. A pharmaceutical composition comprising the L-Threonine ester of the drug of claim 1 and a pharmaceutically acceptable carrier therefor.

3. The L-Threonine ester of a drug according to claim 1 wherein the drug and the Threonine is bonded by an ester linkage formed from the hydroxyl group in the Threonine and the carboxy group or acylating derivative thereof of the drug.

4. The L-Threonine ester of a drug according to claim 1 having a carboxy group on the drug.

5. The L-Threonine ester of a drug according to claim 1, which is substantially pure.

6. A method of facilitating the separation of a racemic mixture of a drug containing a carboxy or hydroxyl group into its separate stereoisomers which comprises reacting said drug with L-Threonine or acylating derivative thereof under conditions effective to form an ester linkage between said drug and L-Threonine or said acylating derivative and separating the stereoisomers thus formed, said drug being Alfaprostol Acid, Beraprost, Capacitabine, Carboprost, Fenprostalene Acid, Fluprostenol, Gemeprost, Leukotrienes, Limaprost, Prostaglandins E1, E2, and F2alpha, Prostanoic Acid, Rosaprostol or Trimoprostil.

* * * * *